(12) United States Patent
Donohoue et al.

(10) Patent No.: US 10,023,853 B1
(45) Date of Patent: *Jul. 17, 2018

(54) ENGINEERED NUCLEIC-ACID TARGETING NUCLEIC ACIDS

(71) Applicant: Caribou Biosciences, Inc., Berkeley, CA (US)

(72) Inventors: Paul Daniel Donohoue, Berkeley, CA (US); Andrew Paul May, San Francisco, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,202

(22) Filed: Mar. 12, 2018

Related U.S. Application Data

(63) Continuation of application No. 15/787,705, filed on Oct. 18, 2017, now Pat. No. 9,957,490, which is a continuation of application No. 15/675,677, filed on Aug. 11, 2017, now Pat. No. 9,816,081, which is a continuation of application No. 15/460,642, filed on Mar. 16, 2017, now Pat. No. 9,745,562, which is a continuation of application No. 15/331,676, filed on Oct. 21, 2016, now Pat. No. 9,677,090.

(60) Provisional application No. 62/245,918, filed on Oct. 23, 2015.

(51) Int. Cl.
| C12N 15/113 | (2010.01) |
| C12N 15/90  | (2006.01) |
| C12N 9/22   | (2006.01) |

(52) U.S. Cl.
CPC ............ *C12N 9/22* (2013.01); *C12N 15/113* (2013.01); *C12N 15/902* (2013.01)

(58) Field of Classification Search
CPC ....... C12N 9/22; C12N 15/902; C12N 15/113
See application file for complete search history.

(56) References Cited

U.S. PATENT DOCUMENTS

| 8,697,359 | B1 | 4/2014 | Zhang et al. |
| 8,771,945 | B1 | 7/2014 | Zhang et al. |
| 8,795,965 | B2 | 8/2014 | Zhang et al. |
| 8,841,260 | B2 | 9/2014 | Miller et al. |
| 8,865,406 | B2 | 10/2014 | Zhang et al. |
| 8,871,445 | B2 | 10/2014 | Zhang et al. |
| 8,889,356 | B2 | 11/2014 | Zhang et al. |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Zhang et al. |
| 8,945,839 | B2 | 2/2015 | Zhang et al. |
| 8,993,233 | B2 | 3/2015 | Zhang et al. |
| 8,999,641 | B2 | 4/2015 | Zhang et al. |
| 9,115,348 | B2 | 8/2015 | Haurwitz et al. |
| 9,260,752 | B1 | 2/2016 | May et al. |
| 2011/0223638 | A1 | 9/2011 | Wiedenheft et al. |
| 2013/0130248 | A1 | 5/2013 | Haurwitz et al. |
| 2014/0068797 | A1 | 3/2014 | Doudna et al. |
| 2014/0294773 | A1 | 10/2014 | Brouns et al. |
| 2014/0302563 | A1 | 10/2014 | Doudna et al. |
| 2014/0315985 | A1 | 10/2014 | May et al. |
| 2015/0024499 | A1 | 1/2015 | Brouns et al. |
| 2015/0045546 | A1 | 2/2015 | Siksnys et al. |
| 2015/0050699 | A1 | 2/2015 | Siksnys et al. |
| 2015/0059010 | A1 | 2/2015 | Cigan et al. |
| 2015/0082478 | A1 | 3/2015 | Cigan et al. |
| 2015/0284727 | A1 | 4/2015 | Kim et al. |
| 2015/0152398 | A1 | 6/2015 | Doudna et al. |
| 2015/0376586 | A1 | 12/2015 | May et al. |
| 2016/0046961 | A1 | 2/2016 | Jinek et al. |
| 2016/0208243 | A1 | 7/2016 | Zhang et al. |

FOREIGN PATENT DOCUMENTS

WO   WO 2015/071474   5/2015

OTHER PUBLICATIONS

Search Report for PCT/US2016/058294, which corresponds to parent application U.S. Appl. No. 15/460,642.
"A geminivirus-based guide RNA delivery system for CRISPR/Cas9 mediated plant genome editing," Yin, K., et al., Sci Rep. Oct. 9, 2015;5:14926. doi: 10.1038/srep14926.
"Highly efficient CRISPR/Cas9-mediated transgene knockin at the H11 locus in pigs," Ruan, J., et al., Sci Rep. Sep. 18, 2015;5:14253. doi: 10.1038/srep14253.
"Conditionally Stabilized dCas9 Activator for Controlling Gene Expression in Human Cell Reprogramming and Differentiation," Balboa, D., et al., Stem Cell Reports. Sep. 8, 2015;5(3):448-59. doi: 10.1016/j.stemcr.2015.08.001.
"Cas9-Guide RNA Directed Genome Editing in Soybean," Li, Z., et al., Plant Physiol. Oct. 2015;169(2):960-70. doi: 10.1104/pp.15.00783. Epub Aug. 20, 2015.
"CRISPR-Cas9 Genome Editing in *Drosophila*," Gratz, S.J., et al., Curr Protoc Mol Biol. Jul. 1, 2015;111:31.2.1-20. doi: 10.1002/0471142727.mb3102s111.
"GONAD: Genome-editing via Oviductal Nucleic Acids Delivery system: a novel microinjection independent genome engineering method in mice," Takahashi, G., et al., Sci Rep. Jun. 22, 2015;5:11406. doi: 10.1038/srep11406.
"Highly efficient CRISPR/Cas9-mediated knock-in in zebrafish by homology-independent DNA repair," Auer, T.O., et al., Genome Res. Jan. 2014;24(1):142-53. doi: 10.1101/gr.161638.113. Epub Oct. 31, 2013.
"Controlling transcription in human pluripotent stem cells using CRISPR-effectors," Genga, R.M., et al., Methods. May 15, 2016;101:36-42. doi: 10.1016/j.ymeth.2015.10.014. Epub Oct. 23, 2015.

(Continued)

*Primary Examiner* — Delia Ramirez
(74) *Attorney, Agent, or Firm* — Gary R. Fabian; Barbara G. McClung

(57) ABSTRACT

The present disclosure provides engineered cross-type-nucleic-acid targeting nucleic acids and compositions thereof. Nucleic acid sequences encoding the engineered cross-type-nucleic-acid targeting nucleic acids, as well as expression cassettes, vectors and cells comprising such nucleic acid sequences, are described. Also, methods are disclosed for making and using the engineered cross-type-nucleic-acid targeting nucleic acids and compositions thereof.

18 Claims, 23 Drawing Sheets

(56) References Cited

OTHER PUBLICATIONS

"CRISPR-Cas9 delivery to hard-to-transfect cells via membrane deformation," Han, X., et al., Sci Adv. Aug. 14, 2015;1(7):e1500454. doi: 10.1126/sciadv.1500454. eCollection Aug. 2015.
"Advances in therapeutic CRISPR/Cas9 genome editing," Savić, N., and Schwank, G., et al., Transl Res. Feb. 2016;168:15-21. doi: 10.1016/j.trsl.2015.09.008. Epub Sep. 26, 2015.
"Dimeric CRISPR RNA-Guided FokI-dCas9 Nucleases Directed by Truncated gRNAs for Highly Specific Genome Editing," Wyvekens, N., et al., Human Gene Therapy. Jul. 2015;26(7):425-31. doi: 10.1089/hum.2015.084.
Bassett, A. R., et al., "Highly Efficient Targeted Mutagenesis of *Drosophila* with the CRISPR/Cas9 System. Cell Reports," 4(1):220-228 (2013). doi.org/10.1016/j.celrep.2013.06.020.
Briner, A., et al., "Guide RNA Functional Modules Direct Cas9 Activity and Orthogonality," Molecular Cell 56(2):333-339 (2014).
Cho, S. W., et al., "Analysis of off-target effects of CRISPR/Cas-derived RNA-guided endonucleases and nickases," Genome Research, 24(1):132-141 (2014). doi.org/10.1101/gr.162339.113.
Dong D., et al., "The crystal structure of Cpf1 in complex with CRISPR RNA," Nature 532(7600):522-6. doi: 10.1038/nature17944 (2016).
Fonfara, I., et al., "The CRISPR-associated DNA-cleaving enzyme Cpf1 also processes precursor CRISPR RNA," Nature 532(7600):517-21. doi: 10.1038/nature17945 (2016).
Gao, M., et al., "Ago2 facilitates Rad51 recruitment and DNA double-strand break repair by homologous recombination," Cell Research 24:532-541 (2014).
Gao, P., et al., "Type V CRISPR-Cas Cpf1 endonuclease employs a unique mechanism for crRNA-mediated target DNA recognition," Cell Research 26:901-913. doi:10.1038/cr.2016.88 (2016).
Gardlik, et al., "Vectors and delivery systems in gene therapy," Medical Science Monitor 11(4):RA110-121 (2005).
Hilton, I., et al., "Epigenome editing by a CRISPR-Cas9-based acetyltransferase activates genes from promoters and enhancers," Nature Biotechnology 33(5):510-7; doi:10.1038/nbt.3199 (2015).
Hook, B., et al., "Analyzing Protein: Nucleic Acid Interactions Using HaloLink Protein Arrays," (Promega Corporation www.promega.com/resources/pubhub/analyzing-protein-nucleic-acid-interactions-using-halolink-protein-arrays/) (2011).
Houdebine, L.-M., "The methods to generate transgenic animals and to control transgene expression," Journal of Biotechnology 98(2-3):145-160 (2002).
Jinek, M., et al., "A programmable dual-RNA-guided DNA endonuclease in adaptive bacterial immunity," Science 337(6096):816-21 (2012).
Jinek, M., et al., "A programmable dual-RNA-guided DNA endonuclease in adaptive bacterial immunity," Science 337(6096):816-21 (2012); Supplemental Materials.
Jinek, M., et al., "RNA-programmed genome editing in human cells," eLife 2013;2:e00471. DOI: 10.7554/eLife.00471.
Kearns, N., et al., "Functional annotation of native enhancers with a Cas9-histone demethylase fusion," Nature Methods 12(5):401-3. doi: 10.1038/nmeth.3325 (2015).
Kleinstiver, B., et al., "Genome-wide specificities of CRISPR-Cas Cpf1 nucleases in human cells," Nature Biotechnology 34(8):869-74. doi: 10.1038/nbt.3620 (2016).
Makarova, K., et al., "Prokaryotic homologs of Argonaute proteins are predicted to function as key components of a novel system of defense against mobile genetic elements," Biol Direct 4:29. doi: 10.1186/1745-6150-4-29 (2009).
Makarova K.S., et al., "An updated evolutionary classification of CRISPR-Cas systems," Nat Rev Microbiol. 13(11):722-36 (2015). doi: 10.1038/nrmicro3569.
Ni X. et al., "Nucleic acid aptamers: clinical applications and promising new horizons," Current Medicinal Chemistry 18(27):4206-14 (2011).
Nishimasu, H., et al., "Crystal Structure of Cas9 in Complex with Guide RNA and Target DNA", Cell, 156(5):935-949 (2014). doi.org/10.1016/j.cell.2014.02.001.
O'Green, H., et al., "Using ChIP-seq Technology to Identify Targets of Zinc Finger Transcription Factors," Methods Mol Biol. 649:437-455 (2010). doi:10.1007/978-1-60761-753-2_27.
Phillips, A.J., "The challenge of gene therapy and DNA delivery," Journal of Pharmacy and Pharmacology 53(9):1169-1174 (2001).
Thermo Scientific Pierce, "Protein Interaction Technical Handbook," published by Thermo Fisher Scientific Inc. (Thermo Fisher Scientific Inc. 1601945; copyright 2010; tools.thermofishercom/content/sfs/brochures/1601945-Protein-Interactions-Handbook.pdf).
Wright, A. V., et al., "Rational design of a split-Cas9 enzyme complex," PNAS 112(10):2984-2989 (2015).
Yamano, T., et al., "Crystal Structure of Cpf1 in Complex with Guide RNA and Target DNA," Cell 165(4):949-62. doi: 10.1016/j.cell.2016.04.003 (2016).
Zetsche, B., et al., "Cpf1 Is a Single RNA-Guided Endonuclease of a Class 2 CRISPR-Cas System," Cell 163(3):759-71. doi: 10.1016/j.cell.2015.09.038 (2015).
U.S. Appl. No. 14/997,474, filed Jan. 15, 2016, U.S. Pat. No. 9,885,026, Feb. 6, 2018.
U.S. Appl. No. 15/802,413, filed Nov. 2, 2017.
U.S. Appl. No. 14/416,338, filed Jan. 22, 2015, U.S. Pat. No. 9,260,752, Feb. 16, 2016.
U.S. Appl. No. 14/751,055, filed Jun. 25, 2015, U.S. Pat. No. 9,410,198, Aug. 9, 2016.
U.S. Appl. No. 14/751,058, filed Jun. 25, 2015.
U.S. Appl. No. 15/344,487, filed Nov. 4, 2016.
U.S. Appl. No. 14/977,514, filed Dec. 21, 2015, U.S. Pat. No. 9,909,122, Mar. 6, 2018.
U.S. Appl. No. 15/159,619, filed May 19, 2016, U.S. Pat. No. 9,725,714, Aug. 8, 2017.
U.S. Appl. No. 15/159,776, filed May 19, 2016.
U.S. Appl. No. 15/904,285, filed Feb. 23, 2018.
U.S. Appl. No. 15/202,518, filed Jul. 5, 2016, U.S. Pat. No. 9,803,194, Oct. 31, 2017.
U.S. Appl. No. 15/660,906, filed Jul. 26, 2017, U.S. Pat. No. 9,809,814, Nov. 7, 2017.
U.S. Appl. No. 14/250,224, filed Apr. 10, 2014, U.S. Pat. No. 9,902,973, Feb. 27, 2018.
U.S. Appl. No. 15/851,674, filed Dec. 21, 2017.
U.S. Appl. No. 15/390,584, filed Dec. 26, 2016.
U.S. Appl. No. 14/836,753, filed Aug. 26, 2015.
U.S. Appl. No. 15/887,893, filed Feb. 2, 2018.
U.S. Appl. No. 14/835,675, filed Aug. 25, 2015, U.S. Pat. No. 9,580,727, Feb. 28, 2017.
U.S. Appl. No. 15/339,633, filed Oct. 31, 2016, U.S. Pat. No. 9,745,600, Aug. 29, 2017.
U.S. Appl. No. 15/665,155, filed Jul. 31, 2017.
U.S. Appl. No. 15/665,201, filed Jul. 31, 2017.
U.S. Appl. No. 15/253,725, filed Aug. 31, 2016.
U.S. Appl. No. 15/331,676, filed Oct. 21, 2016, U.S. Pat. No. 9,677,090, Jun. 13, 2017.
U.S. Appl. No. 15/460,642, filed Mar. 16, 2017, U.S. Pat. No. 9,745,562, Aug. 29, 2017.
U.S. Appl. No. 15/675,677, filed Aug. 11, 2017, U.S. Pat. No. 9,816,081, Nov. 14, 2017.
U.S. Appl. No. 15/787,705, filed Oct. 18, 2017.
U.S. Appl. No. 15/368,570, filed Dec. 2, 2016, U.S. Pat. No. 9,771,600, Sep. 26, 2017.
U.S. Appl. No. 15/703,992, filed Sep. 14, 2017.
U.S. Appl. No. 15/371,188, filed Dec. 6, 2016, U.S. Pat. No. 9,816,093, Nov. 14, 2017.
U.S. Appl. No. 15/787,630, filed Oct. 18, 2017.

SEQUENCE LISTING

<160> NUMBER OF SEQ ID NOS: 37

<210> SEQ ID NO 1
<211> LENGTH: 22
<212> TYPE: DNA
<213> ORGANISM: Artificial Sequence
<220> FEATURE:
<223> OTHER INFORMATION: Primer Sequence

<400> SEQUENCE: 1
agtgtaatac gactcactat ag                                             22

<210> SEQ ID NO 2
<211> LENGTH: 91
<212> TYPE: DNA
<213> ORGANISM: Artificial Sequence
<220> FEATURE:
<223> OTHER INFORMATION: Primer Sequence

<400> SEQUENCE: 2
taatacgact cactataggg gtgggggag tttgctccgt tttagagcta gaaatagcaa      60
gttgagataa ggctagtccg ttatcaactt g                                   91

<210> SEQ ID NO 3
<211> LENGTH: 91
<212> TYPE: DNA
<213> ORGANISM: Artificial Sequence
<220> FEATURE:
<223> OTHER INFORMATION: Primer Sequence

<400> SEQUENCE: 3
ccaggcactg cttctttctc taccatctac aacagtagaa attaagcacc gactcggtgc     60
cactttttca agttgataac ggactagcct t                                   91

<210> SEQ ID NO 4
<211> LENGTH: 24
<212> TYPE: DNA
<213> ORGANISM: Artificial Sequence
<220> FEATURE:
<223> OTHER INFORMATION: Primer Sequence

<400> SEQUENCE: 4
ccaggcactg cttctttctc tacc                                           24

<210> SEQ ID NO 5
<211> LENGTH: 141
<212> TYPE: RNA
<213> ORGANISM: Artificial Sequence
<220> FEATURE:
<223> OTHER INFORMATION: Cas9-Cpf1 NATNA1 Sequence

<400> SEQUENCE: 5
gggugggggg aguuugcucc guuuuagagc uagaaauagc aaguugagau aaggcuaguc     60
cguuaucaac uugaaaaagu ggcaccgagu cggugcuuaa uuucuacugu uguagauggu    120
agagaaagaa gcagugccug g                                             141

<210> SEQ ID NO 6
<211> LENGTH: 52
<212> TYPE: DNA
<213> ORGANISM: Artificial Sequence
<220> FEATURE:
<223> OTHER INFORMATION: Primer Sequence

<400> SEQUENCE: 6
cactctttcc ctacacgacg ctcttccgat ctccagatgg cacattgtca ga     52

<210> SEQ ID NO 7
<211> LENGTH: 47
<212> TYPE: DNA
<213> ORGANISM: Artificial Sequence
<220> FEATURE:
<223> OTHER INFORMATION: Primer Sequence

<400> SEQUENCE: 7
ggagttcaga cgtgtgctct tccgatctcc tagtgactgc cgtctgc     47

<210> SEQ ID NO 8
<211> LENGTH: 52
<212> TYPE: DNA
<213> ORGANISM: Artificial Sequence
<220> FEATURE:
<223> OTHER INFORMATION: Primer Sequence

<400> SEQUENCE: 8
cactctttcc ctacacgacg ctcttccgat ctaaggaacc tggagaccat ca     52

<210> SEQ ID NO 9
<211> LENGTH: 48
<212> TYPE: DNA
<213> ORGANISM: Artificial Sequence
<220> FEATURE:
<223> OTHER INFORMATION: Primer Sequence

<400> SEQUENCE: 9
ggagttcaga cgtgtgctct tccgatctga aaggcactga gtgggaag     48

<210> SEQ ID NO 10
<211> LENGTH: 23
<212> TYPE: DNA
<213> ORGANISM: Artificial Sequence
<220> FEATURE:
<223> OTHER INFORMATION: Protospacer Sequences

<400> SEQUENCE: 10
gtgccctcgg tcacactgtg tgg     23

<210> SEQ ID NO 11
<211> LENGTH: 28
<212> TYPE: DNA
<213> ORGANISM: Artificial Sequence
<220> FEATURE:
<223> OTHER INFORMATION: Protospacer Sequences

<400> SEQUENCE: 11
tttctctgat gttccctcaa ctgtcacc     28

<210> SEQ ID NO 12
<211> LENGTH: 141
<212> TYPE: RNA
<213> ORGANISM: Artificial Sequence
<220> FEATURE:
<223> OTHER INFORMATION: ERBB2-Cas9-Cpf1 NATNA Sequence

<400> SEQUENCE: 12
gugcccucgg ucacacugug guuuuagagc uagaaauagc aaguugagau aaggcuaguc     60
cguuaucaac uugaaaaagu ggcaccgagu cggugcuuaa uuucuacugu uguagauucu     120
gauguucccu caacugucac c     141

<210> SEQ ID NO 13
<211> LENGTH: 47
<212> TYPE: DNA
<213> ORGANISM: Artificial Sequence
<220> FEATURE:
<223> OTHER INFORMATION: Primer Sequence

<400> SEQUENCE: 13
cactctttcc ctacacgacg ctcttccgat ctctgccccg ggcgctg        47

<210> SEQ ID NO 14
<211> LENGTH: 47
<212> TYPE: DNA
<213> ORGANISM: Artificial Sequence
<220> FEATURE:
<223> OTHER INFORMATION: Primer Sequence

<400> SEQUENCE: 14
ggagttcaga cgtgtgctct tccgatctgg tcacaggggt tggaagg        47

<210> SEQ ID NO 15
<211> LENGTH: 57
<212> TYPE: DNA
<213> ORGANISM: Artificial Sequence
<220> FEATURE:
<223> OTHER INFORMATION: Primer Sequence

<400> SEQUENCE: 15
caagcagaag acggcatacg agattacgtg atgtgactgg agttcagacg tgtgctc    57

<210> SEQ ID NO 16
<211> LENGTH: 58
<212> TYPE: DNA
<213> ORGANISM: Artificial Sequence
<220> FEATURE:
<223> OTHER INFORMATION: Primer Sequence

<400> SEQUENCE: 16
aatgatacgg cgaccaccga gatctacacc gtctaataca ctctttccct acacgacg    58

<210> SEQ ID NO 17
<211> LENGTH: 61
<212> TYPE: DNA
<213> ORGANISM: Artificial Sequence
<220> FEATURE:
<223> OTHER INFORMATION: Primer Sequence

<400> SEQUENCE: 17
taatacgact cactatagaa tttctactgt tgtagatgaa aggggggtggg gggagtttgc    60 t                                                                   61

<210> SEQ ID NO 18
<211> LENGTH: 61
<212> TYPE: DNA
<213> ORGANISM: Artificial Sequence
<220> FEATURE:
<223> OTHER INFORMATION: Primer Sequence

<400> SEQUENCE: 18
taatacgact cactatagaa tttctactgt tgtagatggt agagaaagaa gcagtgcctg    60
g                                                                   61

<210> SEQ ID NO 19
<211> LENGTH: 78

```
<212> TYPE: DNA
<213> ORGANISM: Artificial Sequence
<220> FEATURE:
<223> OTHER INFORMATION: Primer Sequence

<400> SEQUENCE: 19
taatacgact cactataggt ctaagaactt taaataattt ctactgttgt agatgaaagg    60
gggtgggggg agtttgct                                                 78

<210> SEQ ID NO 20
<211> LENGTH: 78
<212> TYPE: DNA
<213> ORGANISM: Artificial Sequence
<220> FEATURE:
<223> OTHER INFORMATION: Primer Sequence

<400> SEQUENCE: 20
taatacgact cactataggt ctaagaactt taaataattt ctactgttgt agatggtaga    60
gaaagaagca gtgcctgg                                                 78

<210> SEQ ID NO 21
<211> LENGTH: 85
<212> TYPE: DNA
<213> ORGANISM: Artificial Sequence
<220> FEATURE:
<223> OTHER INFORMATION: Primer Sequence

<400> SEQUENCE: 21
taatacgact cactatagaa tttctactgt tcactgccgt ataggcagtg aacttgtaga    60
tgaaaggggg tggggggagt ttgct                                         85

<210> SEQ ID NO 22
<211> LENGTH: 85
<212> TYPE: DNA
<213> ORGANISM: Artificial Sequence
<220> FEATURE:
<223> OTHER INFORMATION: Primer Sequence

<400> SEQUENCE: 22
taatacgact cactatagaa tttctactgt tcactgccgt ataggcagtg aacttgtaga    60
tggtagagaa agaagcagtg cctgg                                         85

<210> SEQ ID NO 23
<211> LENGTH: 86
<212> TYPE: DNA
<213> ORGANISM: Artificial Sequence
<220> FEATURE:
<223> OTHER INFORMATION: Primer Sequence

<400> SEQUENCE: 23
taatacgact cactatagaa tttctactgt tgtagatgaa agggggtggg gggagtttgc    60
tgccaggttc actgccgtat aggcag                                        86

<210> SEQ ID NO 24
<211> LENGTH: 86
<212> TYPE: DNA
<213> ORGANISM: Artificial Sequence
<220> FEATURE:
<223> OTHER INFORMATION: Primer Sequence

<400> SEQUENCE: 24
taatacgact cactatagaa tttctactgt tgtagatggt agagaaagaa gcagtgcctg    60
```

```
ggccaggttc actgccgtat aggcag                                        86
```

<210> SEQ ID NO 25
<211> LENGTH: 86
<212> TYPE: DNA
<213> ORGANISM: Artificial Sequence
<220> FEATURE:
<223> OTHER INFORMATION: Primer Sequence

<400> SEQUENCE: 25

```
taatacgact cactataggt tcactgccgt ataggcaggc aagaatttct actgttgtag   60
atgaaagggg gtgggggggag tttgct                                       86
```

<210> SEQ ID NO 26
<211> LENGTH: 86
<212> TYPE: DNA
<213> ORGANISM: Artificial Sequence
<220> FEATURE:
<223> OTHER INFORMATION: Primer Sequence

<400> SEQUENCE: 26

```
taatacgact cactataggt tcactgccgt ataggcaggc aagaatttct actgttgtag   60
atggtagaga aagaagcagt gcctgg                                        86
```

<210> SEQ ID NO 27
<211> LENGTH: 24
<212> TYPE: DNA
<213> ORGANISM: Artificial Sequence
<220> FEATURE:
<223> OTHER INFORMATION: Primer Sequence

<400> SEQUENCE: 27

```
agcaaactcc ccccacccccc tttc                                         24
```

<210> SEQ ID NO 28
<211> LENGTH: 44
<212> TYPE: RNA
<213> ORGANISM: Artificial Sequence
<220> FEATURE:
<223> OTHER INFORMATION: Modified Cpf1-crRNA Sequence

<400> SEQUENCE: 28

```
gaauuucuac uguguagau gaaaggggggu gggggggaguu ugcu                   44
```

<210> SEQ ID NO 29
<211> LENGTH: 44
<212> TYPE: RNA
<213> ORGANISM: Artificial Sequence
<220> FEATURE:
<223> OTHER INFORMATION: Modified Cpf1-crRNA Sequence

<400> SEQUENCE: 29

```
gaauuucuac uguguagau gguagagaaa gaagcagugc cugg                     44
```

<210> SEQ ID NO 30
<211> LENGTH: 61
<212> TYPE: RNA
<213> ORGANISM: Artificial Sequence
<220> FEATURE:
<223> OTHER INFORMATION: Modified Cpf1-cr-RNA Sequence

<400> SEQUENCE: 30

```
ggucuaagaa cuuuaaauaa uuucuacugu uguagaugaa aggggguggg gggaguuugc   60
u                                                                   61
```

<210> SEQ ID NO 31
<211> LENGTH: 61
<212> TYPE: RNA
<213> ORGANISM: Artificial Sequence
<220> FEATURE:
<223> OTHER INFORMATION: Modified Cpf1-crRNA Sequence

<400> SEQUENCE: 31
ggucuaagaa cuuuaaauaa uuucuacugu uguagauggu agagaaagaa gcagugccug    60
g                                                                   61

<210> SEQ ID NO 32
<211> LENGTH: 68
<212> TYPE: RNA
<213> ORGANISM: Artificial Sequence
<220> FEATURE:
<223> OTHER INFORMATION: Modified Cpf1-crRNA Sequence

<400> SEQUENCE: 32
gaauuucuac uguucacugc cguauaggca gugaacuugu agaugaaagg ggguggggggg   60 aguuugcu                                                            68

<210> SEQ ID NO 33
<211> LENGTH: 68
<212> TYPE: RNA
<213> ORGANISM: Artificial Sequence
<220> FEATURE:
<223> OTHER INFORMATION: Modified Cpf1-crRNA Sequence

<400> SEQUENCE: 33
gaauuucuac uguucacugc cguauaggca gugaacuugu agaugguaga gaaagaagca    60
gugccugg                                                            68

<210> SEQ ID NO 34
<211> LENGTH: 69
<212> TYPE: RNA
<213> ORGANISM: Artificial Sequence
<220> FEATURE:
<223> OTHER INFORMATION: Modified Cpf1-crRNA Sequence

<400> SEQUENCE: 34
gaauuucuac uguuguagau gaaaggggggu gggggaguu ugcugccagg uucacugccg    60
uauaggcag                                                           69

<210> SEQ ID NO 35
<211> LENGTH: 69
<212> TYPE: RNA
<213> ORGANISM: Artificial Sequence
<220> FEATURE:
<223> OTHER INFORMATION: Modified Cpf1-crRNA Sequence

<400> SEQUENCE: 35
gaauuucuac uguuguagau gguagagaaa gaagcagugc cugggccagg uucacugccg    60
uauaggcag                                                           69

<210> SEQ ID NO 36
<211> LENGTH: 69
<212> TYPE: RNA
<213> ORGANISM: Artificial Sequence
<220> FEATURE:
<223> OTHER INFORMATION: Modified Cpf1-crRNA Sequence

```
<400> SEQUENCE: 36
gguucacugc cguauaggca ggcaagaauu ucuacuguug uagaugaaag ggggugggg      60 gaguuugcu                                                             69

<210> SEQ ID NO 37
<211> LENGTH: 69
<212> TYPE: RNA
<213> ORGANISM: Artificial Sequence
<220> FEATURE:
<223> OTHER INFORMATION: Modified Cpf1-crRNA Sequence

<400> SEQUENCE: 37
gguucacugc cguauaggca ggcaagaauu ucuacuguug uaguggaug agaaagaagc      60 agugccugg                                                             69
```

ENGINEERED NUCLEIC-ACID TARGETING NUCLEIC ACIDS

CROSS-REFERENCE TO RELATED APPLICATIONS

This application is a continuation of U.S. patent application Ser. No. 15/787,705, filed 18 Oct. 2017, now U.S. Pat. No. 9,957,490, issued May 1, 2018, which is a continuation of U.S. patent application Ser. No. 15/675,677, filed 11 Aug. 2017, now U.S. Pat. No. 9,816,081, issued 14 Nov. 2017, which is a continuation of U.S. patent application Ser. No. 15/460,642, filed 16 Mar. 2017, now U.S. Pat. No. 9,745,562, issued 29 Aug. 2017, which is a continuation of U.S. patent application Ser. No. 15/331,676, filed 21 Oct. 2016, now U.S. Pat. No. 9,677,090, issued 13 Jun. 2017, and claims the benefit of U.S. Provisional Patent Application Ser. No. 62/245,918, filed 23 Oct. 2015, which applications are herein incorporated by reference in their entirety.

STATEMENT REGARDING FEDERALLY SPONSORED RESEARCH OR DEVELOPMENT

Not applicable.

SEQUENCE LISTING

The present application contains a Sequence Listing that has been submitted electronically in ASCII format and is hereby incorporated by reference in its entirety. The ASCII copy, created on 6 Mar. 2018 is named CBI019-14 ST25 copy.txt and is 9 KB in size.

TECHNICAL FIELD

The present disclosure relates generally to engineered nucleic-acid targeting nucleic acids and nucleoprotein complexes comprising one or more Cas proteins and one or more engineered nucleic-acid targeting nucleic acids. The disclosure also relates to compositions and methods for making and using the engineered nucleic-acid targeting nucleic acids and nucleoprotein complexes of the present invention.

BACKGROUND

Clustered regularly interspaced short palindromic repeats (CRISPR) and CRISPR-associated proteins (Cas) constitute the CRISPR-Cas system. The CRISPR-Cas system provides adaptive immunity against foreign DNA in bacteria (see, e.g., Barrangou, R., et al., Science 315:1709-1712 (2007); Makarova, K. S., et al., Nature Reviews Microbiology 9:467-477 (2011); Garneau, J. E., et al., Nature 468:67-71 (2010); Sapranauskas, R., et al., Nucleic Acids Research 39:9275-9282 (2011)).

CRISPR-Cas systems have recently been reclassified into two classes, comprising five types and sixteen subtypes (see Makarova, K., et al., Nature Reviews Microbiology 13:1-15 (2015)). This classification is based upon identifying all cas genes in a CRISPR-Cas locus and determining the signature genes in each CRISPR-Cas locus, ultimately determining that the CRISPR-Cas systems can be placed in either Class 1 or Class 2 based upon the genes encoding the effector module, i.e., the proteins involved in the interference stage. Recently a sixth CRISPR-Cas system (Type VI) has been identified (see Abudayyeh O., et al., Science 353(6299): aaf5573 (2016)). Certain bacteria possess more than one type of CRISPR-Cas system.

Class 1 systems have a multi-subunit crRNA-effector complex, whereas Class 2 systems have a single protein, such as Cas9, Cpf1, C2c1, C2c2, C2c3, or a crRNA-effector complex. Class 1 systems comprise Type I, Type III, and Type IV systems. Class 2 systems comprise Type II and Type V systems.

Type II systems have cas1, cas2, and cas9 genes. The cas9 gene encodes a multi-domain protein that combines the functions of the crRNA-effector complex with DNA target sequence cleavage. Type II systems also encode a tracrRNA. Type II systems are further divided into three subtypes, subtypes II-A, II-B, and II-C. Subtype II-A contains an additional gene, csn2. Examples of organisms with a subtype II-A systems include, but are not limited to, *Streptococcus pyogenes*, *Streptococcus thermophilus*, and *Staphylococcus aureus*. Subtype II-B lacks csn2, but has cas4. An example of an organism with a subtype II-B system is *Legionella pneumophila*. Subtype II-C is the most common Type II system found in bacteria and has only three proteins, Cas1, Cas2, and Cas9. An example of an organism with a subtype II-C system is *Neisseria lactamica*.

Type V systems have a cpf1 gene and cas1 and cas2 genes (see Zetsche, B., et al., Cell 163:1-13 (2015)). The cpf1 gene encodes a protein, Cpf1, that has a RuvC-like nuclease domain that is homologous to the respective domain of Cas9, but lacks the HNH nuclease domain that is present in Cas9 proteins. Type V systems have been identified in several bacteria including, but not limited to, *Parcubacteria bacterium*, *Lachnospiraceae bacterium*, *Butyrivibrio proteoclasticus*, *Peregrinibacteria bacterium*, *Acidaminococcus* spp., *Porphyromonas macacae*, *Porphyromonas crevioricanis*, *Prevotella disiens*, *Moraxella bovoculi*, *Smithella* spp., *Leptospira inadai*, *Franciscella tularensis*, *Franciscella novicida*, *Candidatus methanoplasma termitum*, and *Eubacterium eligens*. Recently it has been demonstrated that Cpf1 also has RNase activity, and it is responsible for pre-crRNA processing (see Fonfara, I., et al., Nature 532(7600):517-521 (2016)).

In Class 2 systems, the crRNA is associated with a single protein and achieves interference by combining nuclease activity with RNA-binding domains and base-pair formation between the crRNA and a nucleic acid target sequence.

In Type II systems, nucleic acid target sequence binding involves Cas9 and the crRNA, as does the nucleic acid target sequence cleavage. In Type II systems, the RuvC-like nuclease (RNase H fold) domain and the HNH (McrA-like) nuclease domain of Cas9 each cleave one of the strands of the double-stranded nucleic acid target sequence. The Cas9 cleavage activity of Type II systems also requires hybridization of crRNA to tracrRNA to form a duplex that facilitates the crRNA and nucleic acid target sequence binding by the Cas9.

In Type V systems, nucleic acid target sequence binding involves Cpf1 and the crRNA, as does the nucleic acid target sequence cleavage. In Type V systems, the RuvC-like nuclease domain of Cpf1 cleaves one strand of the double-stranded nucleic acid target sequence, and a putative nuclease domain cleaves the other strand of the double-stranded nucleic acid target sequence in a staggered configuration, producing 5' overhangs, which is in contrast to the blunt ends generated by Cas9 cleavage. These 5' overhangs may facilitate insertion of DNA.

The Cpf1 cleavage activity of Type V systems also does not require hybridization of crRNA to tracrRNA to form a duplex, rather the crRNA of Type V systems uses a single crRNA that has a stem-loop structure forming an internal duplex. Cpf1 binds the crRNA in a sequence and structure specific manner that recognizes the stem loop and sequences adjacent to the stem loop, most notably the nucleotide 5' of the spacer sequences that hybridizes to the nucleic acid target sequence. This stem-loop structure is typically in the range of 15 to 19 nucleotides in length. Substitutions that disrupt this stem-loop duplex abolish cleavage activity, whereas other substitutions that do not disrupt the stem-loop duplex do not abolish cleavage activity. In Type V systems, the crRNA forms a stem-loop structure at the 5' end, and the sequence at the 3' end is complementary to a sequence in a nucleic acid target sequence.

Other proteins associated with Type V crRNA and nucleic acid target sequence binding and cleavage include Class 2 candidate 1 (C2c1) and Class 2 candidate 3 (C2c3). C2c1 and C2c3 proteins are similar in length to Cas9 and Cpf1 proteins, ranging from approximately 1,100 amino acids to approximately 1,500 amino acids. C2c1 and C2c3 proteins also contain RuvC-like nuclease domains and have an architecture similar to Cpf1. C2c1 proteins are similar to Cas9 proteins in requiring a crRNA and a tracrRNA for nucleic acid target sequence binding and cleavage but have an optimal cleavage temperature of 50° C. C2c1 proteins target an AT-rich protospacer adjacent motif (PAM), which similar to the PAM of Cpf1, is 5' of the nucleic acid target sequence (see, e.g., Shmakov, S., et al., Molecular Cell 60(3):385-397 (2015)).

Class 2 candidate 2 (C2c2) does not share sequence similarity to other CRISPR effector proteins and was recently identified as a Type VI system (see Abudayyeh, O., et al., Science 353(6299):aaf5573 (2016)). C2c2 proteins have two HEPN domains and demonstrate single-stranded RNA-cleavage activity. C2c2 proteins are similar to Cpf1 proteins in requiring a crRNA for nucleic acid target sequence binding and cleavage, although not requiring tracr-RNA. Also similar to Cpf1, the crRNA for C2c2 proteins forms a stable hairpin, or stem-loop structure, that aids in association with the C2c2 protein. Type VI is a single polypeptide RNA endonuclease that utilizes a single crRNA to direct site specific cleavage. Additionally, after hybridizing to the target RNA complementary to the spacer, C2c2 becomes a promiscuous RNA endonuclease exhibiting non-specific endonuclease activity toward any single-stranded RNA in a sequence independent manner (see East-Seletsky, A., et al., Nature 538(7624):270-273 (2016)).

Regarding Class 2 Type II CRISPR-Cas systems, a large number of Cas9 orthologs are known in the art as well as their associated polynucleotide components (tracrRNA and crRNA) (see, e.g., Fonfara, I., et al., Nucleic Acids Research 42(4):2577-2590 (2014), including all Supplemental Data; Chylinski K., et al., Nucleic Acids Research 42(10):6091-6105 (2014), including all Supplemental Data). In addition, Cas9-like synthetic proteins are known in the art (see U.S. Published Patent Application No. 2014-0315985, published 23 Oct. 2014).

Cas9 is an exemplary Type II CRISPR Cas protein. Cas9 is an endonuclease that can be programmed by the tracr-RNA/crRNA to cleave, site-specifically, a DNA target sequence using two distinct endonuclease domains (HNH and RuvC/RNase H-like domains) (see U.S. Published Patent Application No. 2014-0068797, published 6 Mar. 2014; see also Jinek M., et al., Science 337:816-821 (2012)).

Typically, each wild-type CRISPR-Cas9 system includes a crRNA and a tracrRNA. The crRNA has a region of complementarity to a potential DNA target sequence and a second region that forms base-pair hydrogen bonds with the tracrRNA to form a secondary structure, typically to form at least a stem structure. The region of complementarity to the DNA target sequence is the spacer. The tracrRNA and a crRNA interact through a number of base-pair hydrogen bonds to form secondary RNA structures. Complex formation between tracrRNA/crRNA and Cas9 protein results in conformational change of the Cas9 protein that facilitates binding to DNA, endonuclease activities of the Cas9 protein, and crRNA-guided site-specific DNA cleavage by the endonuclease Cas9. For a Cas9 protein/tracrRNA/crRNA complex to cleave a double-stranded DNA target sequence, the DNA target sequence is adjacent to a cognate PAM. By engineering a crRNA to have an appropriate spacer sequence, the complex can be targeted to cleave at a locus of interest, e.g., a locus at which sequence modification is desired.

Ran, F. A., et al., Nature 520(7546):186-191 (2015), including all extended data, present the crRNA/tracrRNA sequences and secondary structures of eight Type II CRISPR-Cas systems (see Extended Data FIG. 1 of Ran, F. A., et al.). Predicted tracrRNA structures were based on the Constraint Generation RNA folding model (Zuker, M., Nucleic Acids Research 31:3406-3415 (2003)). Furthermore, Fonfara, et al., Nucleic Acids Research 42(4):2577-2590 (2014), including all Supplemental Data (in particular Supplemental Figure S11) present the crRNA/tracrRNA sequences and secondary structures of eight Type II CRISPR-Cas systems. RNA duplex secondary structures were predicted using RNAcofold of the Vienna RNA package (Bernhart, S. H., et al., Algorithms for Molecular Biology 1(1):3 (2006); Hofacker, I. L., et al., Journal of Molecular Biology 319:1059-1066 (2002)) and RNAhybrid (bibiserv.techfak.uni-bielefeld.de/rnahybrid/). The structure predictions were visualized using VARNA (Darty, K., et al., Bioinformatics 25:1974-1975 (2009)). Fonfara, et al., show that the crRNA/tracrRNA complex for *Campylobacter jejuni* does not have the bulge region; however, it retains a stem structure located 3' of the spacer that is followed in the 3' direction with another stem structure.

Naturally occurring Type V CRISPR-Cas systems, unlike Type II CRISPR Cas systems, do not require a tracrRNA for crRNA maturation and cleavage of a nucleic acid target sequence. In a typical structure of a Type V CRISPR crRNA, the DNA target binding sequence is downstream of a specific secondary structure (i.e., a stem-loop structure) that interacts with the Cpf1 protein. The bases 5' of the stem loop adopt a pseudo-knot structure further stabilizing the stem-loop structure with non-canonical Watson-Crick base pairing, triplex interaction, and reverse Hoogsteen base pairing (see Yamano, T., et al., Cell 165(4):949-962 (2016)).

The spacer of Class 2 CRISPR-Cas systems can hybridize to a nucleic acid target sequence that is located 5' or 3' of a PAM, depending upon the Cas protein to be used. A PAM can vary depending upon the Cas polypeptide to be used. For example, if Cas9 from *S. pyogenes* is used, the PAM can be a sequence in the nucleic acid target sequence that comprises the sequence 5'-NRR-3', wherein R can be either A or G, wherein N is any nucleotide, and N is immediately 3' of the nucleic acid target sequence targeted by the nucleic acid target binding sequence. A Cas protein may be modified such that a PAM may be different compared with a PAM for an unmodified Cas protein. For example, if Cas9 from *S. pyogenes* is used, the Cas9 protein may be modified such that the PAM no longer comprises the sequence 5'-NRR-3', but instead comprises the sequence 5'-NNR-3', wherein R can be either A or G, wherein N is any nucleotide, and N is immediately 3' of the nucleic acid target sequence targeted by the nucleic acid target sequence.

Other Cas proteins recognize other PAMs, and one of skill in the art is able to determine the PAM for any particular Cas protein. For example, Cpf1 has a thymine-rich PAM site that targets, for example, a TTTN sequence (see Fagerlund, R., et al., Genome Biology 16:251 (2015)).

The RNA-guided Cas9 endonuclease has been widely used for programmable genome editing in a variety of organisms and model systems (see, e.g., Jinek M., et al., Science 337:816-821 (2012); Jinek M., et al., eLife 2:e00471. doi: 10.7554/eLife.00471 (2013); U.S. Published Patent Application No. 2014-0068797, published 6 Mar. 2014).

Genome engineering includes altering the genome by deleting, inserting, mutating, or substituting specific nucleic acid sequences. The alteration can be gene- or location-specific. Genome engineering can use site-directed nucleases, such as Cas proteins and their cognate polynucleotides, to cut DNA, thereby generating a site for alteration. In certain cases, the cleavage can introduce a double-strand break (DSB) in the DNA target sequence. DSBs can be repaired, e.g., by non-homologous end joining (NHEJ), microhomology-mediated end joining (MMEJ), or homology-directed repair (HDR). HDR relies on the presence of a template for repair. In some examples of genome engineering, a donor polynucleotide or portion thereof can be inserted into the break.

SUMMARY OF THE INVENTION

The present invention relates generally to engineered cross-type-nucleic-acid targeting nucleic acids.

In one aspect the present invention relates to an engineered CRISPR Class 2 cross-type-nucleic-acid targeting nucleic acid ("CRISPR Class 2 cross-type-NATNA"), comprising: a Cpf1-associated nucleic-acid targeting nucleic acid, having a 5' end and a 3' end, comprising a spacer element ("Cpf1-NATNA"); a first Cas9-associated nucleic-acid targeting nucleic acid, having a 5' end and a 3' end, comprising a spacer element ("first Cas9-NATNA"); and a second Cas9-associated nucleic-acid targeting nucleic acid, having a 5' end and a 3' end, comprising a tracr element ("second Cas9-NATNA"); wherein the first Cas9-NATNA or the second Cas9-NATNA is connected with the Cpf1-NATNA. In one embodiment, the first Cas9-NATNA or the second Cas9-NATNA is non-covalently connected with the Cpf1-NATNA, for example, through hydrogen base-pair bonding at the 5' end or 3' end of the first Cas9-NATNA or through hydrogen base-pair bonding at the 5' end or 3' end of the second Cas9-NATNA. In an alternative embodiment, the first Cas9-NATNA or the second Cas9-NATNA is covalently connected with the Cpf1-NATNA, for example, the Cpf1-NATNA is covalently connected with the 5' end or the 3' end of the first Cas9-NATNA or to the 5' end or the 3' end of the second Cas9-NATNA.

In some embodiments, the Cpf1-NATNA of the CRISPR Class 2 cross-type-NATNA is capable forming a first complex with a Cpf1 protein ("Cas9-Cpf1-NATNA/Cpf1 protein complex"), and the first Cas9-NATNA of the CRISPR Class 2 cross-type-NATNA and the second Cas9-NATNA of the CRISPR Class 2 cross-type-NATNA are capable of forming a second complex with a Cas9 protein ("Cas9-Cpf1-NATNA/Cas9 protein complex"). If the Cpf1-NATNA forms the first complex with the Cpf1 protein ("Cpf1-NATNA/Cpf1 protein complex"), the first complex is capable of binding a first double-stranded nucleic acid target sequence complementary to the Cpf1 spacer element. Furthermore, if the first Cas9-NATNA and the second Cas9-NATNA form the second complex with the Cas9 protein ("Cas9-NATNA/Cas9 protein complex"), the second complex is capable of binding a second double-stranded nucleic acid target sequence complementary to the first Cas9-NATNA spacer element. In other embodiments, if the first complex is formed and the second complex is formed, resulting in a Cas9-Cpf1-NATNA/Cas9&Cpf1 protein complex, the Cas9-Cpf1-NATNA/Cas9&Cpf1 protein complex is capable of binding a first double-stranded nucleic acid target sequence complementary to the Cpf1 spacer element and a second double-stranded nucleic acid target sequence complementary to the first Cas9-NATNA spacer element.

In further embodiments, one or more of the Cpf1-NATNA, the first Cas9-NATNA, and the second Cas9-NATNA can further comprise a linker element nucleotide sequence covalently connected with the 5' end or the 3' end of the one or more of the Cpf1-NATNA, the first Cas9-NATNA, and the second Cas9-NATNA. Furthermore, a first linker element nucleotide sequence and a second linker element nucleotide sequence can be covalently connected with both the 5' and 3' ends of one or more of the Cpf1-NATNA, the first Cas9-NATNA, and the second Cas9-NATNA.

Embodiments of the present invention also include the engineered CRISPR Class 2 cross-type-NATNA, wherein the 3' end of the first Cas9-NATNA is covalently connected through a loop element with the 5' end of the second Cas9-NATNA. The covalent connection results in a single-Cas9-associated nucleic-acid targeting nucleic acid ("single-Cas9-NATNA"), having a 5' end and a 3' end. The single-Cas9-NATNA comprises the first Cas9-NATNA and the second Cas9-NATNA. In some embodiments, the single-Cas9-NATNA is non-covalently connected with the Cpf1-NATNA through hydrogen base-pair bonding at the 5' end or the 3' end. Furthermore, a first Cpf1-NATNA and a second Cpf1-NATNA can be non-covalently connected with both the 5' and 3' ends of the single-Cas9-NATNA. In other embodiments, the single-Cas9-NATNA is covalently connected with the Cpf1-NATNA. Additionally, a first Cpf1-NATNA and a second Cpf1-NATNA can be covalently connected with both the 5' and 3' ends of the single-Cas9-NATNA.

In further embodiments, one or both of the Cpf1-NATNA and the single-Cas9-NATNA can further comprise a linker element nucleotide sequence covalently connected with the 5' end or the 3' end. Furthermore, a first linker element nucleotide sequence and a second linker element nucleotide sequence can be covalently connected with both the 5' and 3' ends of one or both of the Cpf1-NATNA and the single-Cas9-NATNA.

In some embodiment, one or more of the Cpf1-NATNA, the first Cas9-NATNA, and the second Cas9-NATNA (including the single-Cas9-NATNA comprising the first Cas9-NATNA and the second Cas9-NATNA) of the engineered CRISPR Class 2 cross-type-NATNA can comprise RNA, DNA, or combinations of RNA and DNA.

In a further aspect, the present invention includes a nucleic acid/protein composition comprising an engineered CRISPR Class 2 cross-type-NATNA, a Cas9 protein, and a Cpf1 protein. In some embodiments, the engineered CRISPR Class 2 cross-type-NATNA is in a complex with the Cas9 protein and the Cpf1 protein. In additional embodiments, one or both of the Cpf1 protein and the Cas9 protein can be enzymatically inactive. When the Cpf1 protein is enzymatically inactive (dCpf1 protein) or the Cas9 protein is enzymatically inactive (dCas9 protein), the nucleic acid/ protein composition can further comprises a donor polynucleotide non-covalently connected with the dCpf1 protein or the dCas9 protein.

In another aspect, the present invention relates to an expression vector, comprising one or more nucleic acid sequences encoding an engineered CRISPR Class 2 cross-type-NATNA.

In yet another aspect, the present invention includes a recombinant cell, comprising one or more nucleic acid sequences encoding an engineered CRISPR Class 2 cross-type-NATNA.

An additional aspect of the present invention includes a kit comprising an engineered CRISPR Class 2 cross-type-NATNA and a buffer, or one or more nucleic acid sequences encoding an engineered CRISPR Class 2 cross-type-NATNA and a buffer. Kits can further comprise a Cas9 protein, a Cpf1 protein, or both a Cas9 protein and a Cpf1 protein. Furthermore, kits can comprise one or more nucleic acid sequences encoding a Cas9 protein, a Cpf1 protein, or both a Cas9 protein and a Cpf1 protein.

Further aspects of the present invention include methods of using an engineered CRISPR Class 2 cross-type-NATNA, as described herein. One method is a method of binding DNA. The method comprises contacting a first DNA target sequence in the DNA and a second DNA target sequence in the DNA with a nucleic acid/protein composition comprising an engineered CRISPR Class 2 cross-type-NATNA, a Cas9 protein, and a Cpf1 protein; thereby facilitating binding of the nucleic acid/protein composition to the first DNA target sequence in the DNA and the second DNA target sequence in the DNA. The Cpf1-NATNA spacer element of the CRISPR Class 2 cross-type-NATNA is complementary to the first DNA target sequence, and the Cas9-NATNA spacer of the CRISPR Class 2 cross-type-NATNA is complementary to the second DNA target sequence.

Another method of the present invention is a method of cutting DNA. The method comprises contacting a first DNA target sequence in the DNA and a second DNA target sequence in the DNA with a nucleic acid/protein composition comprising an engineered CRISPR Class 2 cross-type-NATNA, a Cas9 protein, and a Cpf1 protein; thereby facilitating binding of the nucleic acid/protein composition to the first DNA target sequence and the second DNA target sequence resulting in cutting of the first DNA target sequence and the second DNA target sequence. The Cpf1-NATNA spacer element of the CRISPR Class 2 cross-type-NATNA is complementary to the first DNA target sequence, and the Cas9-NATNA spacer of the CRISPR Class 2 cross-type-NATNA is complementary to the second DNA target sequence. Furthermore, the Cpf1 protein of the bound nucleic acid/protein composition is capable of cutting the first DNA target sequence and the Cas9 protein of the bound nucleic acid/protein composition is capable of cutting the second DNA target sequence.

These aspects and other embodiments of the present invention using the engineered Class 2 CRISPR-Cas systems of the present invention will be readily apparent to those of ordinary skill in the art in view of the disclosure herein.

BRIEF DESCRIPTION OF THE FIGURES

The figures are not proportionally rendered, nor are they to scale. The locations of indicators are approximate.

FIG. 14A illustrates a wild-type Cpf1-crRNA. FIG. 14B illustrates a wild-type Cpf1 pre-crRNA. FIG. 14C, FIG. 14D and FIG. 14E illustrate modified Cpf1-crRNAs.

INCORPORATION BY REFERENCE

Figure 1A:
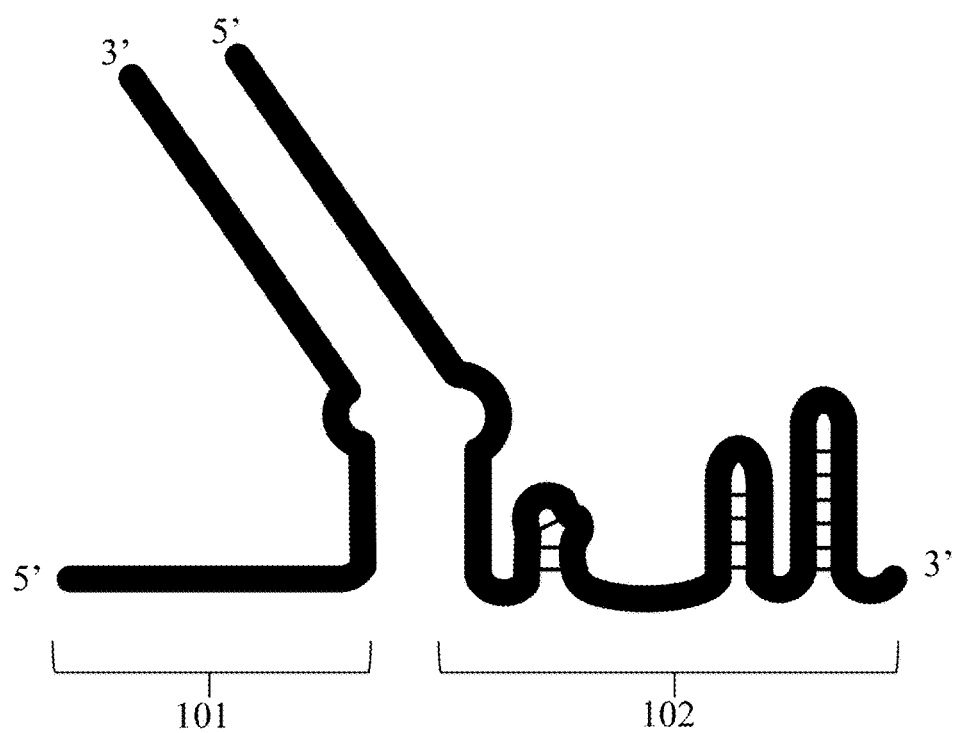
FIG. 1A and FIG. 1B present illustrative examples of dual-guide Class 2 Type II CRISPR-associated guide RNAs.

All patents, publications, and patent applications cited in this specification are herein incorporated by reference as if each individual patent, publication, or patent application was specifically and individually indicated to be incorporated by reference in its entirety for all purposes.

DETAILED DESCRIPTION OF THE INVENTION

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a polynucleotide" includes one or more polynucleotides, and reference to "a vector" includes one or more vectors.

Unless defined otherwise, all technical and scientific terms used herein have the same meaning as commonly understood by one of ordinary skill in the art to which the invention pertains. Although other methods and materials similar, or equivalent, to those described herein can be useful in the present invention, preferred materials and methods are described herein.

In view of the teachings of the present specification, one of ordinary skill in the art can employ conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, Cold Spring Harbor Laboratory Press, ISBN 978-1-936113-81-1 (2014); Culture of Animal Cells: A Manual of Basic Technique and Specialized Applications, 6th Edition, R. I. Freshney, Wiley-Blackwell, ISBN 978-0-470-52812-9 (2010); Transgenic Animal Technology, Third Edition: A Laboratory Handbook, C. A. Pinkert, Elsevier, ISBN 978-0124104907 (2014); The Laboratory Mouse, Second Edition, H. Hedrich, Academic Press, ISBN 978-0123820082 (2012); Manipulating the Mouse Embryo: A Laboratory Manual, R. Behringer, et al., Cold Spring Harbor Laboratory Press, ISBN 978-1936113019 (2013); PCR 2: A Practical Approach, M. J. McPherson, et al., IRL Press, ISBN 978-0199634248 (1995); Methods in Molecular Biology (Series), J. M. Walker, ISSN 1064-3745, Humana Press; RNA: A Laboratory Manual, D. C. Rio, et al., Cold Spring Harbor Laboratory Press, ISBN 978-0879698911 (2010); Methods in Enzymology (Series), Academic Press; Molecular Cloning: A Laboratory Manual (Fourth Edition), M. R. Green, et al., Cold Spring Harbor Laboratory Press, ISBN 978-1605500560 (2012); Bioconjugate Techniques, Third Edition, G. T. Hermanson, Academic Press, ISBN 978-0123822390 (2013); Methods in Plant Biochemistry and Molecular Biology, W. V. Dashek, CRC Press, ISBN 978-0849394805 (1997); Plant Cell Culture Protocols (Methods in Molecular Biology), V. M. Loyola-Vargas, et al., Humana Press, ISBN 978-1617798177 (2012); Plant Transformation Technologies, C. N. Stewart, et al., Wiley-Blackwell, ISBN 978-0813821955 (2011); Recombinant Proteins from Plants (Methods in Biotechnology), C. Cunningham, et al., Humana Press, ISBN 978-1617370212 (2010); Plant Genomics: Methods and Protocols (Methods in Molecular Biology), D. J. Somers, et al., Humana Press, ISBN 978-1588299970 (2009); Plant Biotechnology: Methods in Tissue Culture and Gene Transfer, R. Keshavachandran, et al., Orient Blackswan, ISBN 978-8173716164 (2008).

Clustered regularly interspaced short palindromic repeats (CRISPR) and related CRISPR-associated proteins (Cas proteins) constitute CRISPR-Cas systems (see, e.g., Barrangou, R., et al., Science 315:1709-1712 (2007)).

As used herein, "Cas protein" and "CRISPR-Cas protein" refer to CRISPR-associated proteins (Cas) including, but not limited to Class 1 Type I CRISPR-associated proteins, Class 1 Type III CRISPR-associated proteins, and Class 1 Type IV CRISPR-associated proteins, Class 2 Type II CRISPR-associated proteins, Class 2 Type V CRISPR-associated proteins, and Class 2 Type VI CRISPR-associated proteins. Class 2 Cas proteins include Cas9 proteins, Cas9-like proteins encoded by Cas9 orthologs, Cas9-like synthetic proteins, Cpf1 proteins, proteins encoded by Cpf1 orthologs, Cpf1-like synthetic proteins, C2c1 proteins, C2c2 proteins, C2c3 proteins, and variants and modifications thereof. In some embodiments, Cas proteins are Class 2 CRISPR-associated proteins, for example one or more Class 2 Type II CRISPR-associated proteins, such as Cas9, one or more Class 2 Type V CRISPR-associated proteins, such as Cpf1, and one ore more Class 2 Type VI CRISPR-associated proteins, such as C2c2. In preferred embodiments, Cas proteins are one or more Class 2 Type II CRISPR-associated proteins, such as Cas9, and one or more Class 2 Type V CRISPR-associated proteins, such as Cpf1. Typically, for use in aspects of the present invention, a Cas protein is capable of interacting with one or more cognate polynucleotides (most typically RNA) to form a nucleoprotein complex (most typically, a ribonucleoprotein complex).

"Cas9 protein," as used herein, refers to a Cas9 wild-type protein derived from Class 2 Type II CRISPR-Cas9 systems, modifications of Cas9 proteins, variants of Cas9 proteins, Cas9 orthologs, and combinations thereof. Cas9 proteins include, but not limited to, Cas9 from *Streptococcus pyogenes* (UniProtKB—Q99ZW2 (CAS9_STRP1)), *Streptococcus thermophilus* (UniProtKB—G3ECR1 (CAS9_STRTR)), and *Staphylococcus aureus* (UniProtKB—J7RUA5 (CAS9_STAAU)). Cas9 homologs can be identified using sequence similarity search methods known to one skilled in the art. "dCas9," as used herein, refers to variants of Cas9 protein that are nuclease-deactivated Cas9 proteins, also termed "catalytically inactive Cas9 protein," "enzymatically inactive Cas9," "catalytically dead Cas9" or "dead Cas9." Such molecules lack all or a portion of endonuclease activity and can therefore be used to regulate genes in an RNA-guided manner (see Jinek M., et al., Science 337:816-821 (2012)). This is accomplished by introducing mutations that inactivate Cas9 nuclease function and is typically accomplished by mutating both of the two catalytic residues (D10A in the RuvC-1 domain, and H840A in the HNH domain, numbered relative to *S. pyogenes* Cas9). It is understood that mutation of other catalytic residues to reduce activity of either or both of the nuclease domains can also be carried out by one skilled in the art. The resultant dCas9 is unable to cleave double-stranded DNA but retains the ability to complex with a guide nucleic acid and bind a DNA target sequence. The Cas9 double mutant with changes at amino acid positions D10A and H840A completely inactivates both the nuclease and nickase activities. Targeting specificity is determined by complementary base pairing of guide RNA (typically, a single guide RNA) to the genomic locus and the PAM. Cas9 is the signature protein characteristic for Class 2 Type II CRISPR systems.

"Cpf1 protein," as used herein, refers to a Cpf1 wild-type protein derived from Class 2 Type V CRISPR-Cpf1 systems, modifications of Cpf1 proteins, variants of Cpf1 proteins, Cpf1 orthologs, and combinations thereof. "dCpf1," as used herein, refers to variants of Cpf1 protein that are nuclease-deactivated Cpf1 proteins, also termed "catalytically inactive Cpf1 protein," or "enzymatically inactive Cpf1." Cpf1 proteins include, but not limited to, *Francisella novicida* (UniProtKB—A0Q7Q2 (CPF1_FRATN)), *Lachnospiraceae bacterium* (UniProtKB—A0A182DWE3 (A0A182DWE3_9FIRM)), and *Acidaminococcus* sp. (UniProtKB—U2UMQ6 (CPF1_ACISB)). Cpf1 is the signature protein characteristic for Class 2 Type V CRISPR systems. Cpf1 homologs can be identified using sequence similarity search methods known to one skilled in the art.

"Argonaute protein," as used herein, refers to an Argonaute wild-type protein, modifications of Argonaute proteins, variants of Argonaute proteins, Argonaute orthologs, and combinations thereof (see, e.g., Hall, T., Structure 13:1403-1408 (2005); Hock, J., et al., Genome Biology 9(2): 210-210.8 (2008); Swarts, D., et al., Nature 507(7491):258-261 (2014); Swarts, D., et al., Nature Structural & Molecular Biology (9):743-753 (2014); Hur, J. K., et al., Trends in Biochemical Sciences 39(6):257-259 (2014)). "dArgonaute," as used herein, refers to variants of Argonaute proteins that are nuclease-deactivated Argonaute proteins, also termed "catalytically inactive Argonaute protein," or "enzymatically inactive Argonaute." Argonaute protein refers to a protein from a family of proteins typically defined by the presence of a PIWI domain and/or a PAZ (PIWI-Argonaute-Zwille) domain. An Argonaute protein (e.g., a eukaryotic Argonaute or prokaryotic Argonaute) typically is capable of interacting with an Argonaute guide (i.e., a nucleic-acid targeting nucleic acid; Ago-NATNA) to form a complex. The Ago-NATNA comprises a nucleic acid target binding sequence. The complex is capable of site-directed binding to a nucleic acid target sequence. The complex is targeted to the nucleic acid target sequence by the nucleic acid target binding sequence of the Ago-NATNA. The nucleic acid target sequences to which an Argonaute protein/ Ago-NATNA complex binds can be, for example, RNA, DNA, or hybrids of RNA/DNA. Argonaute protein homologs can be identified using sequence similarity search methods known to one skilled in the art.

By "nucleic-acid targeting nucleic acid" (NATNA) is meant one or more polynucleotides that guide a protein, such as an Argonaute protein or more preferably a Cas protein (e.g., a Cas9 protein, a dCas9 protein, a Cpf1 protein, or a dCpf1 protein) to preferentially bind a nucleic acid target sequence, typically, a double-stranded nucleic acid target sequence. For example, embodiments of the present invention include, but are not limited to, engineered NATNAs comprising a Cas9-associated nucleic-acid targeting nucleic acid and a Cpf1-associated nucleic-acid targeting nucleic acid. Examples of these NATNAs include, but are not limited to the following: a Cas9-associated nucleic-acid targeting nucleic acid comprising a spacer element ("first Cas9-NATNA"; e.g., FIG. 1A, 101) and a Cas9-associated nucleic-acid targeting nucleic acid comprising a tracr element ("second Cas9-NATNA"; e.g., FIG. 1A, 102); a "single-Cas9-NATNA" (see, e.g., FIG. 2) comprising a first Cas9-NATNA and a second Cas9-NATNA; and a Cpf1-associated nucleic-acid targeting nucleic acid comprising a spacer element ("Cpf1-NATNA") (see, e.g., FIG. 3). Examples of Cas9-Cpf1-NATNAs of one aspect of the present invention include, but are not limited to, those illustrated in FIG. 3, FIG. 4, FIG. 5A, FIG. 5B, FIG. 6, FIG. 7, FIG. 8, FIG. 9, and FIG. 10. NATNAs can comprise ribonucleotide bases (e.g., RNA), deoxyribonucleotide bases (e.g., DNA), combinations of ribonucleotide bases and deoxyribonucleotide bases (e.g., RNA/DNA), nucleotides, nucleotide analogs, modified nucleotides, and the like, as well as synthetic, naturally occurring, and non-naturally occurring modified backbone residues or linkages, for example, as described herein.

Figure 1B:
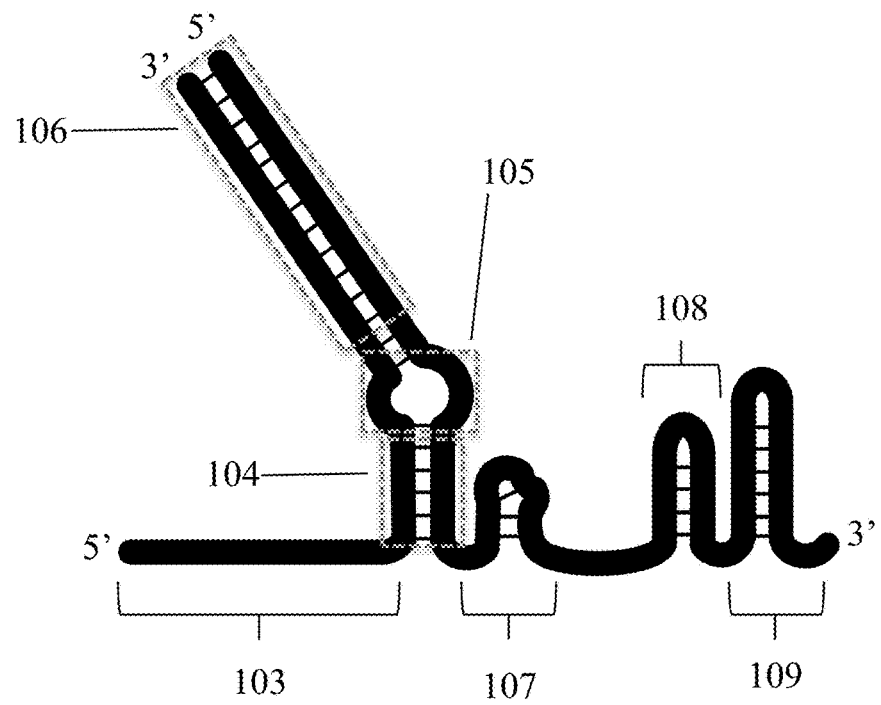

As used herein, "dual-guide RNA" and "Cas9-dual-guide RNA" typically refer to a two-component RNA system for a polynucleotide component capable of associating with a cognate Cas9 protein. FIG. 1A and FIG. 1B present illustrative examples of dual-guide Class 2 Type II CRISPR-Cas9-associated RNAs. FIG. 1A shows a two-RNA component Type II CRISPR-Cas9 system comprising a Cas9-crRNA (FIG. 1A, 101) and a Cas9-tracrRNA (FIG. 1A, 102). FIG. 1B illustrates the formation of base-pair hydrogen bonds between the Cas9-crRNA and the Cas9-tracrRNA to form secondary structure (see U.S. Published Patent Application No. 2014-0068797, published 6 Mar. 2014; see also Jinek M., et al., Science 337:816-21 (2012)). FIG. 1B presents an overview of and nomenclature for secondary structural elements of the Cas9-crRNA and Cas9-tracrRNA of the *S. pyogenes* Cas9 including the following: a spacer element (FIG. 1B, 103); a first stem element comprising a lower stem element (FIG. 1B, 104), a bulge element comprising unpaired nucleotides (FIG. 1B, 105), and an upper stem element (FIG. 1B, 106); a nexus element (FIG. 1B, 107); a first 3' hairpin element (FIG. 1B, 108); and a second 3' hairpin element (FIG. 1B, 109). A Cas9-dual-guide RNA is capable of forming a nucleoprotein complex with a cognate Cas9 protein, wherein the complex is capable of targeting a nucleic acid target sequence complementary to the spacer sequence. Modifications of Cas9-dual guides are known in the art, including, deletion of one or more 3' hairpin elements (FIG. 1B, 108, 109) and modifications of the upper stem, bulge, and lower stem (FIG. 1B, 106, 105, 104, respectively) (see, e.g., U.S. Patent Publication No. 2014-0315985, published 23 Oct. 2014; U.S. Patent Publication No. 2015-0376586, published 31 Dec. 2015).

Figure 2:
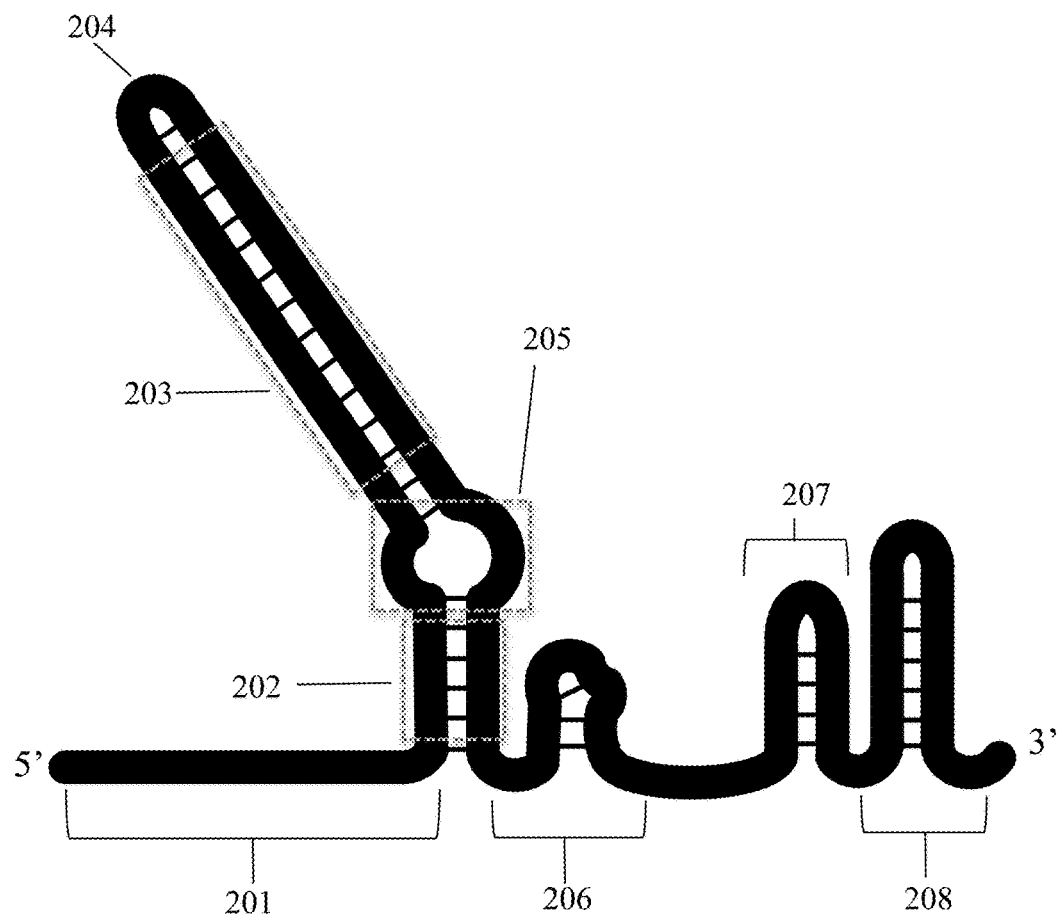
FIG. 2 presents an illustrative example of single-guide Class 2 Type II CRISPR-associated guide RNA.

As used herein, "single-guide RNA" (sgRNA) and "Cas9-sgRNA" typically refer to a one-component RNA system for a polynucleotide component capable of associating with a cognate Cas9 protein. FIG. 2 shows an example of a Class 2 Type II CRISPR-Cas9-associated sgRNA. The figure illustrates a Cas9 single-guide RNA (Cas9-sgRNA) wherein the Cas9-crRNA is covalently joined to the Cas9-tracrRNA and forms a RNA polynucleotide secondary structure through base-pair hydrogen bonding (see, e.g., U.S. Published Patent Application No. 2014-0068797, published 6 Mar. 2014). FIG. 2 presents an overview of and nomenclature for secondary structural elements of a Cas9-sgRNA for *S. pyogenes* including the following: a spacer element (FIG. 2, 201); a first stem element comprising a lower stem element (FIG. 2, 202), a bulge element comprising unpaired nucleotides (FIG. 2, 205), and an upper stem element (FIG. 2, 203); a loop element (FIG. 2, 204) comprising unpaired nucleotides; a nexus element (FIG. 2, 206); a first 3' hairpin element (FIG. 2, 207); and a second 3' hairpin element (FIG. 2, 208). (See, e.g., FIGS. 1 and 3 of Briner, A. E., et al., Molecular Cell 56(2):333-339 (2014).) A Cas9-sgRNA is capable of forming a nucleoprotein complex with a cognate Cas9 protein, wherein the complex is capable of targeting a nucleic acid sequence complementary to the spacer sequence. Modifications of Cas9-single guides are known in the art, including, deletion of one or more 3' hairpin elements (FIG. 2, 207, 208) and modifications of the upper stem, bulge, and lower stem (FIG. 2, 203, 205, 202, respectively) (see, e.g., U.S. Patent Publication No. 2014-0315985, published 23 Oct. 2014; U.S. Patent Publication No. 2015-0376586, published 31 Dec. 2015).

Figure 3:
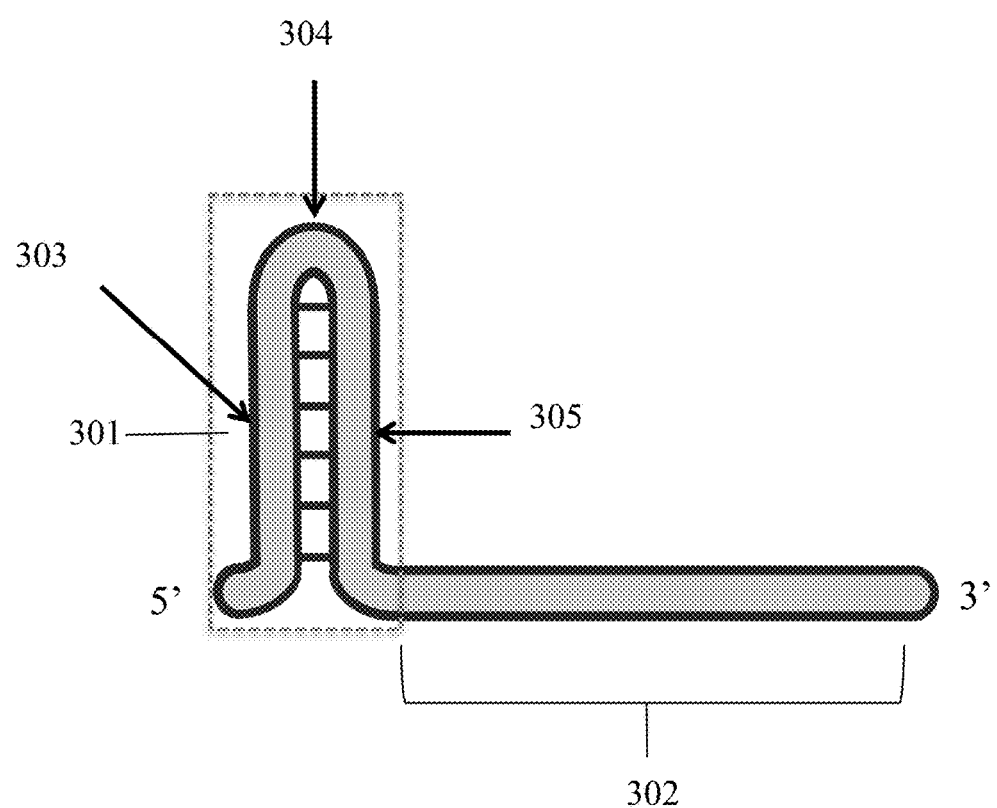
FIG. 3 presents an illustrative example of a Class 2 Type V crRNA guide RNA.

"Guide crRNA" and "Cpf1-crRNA," as used herein, typically refer to a one-component RNA system for a polynucleotide component capable of associating with a cognate Cpf1 protein. FIG. 3 presents an example of a Type V CRISPR-Cpf1-associated RNA (Cpf1-crRNA) (see, e.g., Zetsche, B., et al., Cell 163:1-13 (2015)). FIG. 3 presents an overview of and nomenclature for secondary structural elements of a Cpf1-crRNA as follows: a stem-loop element (FIG. 3, 301) and a spacer element (FIG. 3, 302). The stem-loop element comprises, in a 5' to 3' direction, a Cpf1-stem RNA sequence 1 (FIG. 3, 303), a loop element (FIG. 3, 304), and a complementary Cpf1-stem RNA sequence 2 (FIG. 3, 305), wherein the Cpf1-stem RNA sequence 1 and the complementary Cpf1-stem RNA sequence 2 form a duplex. A guide crRNA is capable of forming a nucleoprotein complex with a cognate Cpf1 protein, wherein the complex is capable of targeting a nucleic acid target sequence complementary to the spacer sequence.

As used herein, a "cross-type-nucleic-acid targeting nucleic acid" and a "cross-type-NATNA" are used interchangeably to refer to a first NATNA connected with a second NATNA. For example, a CRISPR Class 2 cross-type-NATNA refers to one or more polynucleotides typically comprising a CRISPR Class 2 Type V NATNA (e.g., FIG. 3) connected with a CRISPR Class 2 Type II NATNA (e.g., FIG. 1A, FIG. 1B, FIG. 2). The types of connections, between the first NATNA and the second NATNA, to form a cross-type-NATNA include, for example, covalent linkage (e.g., FIG. 4), hydrogen bonding (e.g., FIG. 5A, FIG. 5B), ligand/ligand binding moiety pairing, and/or cross-linking. Covalent linkages include, but are not limited to, phosphodiester bonds. A cross-type-NATNA is capable of forming a complex with a first protein that is capable of forming a complex with the first NATNA and a second protein that is capable of forming a complex with the second NATNA. For example, a CRISPR Class 2 cross-type-NATNA is capable of forming a complex with a Class 2 Type V Cas protein (e.g., a Cpf1 protein) that is capable of forming a complex with the CRISPR Class 2 Type V NATNA and Class 2 Type II Cas protein (e.g., a Cas9 protein) that is capable of forming a complex with the CRISPR Class 2 Type II NATNA. In this embodiment, a complex formed between the Cpf1-NATNA and a Cpf1 protein is capable of binding a first double-stranded nucleic acid target sequence. Also, and a complex formed between the Cas9-NATNA (e.g., a first Cas9-associated nucleic-acid targeting nucleic acid comprising a spacer element, "first Cas9-NATNA," and a second Cas9-associated nucleic-acid targeting nucleic acid comprising a tracr element, "second Cas9-NATNA, or a single-Cas9-NATNA) and a Cas9 protein is capable of binding a second double-stranded nucleic acid target sequence (e.g., FIG. 11B). In another embodiment, a cross-type-NATNA comprises an Ago-NATNA and a Class 2 Type V NATNA or a Class 2 Type II NATNA.

As used herein, a "cross-link" is a bond that links one polymer chain (e.g., a polynucleotide or polypeptide) to another. Such bonds can be covalent bonds or ionic bonds. For example, one polynucleotide can be bound to another polynucleotide by cross-linking the polynucleotides.

As used herein, the term "cognate" typically refers to a Cas protein and one or more Cas polynucleotides that are capable of forming a nucleoprotein complex capable of site-directed binding to a nucleic acid target sequence complementary to the nucleic acid target binding sequence present in one of the Cas polynucleotides.

As used herein, "complementarity" refers to the ability of a nucleic acid sequence to form hydrogen bond(s) with another nucleic acid sequence (e.g., through traditional Watson-Crick base pairing). A percent complementarity indicates the percentage of residues in a nucleic acid molecule that can form hydrogen bonds with a second nucleic acid sequence. If two polynucleotide sequences have 100% complementarity, the two sequences are perfectly complementary, i.e., all of the contiguous residues of a first polynucleotide hydrogen bond with the same number of contiguous residues in a second polynucleotide.

"Covalent bond," "covalently attached," "covalently bound," "covalently linked," "covalently connected," and "molecular bond" are used interchangeably herein, and refer to a chemical bond that involves the sharing of electron pairs between atoms. Examples of covalent bonds include, but are not limited to, phosphodiester bonds and phosphorothioate bonds.

"Non-covalent bond," "non-covalently attached," "non-covalently bound," "non-covalently linked," "non-covalent interaction," and "non-covalently connected" are used interchangeably herein, and refer to any relatively weak chemical bond that does not involve sharing of a pair of electrons. Multiple non-covalent bonds often stabilize the conformation of macromolecules and mediate specific interactions between molecules. Examples of non-covalent bonds include, but are not limited to hydrogen bonding (e.g., a Watson-Crick-type hydrogen-bonded base pair, and a Hoogsteen base pair), ionic interactions (e.g., $Na^+Cl^-$), van der Waals interactions, and hydrophobic bonds.

"Connect," "connected," and "connecting" are used interchangeably herein, and refer to a covalent bond or a non-covalent bond between two macromolecules (e.g., polynucleotides, proteins, and the like).

As used herein, "binding" refers to a non-covalent interaction between macromolecules (e.g., between a protein and a polynucleotide, between a polynucleotide and a polynucleotide, and between a protein and a protein, and the like). Such non-covalent interaction is also referred to as "associating" or "interacting" (e.g., if a first macromolecule interacts with a second macromolecule, the first macromolecule binds to second macromolecule in a non-covalent manner). Some portions of a binding interaction may be sequence-specific (the terms "sequence-specific binding," "sequence-specifically bind," "site-specific binding," and "site-specifically binds" are used interchangeably herein). Sequence-specific binding, as used herein, typically refers to one or more NATNAs capable of forming a complex with a protein (e.g., a Cas protein or an Argonaute protein) to cause the protein to bind a first nucleic acid sequence (e.g., a first DNA sequence) comprising a first nucleic acid target sequence (e.g., a first DNA target sequence) preferentially relative to a second nucleic acid sequence (e.g., a second DNA sequence) without the nucleic acid target binding sequence (e.g., the first DNA target binding sequence). All components of a binding interaction do not need to be sequence-specific, such as contacts of a protein with phosphate residues in a DNA backbone. Binding interactions can be characterized by a dissociation constant (Kd). "Affinity" refers to the strength of binding. An increased binding affinity is correlated with a lower Kd.

As used herein, a Cas protein (e.g., a Cas9 protein or Cpf1 protein) is said to "target" a polynucleotide if a Cas protein/NATNA nucleoprotein complex binds or cleaves a polynucleotide at the nucleic acid target sequence within the polynucleotide. An Argonaute protein is said to target a polynucleotide if an Argonaute protein/NATNA nucleoprotein complex binds or cleaves a polynucleotide at the nucleic acid target sequence within the polynucleotide.

As used herein, "double-strand break" (DSB) refers to both strands of a double-stranded segment of DNA being severed. In some instances, if such a break occurs, one strand can be said to have a "sticky end" wherein nucleotides are exposed and not hydrogen bonded to nucleotides on the other strand. In other instances, a "blunt end" can occur wherein both strands remain fully base paired with each other despite the DSB.

"Donor polynucleotide," "donor oligonucleotide," and "donor template" are used interchangeably herein and can be a double-strand polynucleotide (e.g., DNA), a single-stranded polynucleotide (e.g., DNA oligonucleotides), or a combination thereof. Donor polynucleotides comprise homology arms flanking the insertion sequence (e.g., DSBs in the DNA). The homology arms on each side can vary in length. Parameters for the design and construction of donor polynucleotides are well-known in the art (see, e.g., Ran, F., et al., Nature Protocols 8(11):2281-2308 (2013); Smithies, O., et al., Nature 317:230-234 (1985); Thomas, K., et al., Cell 44:419-428 (1986); Wu, S., et al., Nature Protocols 3:1056-1076 (2008); Singer, B., et al., Cell 31:25-33 (1982); Shen, P., et al., Genetics 112:441-457 (1986); Watt, V., et al., Proceedings of the National Academy of Sciences of the United States of America 82:4768-4772 (1985), Sugawara, N., et al., Journal of Molecular Cell Biology 12(2):563-575 (1992); Rubnitz, J., et al., Journal of Molecular Cell Biology 4(11):2253-2258 (1984); Ayares, D., et al., Proceedings of the National Academy of Sciences of the United States of America 83(14):5199-5203 (1986); Liskay, R, et al., Genetics 115(1):161-167 (1987)).

As used herein, "homology-directed repair" (HDR) refers to DNA repair that takes place in cells, for example, during repair of a DSB in DNA. HDR requires nucleotide sequence homology and uses a donor polynucleotide to repair the sequence wherein the DSB (e.g., within a DNA target sequence) occurred. The donor polynucleotide generally has the requisite sequence homology with the sequence flanking the DSB so that the donor polynucleotide can serve as a suitable template for repair. HDR results in the transfer of genetic information from, for example, the donor polynucleotide to the DNA target sequence. HDR may result in alteration of the DNA target sequence (e.g., insertion, deletion, mutation) if the donor polynucleotide sequence differs from the DNA target sequence and part or all of the donor polynucleotide is incorporated into the DNA target sequence. In some embodiments, an entire donor polynucleotide, a portion of the donor polynucleotide, or a copy of the donor polynucleotide is integrated at the site of the DNA target sequence. For example, a donor polynucleotide can be used for repair of the break in the DNA target sequence, wherein the repair results in the transfer of genetic information (i.e., polynucleotide sequences) from the donor polynucleotide at the site or in close proximity of the break in the DNA. Accordingly, new genetic information (i.e., polynucleotide sequences) may be inserted or copied at a DNA target sequence.

A "genomic region" is a segment of a chromosome in the genome of a host cell that is present on either side of the nucleic acid target sequence site or, alternatively, also includes a portion of the nucleic acid target sequence site. The homology arms of the donor polynucleotide have sufficient homology to undergo homologous recombination with the corresponding genomic regions. In some embodiments, the homology arms of the donor polynucleotide share significant sequence homology to the genomic region immediately flanking the nucleic acid target sequence site; it is recognized that the homology arms can be designed to have sufficient homology to genomic regions farther from the nucleic acid target sequence site.

As used herein, "non-homologous end joining" (NHEJ) refers to the repair of a DSB in DNA by direct ligation of one end of the break to the other end of the break without a requirement for a donor polynucleotide. NHEJ is a DNA repair pathway available to cells to repair DNA without the use of a repair template. NHEJ in the absence of a donor polynucleotide often results in nucleotides being randomly inserted or deleted at the site of the DSB.

"Microhomology-mediated end joining" (MMEJ) is pathway for repairing a DSB in DNA. MMEJ involves deletions flanking a DSB and alignment of microhomologous sequences internal to the broken ends before joining. MMEJ is genetically defined and requires the activity of, for example, CtIP, Poly(ADP-Ribose) Polymerase 1 (PARP1), DNA polymerase theta (Pol θ), DNA Ligase 1 (Lig 1), DNA Ligase 3 (Lig 3). Additional genetic components are known in the art (see, e.g., Sfeir, A., et al., Trends in Biochemical Sciences 40:701-714 (2015)).

As used herein, "DNA repair" encompasses any process whereby cellular machinery repairs damage to a DNA molecule contained in the cell. The damage repaired can include single-strand breaks or double-strand breaks. At least three mechanisms exist to repair DSBs: HDR, NHEJ, and MMEJ. "DNA repair" is also used herein to refer to DNA repair resulting from human manipulation, wherein a target locus is modified, e.g., by inserting, deleting, substituting nucleotides, all of which represent forms of genome editing.

As used herein, "recombination" refers to a process of exchange of genetic information between two polynucleotides.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, transcription start sites, repressor binding sequences, stem-loop structures, translational initiation sequences, internal ribosome entry sites (IRES), translation leader sequences, transcription termination sequences (e.g., polyadenylation signals and poly-U sequences), translation termination sequences, primer binding sites, and the like.

Regulatory elements include those that direct constitutive, inducible, and repressible expression of a nucleotide sequence in many types of host cells and those that direct expression of the nucleotide sequence only in certain host cells (e.g., tissue-specific regulatory sequences). In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer; see, e.g., Boshart et al., Cell 41:521-530 (1985)), the SV40 promoter, the dihydrofolate reductase promoter, the β-actin promoter, the phosphoglycerol kinase (PGK) promoter, and the EF1α promoter. It will be appreciated by those skilled in the art that the design of an expression vector can depend on such factors as the choice of the host cell to be transformed, the level of expression desired, and the like. A vector can be introduced into host cells to thereby produce transcripts, proteins, or peptides, including fusion proteins or peptides, encoded by nucleic acids as described herein.

"Gene," as used herein, refers to a polynucleotide sequence comprising exon(s) and related regulatory sequences. A gene may further comprise intron(s) and/or untranslated region(s) (UTR).

As used herein, the term "operably linked" refers to polynucleotide sequences or amino acid sequences placed into a functional relationship with one another. For example, regulatory sequences (e.g., a promoter or enhancer) are "operably linked" to a polynucleotide encoding a gene product if the regulatory sequences regulate or contribute to the modulation of the transcription of the polynucleotide. Operably linked regulatory elements are typically contiguous with the coding sequence. However, enhancers can function if separated from a promoter by up to several kilobases or more. Accordingly, some regulatory elements may be operably linked to a polynucleotide sequence but not contiguous with the polynucleotide sequence. Similarly, translational regulatory elements contribute to the modulation of protein expression from a polynucleotide.

As used herein, "expression" refers to transcription of a polynucleotide from a DNA template, resulting in, for example, a messenger RNA (mRNA) or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product(s)." Expression may include splicing the mRNA in a eukaryotic cell, if the polynucleotide is derived from genomic DNA.

As used herein, the term "modulate" refers to a change in the quantity, degree or amount of a function. For example, a Cas9 protein/Cpf1 protein/Cas9-Cpf1-NATNA complex, as disclosed herein, may modulate the activity of a promoter sequence by binding to two nucleic acid target sequences at or near the promoter. Depending on the action occurring after binding, the Cas9 protein/Cpf1 protein/Cas9-Cpf1-NATNA complex can induce, enhance, suppress, or inhibit transcription of a gene operatively linked to the promoter sequence. Thus, "modulation" of gene expression includes both gene activation and gene repression.

Modulation can be assayed by determining any characteristic directly or indirectly affected by the expression of the target gene. Such characteristics include, e.g., changes in RNA or protein levels, protein activity, product levels, expression of the gene, or activity level of reporter genes. Accordingly, the terms "modulating expression," "inhibiting expression," and "activating expression" of a gene can refer to the ability of a Cas9 protein/Cpf1 protein/Cas9-Cpf1-NATNA complex to change, activate, or inhibit transcription of a gene.

"Vector" and "plasmid," as used herein, refer to a polynucleotide vehicle to introduce genetic material into a cell. Vectors can be linear or circular. Vectors can contain a replication sequence capable of effecting replication of the vector in a suitable host cell (i.e., an origin of replication). Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art. The four major types of vectors are plasmids, viral vectors, cosmids, and artificial chromosomes. Typically, vectors comprise an origin of replication, a multicloning site, and/or a selectable marker. An expression vector typically comprises an expression cassette.

As used herein, "expression cassette" refers to a polynucleotide construct generated using recombinant methods or by synthetic means and comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in a vector to form an expression vector.

As used herein, a "targeting vector" is a recombinant DNA construct typically comprising tailored DNA arms, homologous to genomic DNA, that flank elements of a target gene or nucleic acid target sequence (e.g., a DSB). A targeting vector comprises a donor polynucleotide. Elements of the target gene can be modified in a number of ways including deletions and/or insertions. A defective target gene can be replaced by a functional target gene, or in the alternative a functional gene can be knocked out. Optionally, the donor polynucleotide of a targeting vector comprises a selection cassette comprising a selectable marker that is introduced into the target gene. Targeting regions (i.e., nucleic acid target sequences) adjacent or within a target gene can be used to affect regulation of gene expression.

As used herein, the terms "nucleic acid," "nucleotide sequence," "oligonucleotide," and "polynucleotide" are interchangeable and refer to a polymeric form of nucleotides. The nucleotides may be deoxyribonucleotides (DNA), ribonucleotides (RNA), analogs thereof, or combinations thereof, and may be of any length. Polynucleotides may perform any function and may have any secondary and tertiary structures. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include fluorinated nucleotides, methylated nucleotides, and nucleotide analogs. Nucleotide structure may be modified before or after a polymer is assembled. Following polymerization, polynucleotides may be additionally modified via, for example, conjugation with a labeling component or target binding component. A nucleotide sequence may incorporate non-nucleotide components. The terms also encompass nucleic acids comprising modified backbone residues or linkages, that are synthetic, naturally occurring, and non-naturally occurring, and have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), Locked Nucleic Acid (LNA™) (Exiqon, Inc., Woburn, Mass.) nucleosides, glycol nucleic acid, bridged nucleic acids, and morpholino structures.

Peptide-nucleic acids (PNAs) are synthetic homologs of nucleic acids wherein the polynucleotide phosphate-sugar backbone is replaced by a flexible pseudo-peptide polymer. Nucleobases are linked to the polymer. PNAs have the capacity to hybridize with high affinity and specificity to complementary sequences of RNA and DNA.

In phosphorothioate nucleic acids, the phosphorothioate (PS) bond substitutes a sulfur atom for a non-bridging oxygen in the polynucleotide phosphate backbone. This modification makes the internucleotide linkage resistant to nuclease degradation. In some embodiments, phosphorothioate bonds are introduced between the last 3 to 5 nucleotides at the 5' or 3' end of a polynucleotide sequence to inhibit exonuclease degradation. Placement of phosphorothioate bonds throughout an entire oligonucleotide helps reduce degradation by endonucleases as well.

Threose nucleic acid (TNA) is an artificial genetic polymer. The backbone structure of TNA comprises repeating threose sugars linked by phosphodiester bonds. TNA polymers are resistant to nuclease degradation. TNA can self-assemble by base-pair hydrogen bonding into duplex structures.

Linkage inversions can be introduced into polynucleotides through use of "reversed phosphoramidites" (see, e.g., www.ucalgary.ca/dnalab/synthesis/-modifications/linkages). Typically, such polynucleotides have phosphoramidite groups on the 5'-OH position and a dimethoxytrityl (DMT) protecting group on the 3'-OH position. Normally, the DMT protecting group is on the 5'-OH and the phosphoramidite is on the 3'-OH. The most common use of linkage inversion is to add a 3'-3' linkage to the end of a polynucleotide with a phosphorothioate backbone. The 3'-3' linkage stabilizes the polynucleotide to exonuclease degradation by creating an oligonucleotide having two 5'-OH ends and no 3'-OH end.

Polynucleotide sequences are displayed herein in the conventional 5' to 3' orientation unless otherwise indicated.

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., BLAST, CS-BLAST, FASTA, HMMER, L-ALIGN, and the like) available through the worldwide web at sites including but not limited to GENBANK (www.ncbi.nlm.nih.gov/genbank/) and EMBL-EBI (www.ebi.ac.uk.). Sequence identity between two polynucleotides or two polypeptide sequences is generally calculated using the standard default parameters of the various methods or computer programs. A high degree of sequence identity, as used herein, between two polynucleotides or two polypeptides is typically between about 90% identity and 100% identity, for example, about 90% identity or higher, preferably about 95% identity or higher, more preferably about 98% identity or higher. A moderate degree of sequence identity, as used herein, between two polynucleotides or two polypeptides is typically between about 80% identity to about 85% identity, for example, about 80% identity or higher, preferably about 85% identity. A low degree of sequence identity, as used herein, between two polynucleotides or two polypeptides is typically between about 50% identity and 75% identity, for example, about 50% identity, preferably about 60% identity, more preferably about 75% identity. For example, a Cas protein (e.g., a Cas9 comprising amino acid substitutions or a Cpf1 comprising amino acid substitutions) can have a moderate degree of sequence identity, or preferably a high degree of sequence identity, over its length to a reference Cas protein (e.g., a wild-type Cas9 or a wild-type Cpf1, respectively). As another example, a NATNA can have a moderate degree of sequence identity, or preferably a high degree of sequence identity, over its length compared to a reference wild-type polynucleotide that complexes with the reference Cas protein (e.g., an sgRNA that forms a complex with Cas9 or a crRNA that forms a complex with Cpf1).

As used herein, "hybridization" or "hybridize" or "hybridizing" is the process of combining two complementary single-stranded DNA or RNA molecules so as to form a single double-stranded molecule (DNA/DNA, DNA/RNA, RNA/RNA) through hydrogen base pairing. Hybridization stringency is typically determined by the hybridization temperature and the salt concentration of the hybridization buffer; e.g., high temperature and low salt provide high stringency hybridization conditions. Examples of salt concentration ranges and temperature ranges for different hybridization conditions are as follows: high stringency, approximately 0.01M to approximately 0.05M salt, hybridization temperature 5'C to 10° C. below $T_m$; moderate stringency, approximately 0.16M to approximately 0.33M salt, hybridization temperature 20° C. to 29° C. below $T_m$; and low stringency, approximately 0.33M to approximately 0.82M salt, hybridization temperature 40° C. to 48° C. below $T_m$. $T_m$, of duplex nucleic acids is calculated by standard methods well-known in the art (see, e.g., Maniatis, T., et al., Molecular Cloning: A Laboratory Manual, Cold Spring Harbor Laboratory Press: New York (1982); Casey, J., et al., Nucleic Acids Research 4:1539-1552 (1977); Bodkin, D. K., et al., Journal of Virological Methods 10(1): 45-52 (1985); Wallace, R. B., et al., Nucleic Acids Research 9(4):879-894 (1981)). Algorithm prediction tools to estimate $T_m$ are also widely available. High stringency conditions for hybridization typically refer to conditions under which a nucleic acid having complementarity to a target sequence predominantly hybridizes with the target sequence, and substantially does not hybridize to non-target sequences. Typically, hybridization conditions are of moderate stringency, preferably high stringency.

As used herein, a "stem-loop structure" or "stem-loop element" refers to a polynucleotide having a secondary structure that includes a region of nucleotides that are known or predicted to form a double-stranded region (the "stem element"), wherein at one end of the double-stranded region each strand of the double-stranded region is linked by a region of predominantly single-stranded nucleotides (the "loop element"). The term "hairpin" element is also used herein to refer to stem-loop structures. Such structures are well known in the art. The base pairing may be exact; however, as is known in the art, a stem element does not require exact base pairing. Thus, the stem element may include one or more base mismatches or non-paired bases.

A "linker element nucleotide sequence" and "linker nucleotide sequence" are used interchangeable herein and typically refer to a sequence of one or more nucleotides covalently attached to a 5' end, a 3' end, or to both the 5' and 3' ends of a first polynucleotide sequence. In some embodiments, the linker element nucleotide sequence is for the purpose of connecting a first polynucleotide to a second polynucleotide.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms may be used to refer to an amino acid polymer that has been modified through, for example, acetylation, disulfide bond formation, glycosylation, lipidation, phosphorylation, pegylation, biotinylation, cross-linking, and/or conjugation (e.g., with a labeling component or ligand). Polypeptide sequences are displayed herein in the conventional N-terminal to C-terminal orientation.

Polypeptides and polynucleotides can be made using routine techniques in the field of molecular biology (see, e.g., standard texts discussed above). Furthermore, essentially any polypeptide or polynucleotide is available from commercial sources.

The terms "fusion protein" and "chimeric protein," as used herein, refer to a single protein created by joining two or more proteins, protein domains, or protein fragments that do not naturally occur together in a single protein. For example, a fusion protein can contain a first domain from a Cas9 and a second domain from a Cpf1 protein, a first domain from a Cas9 or Cpf1 protein and a second domain from an Argonaute protein, a first domain from a Cas9, Cpf1, or Argonaute protein and a second domain from a protein other than Cas9, Cpf1, or Argonaute protein, and so on. The modification to include such domains in fusion protein may confer additional activity on the modified site-directed polypeptides. Such activities can include nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity) that modifies a polypeptide associated with nucleic acid target sequence (e.g., a histone). A fusion protein can also comprise epitope tags (e.g., histidine tags, FLAG® (Sigma Aldrich, St. Louis, Mo.) tags, Myc tags), reporter protein sequences (e.g., glutathione-S-transferase, beta-galactosidase, luciferase, green fluorescent protein, cyan fluorescent protein, yellow fluorescent protein), and/or nucleic acid binding domains (e.g., a DNA binding domain, an RNA binding domain). A fusion protein can also comprise activator domains (e.g., heat shock transcription factors, NFKB activators) or repressor domains (e.g., a KRAB domain). As described by Lupo, A., et al., Current Genomics 14(4): 268-278 (2013), the KRAB domain is a potent transcriptional repression module and is located in the amino-terminal sequence of most C2H2 zinc finger proteins (see, e.g., Margolin, J., et al., Proceedings of the National Academy of Sciences of the United States of America 91:4509-4513 (1994); Witzgall, R., et al., Proceedings of the National Academy of Sciences of the United States of America 91:4514-4518 (1994)). The KRAB domain typically binds to co-repressor proteins and/or transcription factors via protein-protein interactions, causing transcriptional repression of genes to which KRAB zinc finger proteins (KRAB-ZFPs) bind (see, e.g., Friedman J R, et al., Genes & Development 10:2067-2678 (1996)). In some embodiments, linker nucleic acid sequences are used to join the two or more proteins, protein domains, or protein fragments.

As used herein, a "host cell" generally refers to a biological cell. A cell is the basic structural, functional and/or biological unit of a living organism. A cell can originate from any organism having one or more cells. Examples of host cells include, but are not limited to: a prokaryotic cell, eukaryotic cell, a bacterial cell, an archaeal cell, a cell of a single-cell eukaryotic organism, a protozoal cell, a cell from a plant (e.g., cells from plant crops, (such as soy, tomatoes, sugar beets, pumpkin, hay, cannabis, tobacco, plantains, yams, sweet potatoes, cassava, potatoes, wheat, sorghum, soybean, rice, corn, maize, oil-producing *Brassica* (e.g., oil-producing rapeseed and canola), cotton, sugar cane, sunflower, millet, and alfalfa), fruits, vegetables, grains, seeds, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorellapyrenoidosa, Sargassum patens C. agardh*, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, and the like), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, and the like). Furthermore, a cell can be a stem cell or a progenitor cell.

As used herein, "stem cell" refers to a cell that has the capacity for self-renewal, i.e., the ability to go through numerous cycles of cell division while maintaining the undifferentiated state. Stem cells can be totipotent, pluripotent, multipotent, oligopotent, or unipotent. Stem cells can be embryonic, fetal, amniotic, adult, or induced pluripotent stem cells.

As used herein, "induced pluripotent stem cells" refers to a type of pluripotent stem cell that is artificially derived from a non-pluripotent cell, typically an adult somatic cell, by inducing expression of specific genes.

"Plant," as used herein, refers to whole plants, plant organs, plant tissues, germplasm, seeds, plant cells, and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. "Plant organ" refers to plant tissue or a group of tissues that constitute a morphologically and functionally distinct part of a plant.

"Subject," as used herein, refers to any member of the phylum Chordata, including, without limitation, humans and other primates, including non-human primates such as rhesus macaques, chimpanzees and other monkey and ape species; farm animals, such as cattle, sheep, pigs, goats and horses; domestic mammals, such as dogs and cats; laboratory animals, including rabbits, mice, rats and guinea pigs; birds, including domestic, wild, and game birds, such as chickens, turkeys and other gallinaceous birds, ducks, and geese; and the like. The term does not denote a particular age or gender. Thus, adult, young, and newborn individuals are intended to be covered as well as male and female. In some embodiments, a host cell is derived from a subject (e.g., stem cells, progenitor cells, tissue specific cells). In some embodiments, the subject is a non-human subject.

The terms "wild-type," "naturally occurring," and "unmodified" are used herein to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in, and can be isolated from, a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," and "non-naturally occurring" are interchangeable and indicate intentional human manipulation.

As used herein, "transgenic organism" refers to an organism whose genome is genetically modified. The term includes the progeny (any generation) of a transgenic organism, provided that the progeny has the genetic modification.

As used herein, "isolated" can refer to a nucleic acid or polypeptide that, by the human intervention, exists apart from its native environment and is therefore not a product of nature. An isolated nucleic acid or polypeptide can exist in a purified form and/or can exist in a non-native environment such as, for example, in a recombinant cell.

In one aspect, the present invention relates to an engineered cross-type-nucleic-acid targeting nucleic acid ("cross-type-NATNA"). The cross-type-NATNA typically comprises a first NATNA that targets a first protein to site-specifically bind a first nucleic acid target sequence connected with a second NATNA that targets a second protein to site-specifically bind a second nucleic acid target sequence. The connection can be covalent or non-covalent. The first protein preferably comprises one or more catalytically active nuclease domains and/or one or more catalytically inactive nuclease domains. The second protein preferably comprises one or more catalytically active nuclease domains and/or one or more catalytically inactive nuclease domains. In some embodiments, the cross-type-NATNA comprises a first CRISPR Cas-NATNA from a first type of CRISPR Cas system (e.g., a Cas-NATNA that is capable of forming a complex with a Cas protein from a CRISPR Type I, II, III, IV, V, or VI system) connected with a second type of CRISPR Cas-NATNA from a second CRISPR Cas system (e.g., a Cas-NATNA that is capable of forming a complex with a Cas protein from a CRISPR Type I, II, III, IV, V, or VI system different from the first CRISPR Cas system).

In other embodiments, the cross-type-NATNA comprises a first CRISPR Cas-NATNA from a Class 1 CRISPR Cas system (e.g., a Cas-NATNA that is capable of forming a complex with a Cas protein from a CRISPR Type I, III, or IV system) connected with a second CRISPR Cas-NATNA from a CRISPR Class 2 Cas system (e.g., a Cas-NATNA that is capable of forming a complex with a Cas protein from a CRISPR Type II, V, or VI system). In additional embodiments, the cross-type-NATNA comprises a first CRISPR Cas-NATNA from a Class 1 CRISPR Cas system (e.g., a Cas-NATNA that is capable of forming a complex with a Cas protein from a CRISPR Type I, III, or IV system) connected with a different, second CRISPR Cas-NATNA from a CRISPR Class 1 CRISPR Cas system (e.g., a Cas-NATNA that is capable of forming a complex with a Cas protein from a CRISPR Type I, III, or IV system). In further embodiments, a cross-type-NATNA comprises an Ago-NATNA and either a CRISPR Class 1 NATNA or a CRISPR Class 2 NATNA.

A preferred embodiment of the present invention includes an engineered CRISPR Class 2 cross-type-nucleic-acid targeting nucleic acid ("CRISPR Class 2 cross-type-NATNA"), comprising a Cpf1-NATNA, a first Cas9-NATNA, connected with a second Cas9-NATNA, wherein the first Cas9-NATNA or the second Cas9-NATNA connected covalently or non-covalently with the Cpf1-NATNA.

In some embodiments, two different NATNAs are connected covalently to form the cross-type-NATNA. For example, a first Cas9-NATNA or a second Cas9-NATNA is connected covalently with a Cpf1-NATNA, and the Cpf1-NATNA is covalently bound to the 5' end or the 3' end of the first Cas9-NATNA, or the 5' end or the 3' end of the second Cas9-NATNA. In further embodiments, the different NATNAs are covalently joined through a linker element nucleotide sequence. For example, a first Cas9-NATNA or a second Cas9-NATNA is connected covalently with a Cpf1-NATNA through a linker element nucleotide sequence, and the Cpf1-NATNA is covalently bound through the linker element nucleotide sequence to the 5' end or the 3' end of the first Cas9-NATNA, or the 5' end or the 3' end of the second Cas9-NATNA.

Figure 8:
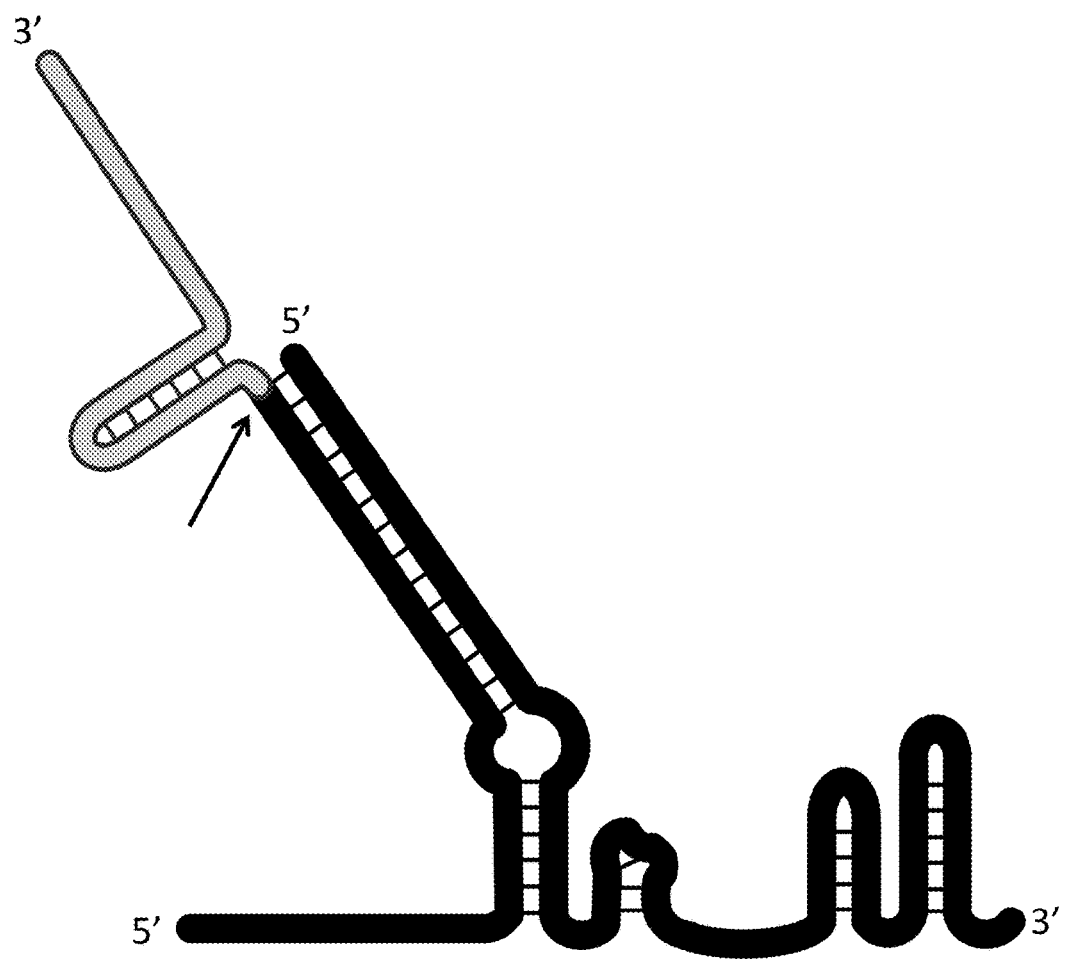
Figure 9:
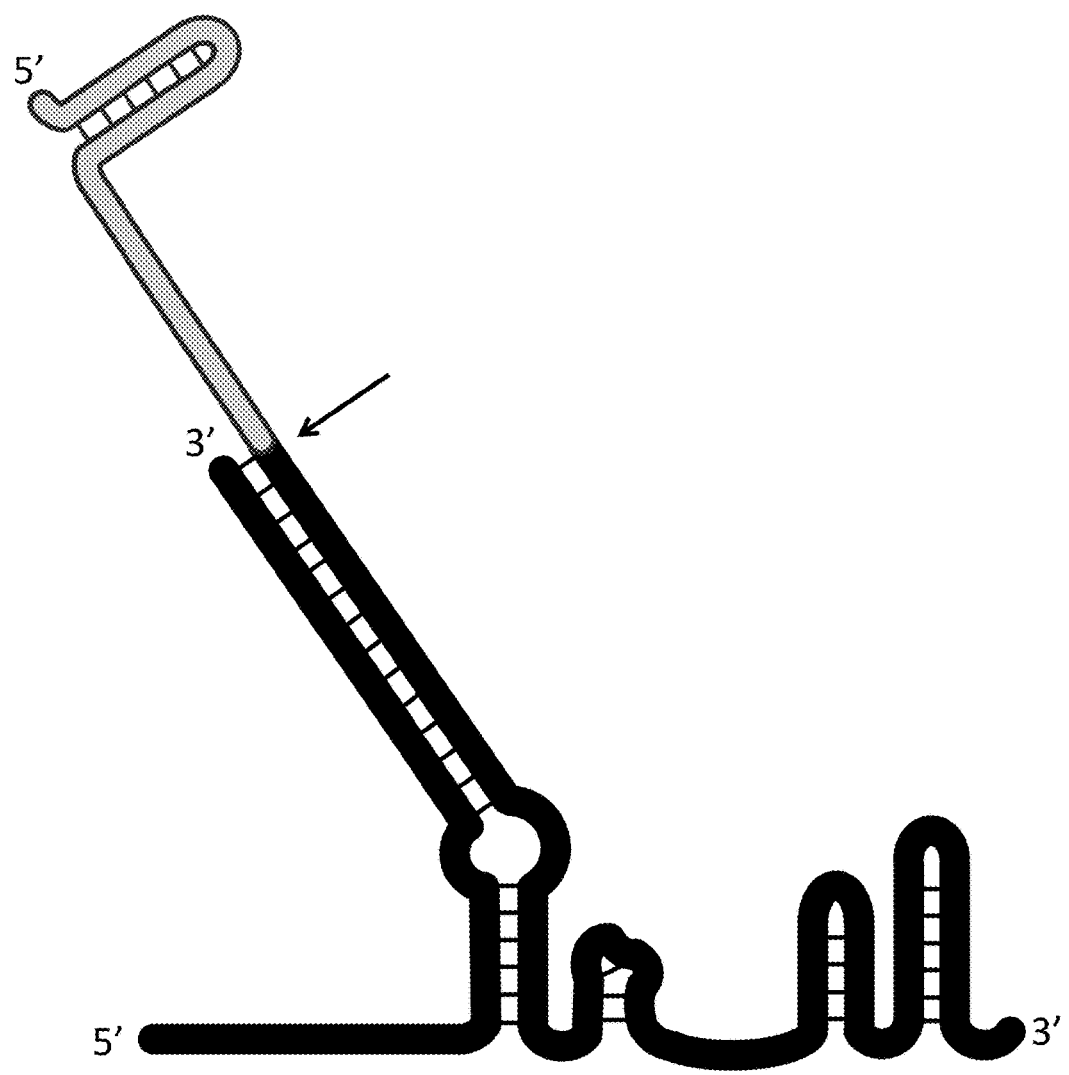
Figure 10:
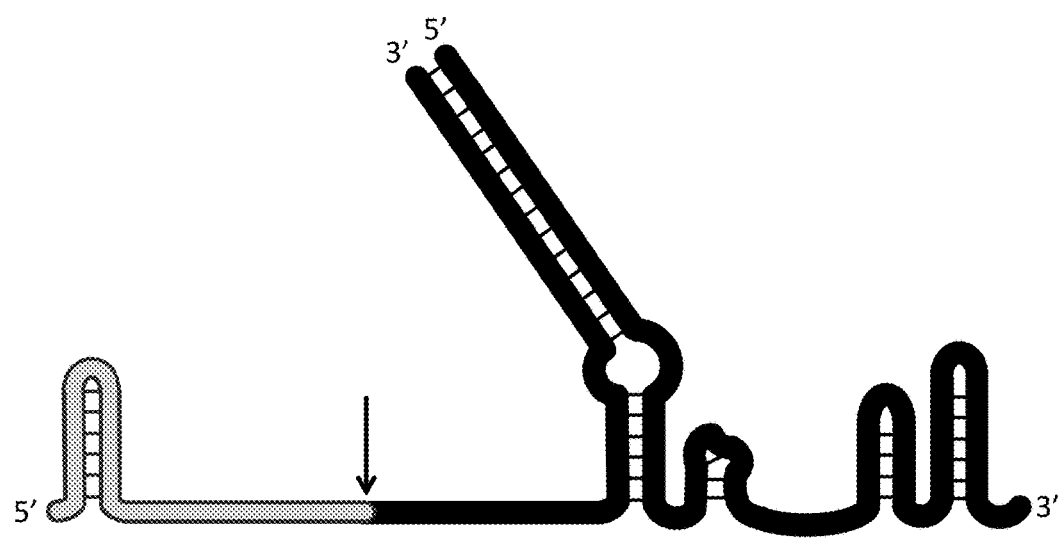

FIG. 8, FIG. 9, and FIG. 10 each illustrate an example of such covalently attachments using RNA NATNAs.

FIG. 8 illustrates an example of an engineered CRISPR Class 2 cross-type-NATNA wherein the 5' end of a Cpf1-crRNA is covalently linked to the 3' end of a Cas9-crRNA. In the figure, the arrow indicates the linkage region between the Cpf1-crRNA and the Cas9-crRNA. The Cpf1-crRNA and the Cas9-crRNA can be directly linked to each other by a covalent bond or, for example, linked to each other through a linker element nucleotide sequence (e.g., 5' end of a Cpf1-crRNA is covalently linked to the 3' end of a linker element nucleotide sequence and the 5' end of the linker element nucleotide sequence is covalently linked to the 3' end of a Cas9-crRNA).

FIG. 9 illustrates an example of an engineered CRISPR Class 2 cross-type-NATNA wherein the 3' end of a Cpf1-crRNA is covalently linked to the 5' end of a Cas9-tracr-RNA. In the figure, the arrow indicates the linkage region between the Cpf1-crRNA and the Cas9-tracrRNA. The Cpf1-crRNA and the Cas9-tracrRNA can be directly linked to each other by a covalent bond or, for example, linked to each other through a linker element nucleotide sequence (e.g., 3' end of a Cpf1-crRNA is covalently linked to the 5' end of a linker element nucleotide sequence and the 3' end of the linker element nucleotide sequence is covalently linked to the 5' end of a Cas9-tracrRNA).

FIG. 10 illustrates an example of an engineered CRISPR Class 2 cross-type-NATNA wherein the 3' end of a Cpf1-crRNA is covalently linked to the 5' end of a Cas9-crRNA. In the figure, the arrow indicates the linkage between the Cpf1-crRNA and the Cas9-crRNA. The Cpf1-crRNA and the Cas9-crRNA can be directly linked to each other by a covalent bond or, for example, linked to each other through a linker element nucleotide sequence (e.g., 3' end of a Cpf1-crRNA is covalently linked to the 5' end of a linker element nucleotide sequence and the 3' end of the linker element nucleotide sequence is covalently linked to the 5' end of a Cas9-crRNA).

In some embodiments, the cross-type-NATNA comprises two different NATNAs, wherein one of the NATNAs comprises more than one polynucleotide (e.g., FIG. 8, FIG. 9, FIG. 10). The NATNA comprising more than one polynucleotide can be covalently linked through a loop element to form a single-NATNA (e.g., compare FIG. 1B, a Cas9-crRNA/Cas9-tracrRNA with FIG. 2, a Cas9-sgRNA).

Figure 4:
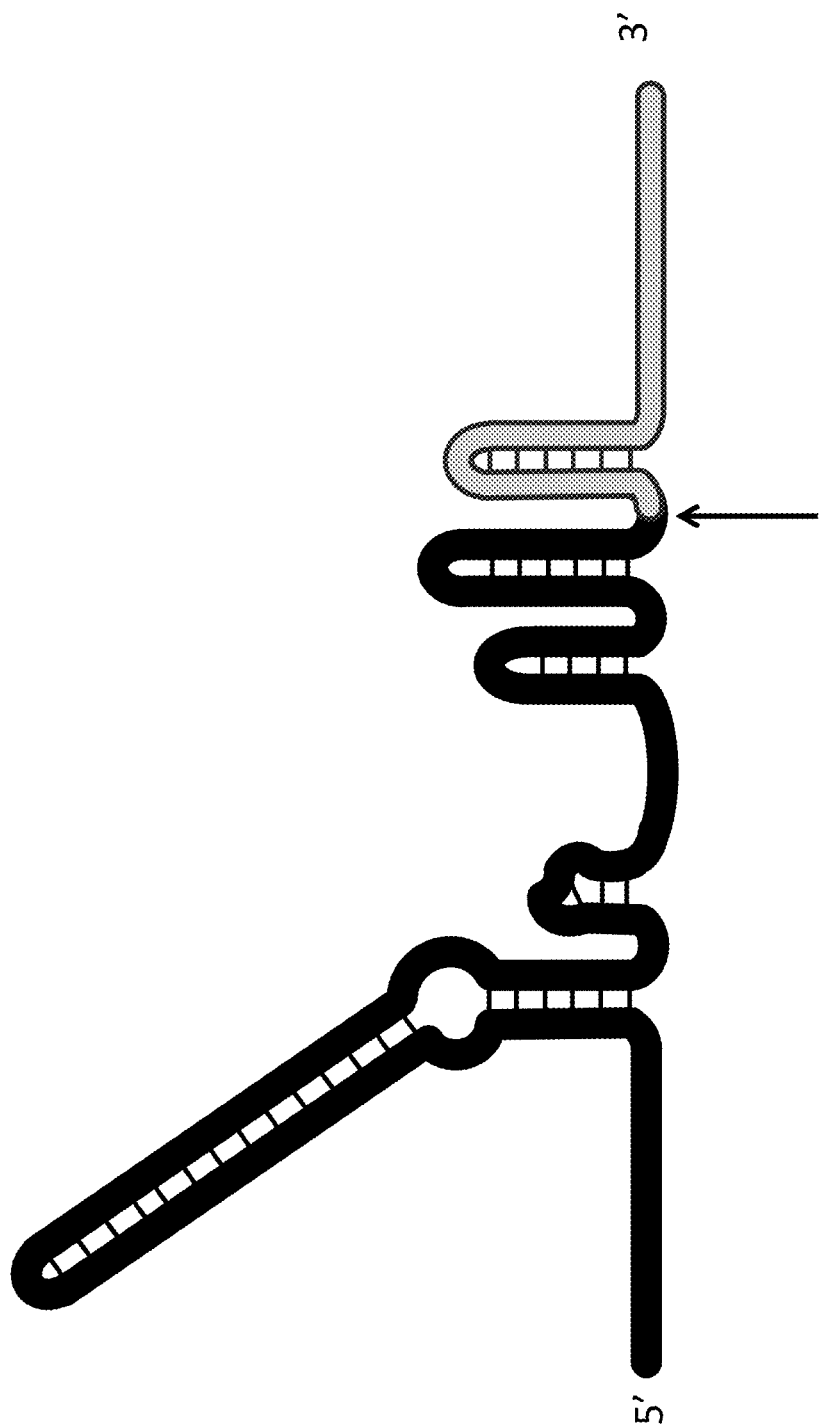
FIG. 4, FIG. 5A, FIG. 5B, FIG. 6, FIG. 7, FIG. 8, FIG. 9, and FIG. 10 present examples of engineered Cas9-Cpf1 nucleic-acid targeting nucleic acids of the present invention.
Figure 6:
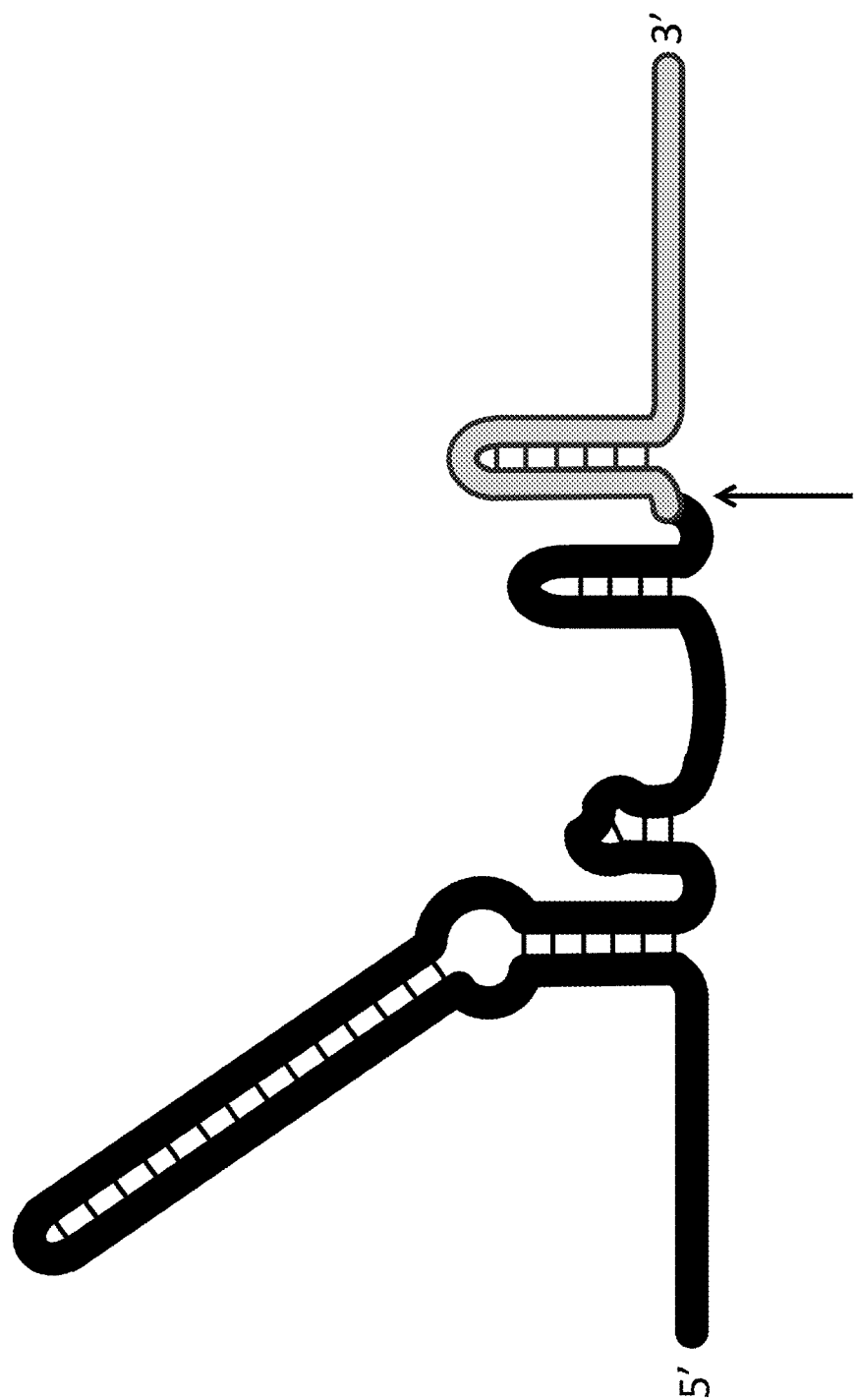
Figure 7:
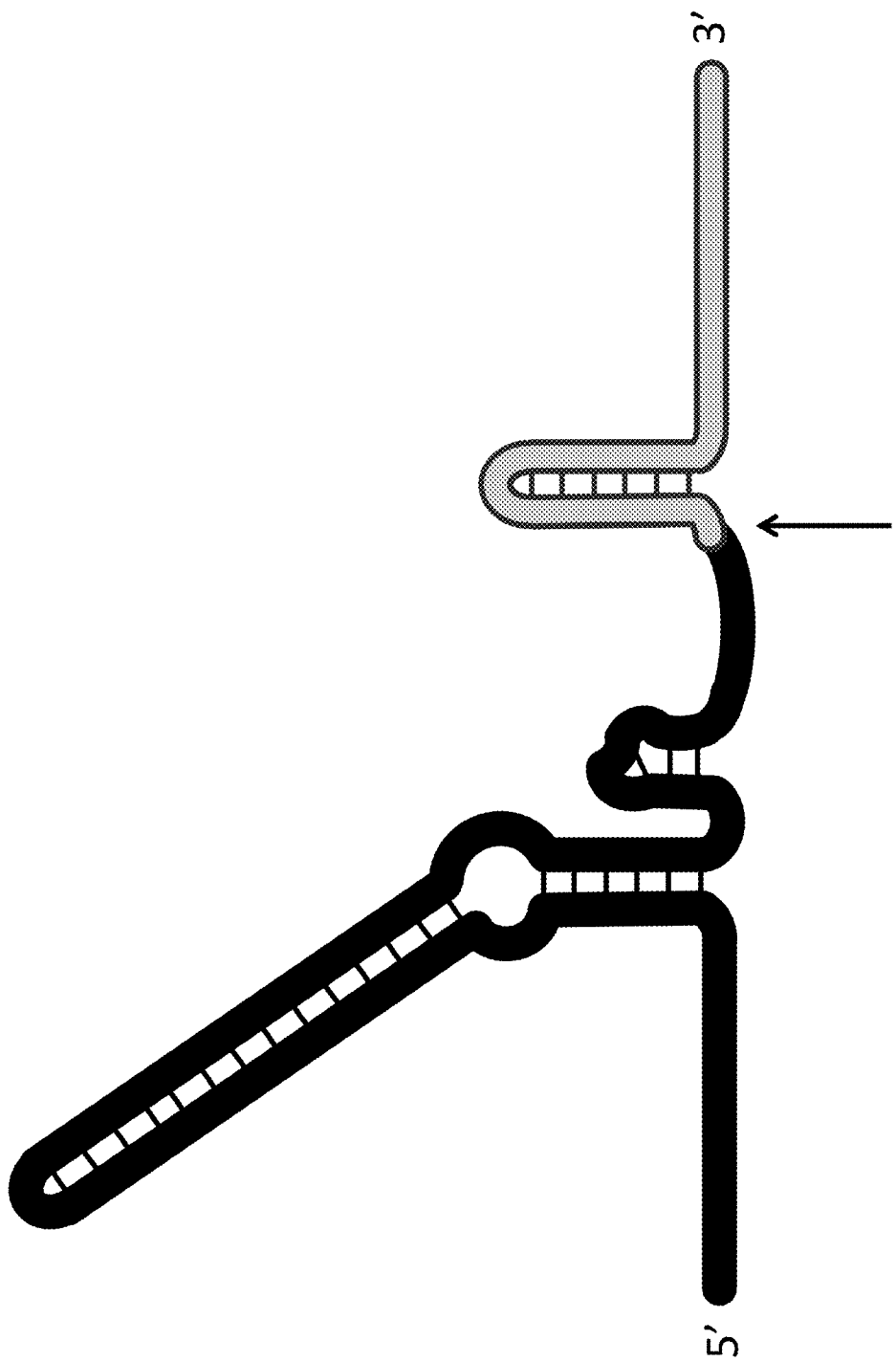

For example, the 3' end of a first Cas9-NATNA can be connected covalently through a loop element with the 5' end of a second Cas9-NATNA forming a single-Cas9-associated nucleic-acid targeting nucleic acid ("single-Cas9-NATNA") having a 5' end and a 3' end. Thus, the single-Cas9-NATNA comprises the first Cas9-NATNA and the second Cas9-NATNA. The single-Cas9-NATNA is covalently attached to a Cpf1-NATNA to form a CRISPR Class 2 cross-type-NATNA. FIG. 4, FIG. 6, and FIG. 7 each illustrate an example of such covalently attachments using RNA NATNAs.

FIG. 4 illustrates an example of an engineered CRISPR Class 2 cross-type-NATNA wherein the 5' end of a Cpf1-crRNA is covalently linked to the 3' end of a Cas9-sgRNA. In the figure, the arrow indicates the linkage region between the Cpf1-crRNA and the Cas9-sgRNA. The Cpf1-crRNA and the Cas9-sgRNA can be directly linked to each other by a covalent bond or, for example, linked to each other through a linker element nucleotide sequence (e.g., 5' end of a Cpf1-crRNA is covalently linked to the 3' end of a linker element nucleotide sequence and the 5' end of the linker element nucleotide sequence is covalently linked to the 3' end of a Cas9-sgRNA).

FIG. 6 illustrates an example of an engineered CRISPR Class 2 cross-type-NATNA wherein the 5' end of a Cpf1-crRNA is covalently linked to the 3' end of a Cas9-sgRNA, and wherein one of the 3' hairpin elements (e.g., FIG. 2, 207, 208) is removed (i.e., deleted) from the Cas9-sgRNA. In the figure, the arrow indicates the linkage region between the Cpf1-crRNA and the Cas9-sgRNA. The Cpf1-crRNA and the Cas9-sgRNA can be directly linked to each other by a covalent bond or, for example, linked to each other through a linker element nucleotide sequence (e.g., 5' end of a Cpf1-crRNA is covalently linked to the 3' end of a linker element nucleotide sequence and the 5' end of the linker element nucleotide sequence is covalently linked to the 3' end of a Cas9-sgRNA, wherein one of the 3' hairpins is removed from the Cas9-sgRNA).

FIG. 7 illustrates an example of an engineered CRISPR Class 2 cross-type-NATNA wherein the 5' end of a Cpf1-crRNA is covalently linked to the 3' end of a Cas9-sgRNA, and wherein both 3' hairpin elements (e.g., FIG. 2, 207, 208) are removed from the Cas9-sgRNA. In the figure, the arrow indicates the linkage region between the Cpf1-crRNA and the Cas9-sgRNA. The Cpf1-crRNA and the Cas9-sgRNA can be directly linked to each other by a covalent bond or, for example, linked to each other through a linker element nucleotide sequence (e.g., 5' end of a Cpf1-crRNA is covalently linked to the 3' end of a linker element nucleotide sequence and the 5' end of the linker element nucleotide sequence is covalently linked to the 3' end of a Cas9-sgRNA, wherein the second hairpin and third hairpin are removed from the Cas9-sgRNA).

As discussed above, in some embodiments, each polynucleotide of each of the two different NATNAs (see, e.g., FIG. 1B, FIG. 2, and FIG. 3) further comprises one or more covalently connected linker elements at the 5' end and/or the 3' end. For example, a Cpf1-NATNA further comprises one or more covalently connected linker elements at the 5' end and/or the 3' end, a first Cas9-NATNA (e.g., a Cas9-crRNA) and/or a second Cas9-NATNA (e.g., a Cas9-tracrRNA) further comprises one or more covalently connected linker elements at the 5' end and/or the 3' end of the first Cas9-NATNA and/or the second Cas9-NATNA, and a single-Cas9-NATNA (e.g., a Cas9-sgRNA) further comprises one or more covalently connected linker elements at the 5' end and/or the 3' end.

In other embodiments, two different NATNAs are connected non-covalently to form the cross-type-NATNA. For example, an engineered CRISPR Class 2 cross-type-NATNA can comprise a first Cas9-NATNA or a second Cas9-NATNA connected non-covalently with a Cpf1-NATNA through hydrogen base-pair bonding at the 5' end or 3' end of the first Cas9-NATNA, or the 5' end or 3' end of the second Cas9-NATNA. In additional embodiments, for non-covalent connection, the different NATNAs are non-covalently connected through one or more linker element sequences.

Figure 5A:
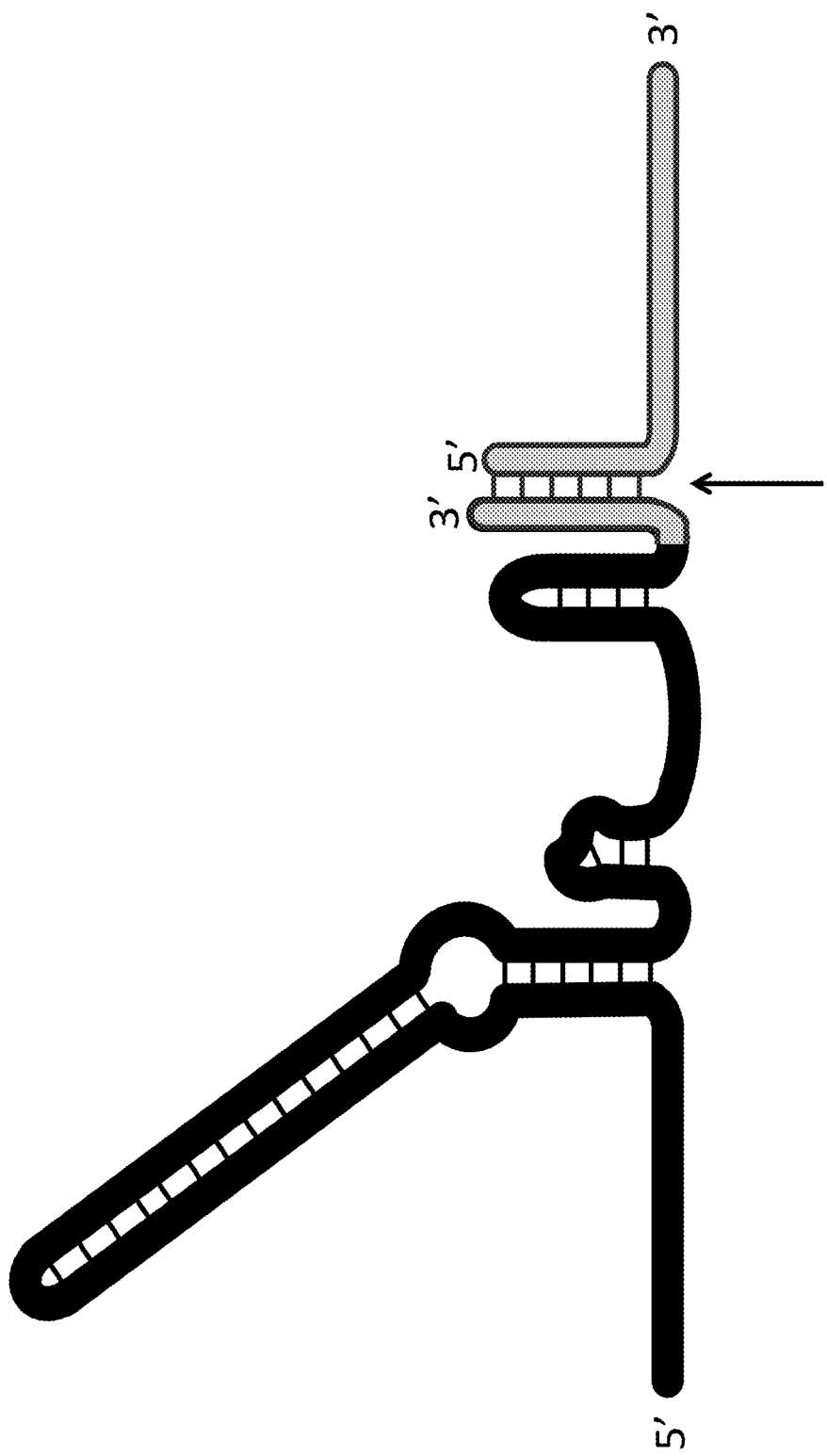
Figure 5B:
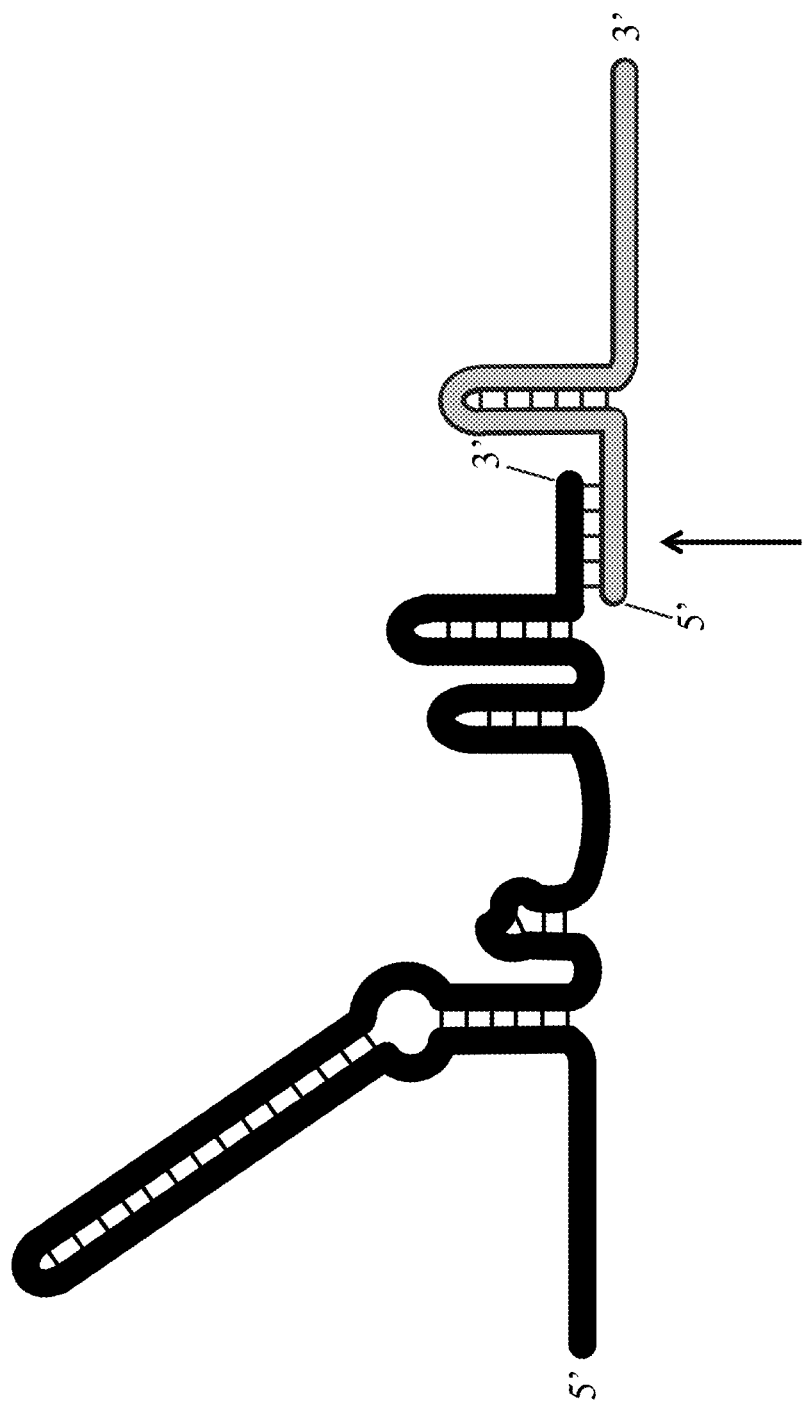

FIG. 5A and FIG. 5B illustrate examples of such non-covalently attachments using RNA NATNAs.

FIG. 5A illustrates an example of an engineered Cas9-Cpf1-NATNA. In this example, the 3' end of a Cas9-sgRNA is modified to remove a 3' hairpin element (FIG. 2, 207 or 208). The Cpf1-stem RNA sequence 1 (FIG. 3, 303), including the sequence 5' of the Cpf1 stem (about 3-6 nt), important for pseudo-knot formation, is covalently linked to the Cas9-sgRNA that was modified to remove a 3' hairpin. The Cpf1-NATNA is modified to remove the Cpf1-stem RNA sequence 1 (FIG. 3, 303), loop element (FIG. 3, 304), and the sequence 5' of the Cpf1 stem. The Cpf1-stem RNA sequence 1 (FIG. 3, 303) can hybridize through hydrogen base-pair bonding with the Cpf1-crRNA stem RNA sequence 2 (FIG. 3, 305). In the figure, the arrow indicates the region of hydrogen bonding between the Cpf1-stem RNA sequence 2 of the Cpf1-crRNA and the Cas9-sgRNA modified to comprise the Cpf1-stem RNA sequence 1, including the sequence 5' of the Cpf1 stem.

In another embodiment, additional sequences can be added to the 3' end of the Cas9-sgRNA and/or additional complementary or non-complementary sequences can be added to the 5' end of the Cpf1-crRNA. FIG. 5B illustrates an example of such an engineered Cas9-Cpf1-NATNA. In this example, the 3' end of a Cas9-sgRNA is modified by covalent attachment of a first linker element sequence and the 5' end of a Cpf1-crRNA is modified by covalent attachment of a second linker element sequence, wherein the first linker element and the second linker element hybridize and form an connection through hydrogen base-pair bonding. In the figure, the arrow indicates the region of hydrogen bonding between the first linker element and the second linker element.

In addition to covalent linkages and non-covalent linkages, other types of connections to form a cross-type-NATNA can be used between the first NATNA and the second NATNA including, but not limited to ligand/ligand binding moiety pairings, and/or cross-linking. Ligand/ligand binding moiety pairings can be useful to form a cross-type-NATNA include, but are not limited to: a selected nucleic acid sequence and a corresponding aptamer; and a nucleic acid secondary structure/a small molecule, ion, or protein that binds to the nucleic acid secondary structure. Typically, a first NATNA is adapted to comprise a ligand (e.g., the first NATNA comprises at its 3' end a selected nucleic acid sequence) and a second NATNA is adapted to comprise a ligand binding moiety (e.g., the second NATNA comprises an aptamer at its 5' end that binds the selected nucleic acid sequence).

Cross-linking agents useful to form a cross-type-NATNA (by cross-linking a first NATNA to a second NATNA) include, but are not limited to: alkylating agents (e.g., 1,3-bis(2-chloroethyl)-1-nitrosourea) and nitrogen mustard); cisplatin (cis-diamminedichloroplatinum(II)) and its derivatives); ionizing radiation; nitrous acid; reactive chemicals (e.g., malondialdehyde); psoralens (activated in the presence of UV); and aldehydes (e.g., acrolein and crotonaldehyde).

In preferred embodiments, the present invention includes an engineered cross-type-NATNA (comprising a first NATNA and a second NATNA) wherein the first NATNA is capable of forming a first complex with a first protein and the second NATNA is capable of forming a second complex with the second protein. Furthermore, if the first complex forms, it is capable of targeting site-specific binding to a first nucleic acid target sequence and, if the second complex forms, it is capable of targeting site-specific binding to a second nucleic acid target sequence. For example, an engineered CRISPR Class 2 cross-type-NATNA, comprising a Cpf1-NATNA and a Cas9-NATNA, is capable of forming a Cpf1-NATNA/Cpf1 protein complex with a Cpf1 protein and Cas9-NATNA/Cas9 protein complex with a Cas9 protein (the entire nucleoprotein complex is referred to as a Cas9-Cpf1-NATNA/Cas9&Cpf1 protein complex). When the Cas9-Cpf1-NATNA/Cpf1 protein complex is formed between the Cas9-Cpf1-NATNA and a Cpf1 protein, the complex is capable of binding a first double-stranded nucleic acid target sequence; and when the Cas9-Cpf1-NATNA/Cas9 protein complex is formed between the Cas9-NATNA (e.g., the first Cas9-NATNA and the second Cas9-NATNA or the single-Cas9-NATNA) and a Cas9 protein, the Cas9-Cpf1-NATNA/Cas9 protein complex is capable of binding a second double-stranded nucleic acid target sequence. Thus, when the Cas9-Cpf1-NATNA/Cas9&Cpf1 protein complex is formed, the Cas9-Cpf1-NATNA/Cas9&Cpf1 protein complex is capable of binding the first double-stranded nucleic acid target sequence and the second double-stranded nucleic acid target sequence.

Example 1 describes production of exemplary components of engineered cross-type-NATNAs.

Example 5 describes identification and screening of Class 2 crRNAs that can be used to make engineered cross-type- NATNAs of the present invention. Example 6 describes identification and screening of Class 2 tracrRNAs that can be used to make engineered cross-type-NATNAs of the present invention.

Example 8 describes a method of probing for sites in Class 2 Type V guide crRNA backbones that are tolerant of modification. Example 9 describes a method of probing for sites tolerant of modification in Class 2 Type II Cas9 guide RNA backbones. The information obtained by the methods of Example 8 and Example 9 provides guidance regarding sites in the backbones through which individual NATNAs can be connected to form engineered cross-type-NATNAs of the present invention.

In a second aspect, the present invention is directed to nucleic acid/protein compositions comprising a cross-type-NATNA (comprising a first NATNA and a second NATNA), a first protein with which the first NATNA is capable of forming a complex, and a second protein with which the second NATNA is capable of forming a complex; thus the cross-type-NATNA, the first protein, and the second protein are capable of forming a cross-type-NATNA/first&second protein complex. Typically, the first protein comprises one or more nuclease activities, and the second protein comprises one or more nuclease activities. In some embodiments, the first protein is catalytically inactive for one or more of the nuclease activities, the second protein is catalytically inactive for one or more of the nuclease activities, or both the first protein is catalytically inactive for one or more of the nuclease activities and the second protein is catalytically inactive for one or more of the nuclease activities. Other embodiments of the cross-type-NATNA/first&second protein complex, wherein either the first protein or the second protein is catalytically inactive, include association of a donor polynucleotide with the catalytically inactive protein.

In one embodiment of this second aspect of the present invention, a nucleic acid/protein composition comprises an engineered CRISPR Class 2 cross-type-NATNA as described herein, and a Cas9 protein, a Cpf1 protein, or both a Cas9 protein and a Cpf1 protein. In another embodiment, the engineered CRISPR Class 2 cross-type-NATNA is in a complex with the Cas9 protein (Cas9-Cpf1-NATNA/Cas9 protein complex), the Cpf1 protein (Cas9-Cpf1-NATNA/Cpf1 protein complex), or both the Cas9 protein and the Cpf1 protein (Cas9-Cpf1-NATNA/Cas9&Cpf1 proteins complex). The Cas9 protein and the Cpf1 protein can have combinations of the following endonuclease activities: for the Cas9 protein, both the RuvC-1 and HNH domains of the Cas9 protein can be catalytically inactive, the RuvC-1 domain of the Cas9 protein can be catalytically inactive, the HNH domain of the Cas9 protein can be catalytically inactive, and both the RuvC-1 and HNH domains of the Cas9 protein can be catalytically inactive; and for the Cpf1 protein, the Cpf1 protein can be catalytically active or catalytically inactive.

In some embodiments of the composition, either the Cas9 protein or the Cpf1 protein is catalytically inactive (dCas9 or dCpf1) and the composition further comprises a donor polynucleotide wherein the donor polynucleotide comprises a nucleotide sequence complementary to the spacer element, or the regions adjacent to the spacer element, of the Cpf1-NATNA when dCpf1 is present, or a nucleotide sequence complementary to the spacer element, or the regions adjacent to the spacer element, of the Cas9-NATNA when dCas9 is present. The donor polynucleotide is capable of associating with the spacer element, or the regions adjacent to the spacer element, through hydrogen bonding between the donor polynucleotide nucleotide sequence complementary to the spacer element, or the sequence adjacent to the spacer element.

Mutations of the Cas9 protein that are enzymatically inactive for RuvC-1-related nuclease activity, HNH-related nuclease activity, and both RuvC-1-related nuclease activity and HNH-related nuclease activity are known in the art. Mutations of the Cpf1 protein that are enzymatically inactive are known in the art (see, e.g., Yamano, T., et al., Cell 165(4):949-962 (2016)); Zetsche, B., et al., Cell 163:1-13 (2015)). Enzymatically inactive Argonaute proteins can be made by modification to one or both of the Argonaute nuclease domains (e.g., the PIWI and/or PAZ domains). A nuclease-deficient Argonaute protein can be engineering through sequence modification of the catalytic residues of nuclease domains, particularly the PIWI domain, of the Argonaute protein (Jinek, M., et al., Nature 457:405-412 (2009)). Additionally, naturally occurring nuclease-deficient Argonaute proteins are known in the art (e.g., with inactive PIWI domains), and can be used as models to design inactive variants of nuclease-active Argonautes (see, e.g., Makarova, K., et al., Biology Direct 4:29 (2009) [doi: 10.1186/1745-6150-4-29]).

Across CRISPR systems, "guide biogenesis" (also referred to as "guide processing") involves endonuclease or exonuclease truncation of the guide RNA sequence following transcription of the CRISPR array. Enzymatic processing of the guide RNA can be carried out by RNases encoded by the Cas operon (e.g., Cas6 of Class 1 Type I-E systems) or by endogenous RNases (e.g., RNase III of Class 2 Type II-A systems).

In Class 2 Type V systems, guide biogenesis is performed by the Cpf1 protein nuclease. The Cpf1 protein is also responsible for sequence-specific double-stranded DNA target cleavage.

Figure 14A:
FIG. 14A through FIG. 14E depict Cpf1-crRNAs.

In the Type V system, cleavage of the pre-crRNA (see, e.g., FIG. 14B) occurs in an upstream region (e.g., in a 5' direction) from the pseudo-knot secondary structure and results in the generation of a guide Cpf1 crRNA (see, e.g., FIG. 14A). In some embodiments of the present invention, preventing the Cpf1 protein from cleaving 5' of the guide crRNA stem element is useful, for example, to prevent separation of a Cas9-Cpf1 NATNA/Cas9&Cpf1 protein complex into a Cas9-NATNA/Cas9 protein complex and a Cpf1-NATNA/Cpf1 protein complex occurring as a result of Cpf1 protein cleavage of the Cpf1 NATNA/Cas9&Cpf1 protein complex. It has been demonstrated that the sequence of Type V pre-crRNA can be modified to prevent guide RNA processing by the Type V CRISPR Cpf1 protein (see Fonfara, I., et al., Nature 532(7600):517-521 (2016)).

One method to prevent Cpf1 cleavage of sequences 5' of the guide crRNA stem element is by modification (e.g., base mutations, insertions, deletions, or chemical modifications) of the bases in the region upstream of the pseudo-knot or within the pseudo-knot of the pre-crRNA to prevent the processing of the pre-crRNA by the Cpf1 protein. To evaluate the effect of such modifications on guide processing, the modified pre-crRNA is incubated in the presence of a cognate Cpf1 protein for a period of time in a suitable buffer. The mixture is treated with Proteinase K (Denville Scientific, South Plainfield, N.J.) to remove the protein and the mixture is analyzed by polyacrylamide gel electrophoresis to evaluate whether cleavage of the modified pre-crRNA occurs. A pre-crRNA not incubated in the presence of a cognate Cpf1 protein serves as positive control (i.e., a control for the absence of guide processing). If no single modification in the pre-crRNA is sufficient to ablate guide processing, then combinations of modifications exhibiting reduced processing of the pre-crRNA can be combined into a pre-crRNA design and retested for the absence of guide processing activity. Modifications of pre-crRNA that result in the inability of the modified pre-crRNA to be processed can be further evaluated for the ability of the Cpf1-pre-crRNA/Cpf1 protein complex to maintain sequence-specific binding and/or cleavage of a DNA target nucleic acid comprising the pre-crRNA spacer element.

A second method to prevent Cpf1 cleavage of sequences 5' of the guide crRNA stem element is by modification of the Cpf1 protein. In this method, the amino acid residues of the Cpf1 protein are modified to perturb guide processing. X-ray crystallography of guide crRNA/Cpf1 protein complexes has shown that the pseudo-knot is bound by the interface of two protein domains designated the wedge domain (WED) and the RuvC domain (see Yamano, T., et al., Cell 165(4): 949-962 (2016). Amino acid residues of Cpf1 proximal to the region binding the 5' end of the guide crRNA and/or the pseudo-knot structure are likely to be involved in endonuclease catalysis of pre-crRNAs. Mutagenesis strategies, such as alanine screening (see, e.g., Lefèvre, F., et al., Nucleic Acids Research 25(2):447-448 (1997); Lee, et al., Molecular Pharmacology 50(1):140-148 (1996)) can be used to modify regions within the WED and RuvC domain, or other domains within the Cpf1 protein, to identify residues in the protein responsible for guide crRNA processing. In this method, Cpf1 proteins comprising alanine mutations can be expressed and incubated with a cognate pre-crRNA in a suitable buffer. After incubation, Proteinase K is added to the reaction mix to remove the Cpf1 protein and the reaction mix is then analyzed by polyacrylamide gel electrophoresis to evaluate whether cleavage of the modified pre-crRNA occurred. A pre-crRNA not incubated in the presence of a cognate Cpf1 protein serves as positive control (i.e., a control for the absence of guide processing). If no single mutation in the Cpf1 protein is sufficient to ablate guide processing, then combinations of mutations exhibiting reduced processing of the pre-crRNA can be combined into a single Cpf1 protein construct and retested for the absence of guide processing activity. Candidate mutations or combinations of mutations in the Cpf1 protein can be further evaluated for the ability of the Cpf1-pre-crRNA complex to maintain sequence-specific binding and/or cleavage of a DNA target nucleic acid comprising the pre-crRNA spacer element.

In a third aspect, the present invention relates to nucleic acid sequences encoding a cross-type-NATNA (comprising a first NATNA and a second NATNA), as well as expression cassettes, vectors, and recombinant cells comprising nucleic acid sequences encoding cross-type-NATNAs. One embodiment of the third aspect of the present invention relates to one or more nucleic acid sequences encoding an engineered CRISPR Class 2 cross-type-NATNA. In some embodiments of the third aspect of the invention, such expression cassettes, vectors, and recombinant cells further comprise sequences encoding a first protein (e.g., a Cpf1 protein) with which the first NATNA is capable of forming a complex, and/or a second protein (e.g., a Cas9 protein) with which the second NATNA is capable of forming a complex.

In one embodiment, the present invention relates to one or more expression cassettes comprising one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex (e.g., one or more nucleic acid sequences encoding an engineered CRISPR Class 2 cross-type-NATNA, and optionally one or more nucleic acid sequences encoding a Cpf1 and/or a Cas9 protein). Expression cassettes typically comprise regulatory sequences that are involved in one or more of the following: regulation of transcription, post-transcriptional regulation, and regulation of translation. Expression cassettes can be introduced into a wide variety of organisms including bacterial cells, yeast cells, plant cells, and mammalian cells. Expression cassettes typically comprise functional regulatory sequences corresponding to the organism(s) into which they are being introduced.

In some embodiments, one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex (e.g., an engineered CRISPR Class 2 cross-type-NATNA, and optionally one or more nucleic acid sequences encoding a Cpf1 and/or a Cas9 protein) are operably linked to regulatory elements.

A further embodiment of the present invention relates to vectors, including expression vectors, comprising one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex (e.g., one or more nucleic acid sequences encoding an engineered CRISPR Class 2 cross-type-NATNA, and optionally one or more nucleic acid sequences encoding a Cpf1 and/or a Cas9 protein). Vectors can also include sequences encoding selectable or screenable markers. Furthermore, nuclear targeting sequences can also be added, for example, to Cas9 protein and Cpf1 protein coding sequences. Vectors can also include polynucleotides encoding protein tags (e.g., poly-His tags, hemagglutinin tags, fluorescent protein tags, bioluminescent tags). The coding sequences for such protein tags can be fused to, for example, the one or more nucleic acid sequences encoding a Cas9 protein and/or a Cpf1 protein.

General methods for construction of expression vectors are known in the art. Expression vectors for host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, and viral vectors (including lentivirus, retrovirus, adenovirus, herpes simplex virus I or II, parvovirus, reticuloendotheliosis virus, and adeno-associated virus (AAV) vectors) for cell transformation and gene expression and methods to easily allow cloning of such polynucleotides. Illustrative plant transformation vectors include those derived from a Ti plasmid of *Agrobacterium tumefaciens* (Lee, L. Y., et al., Plant Physiology 146(2): 325-332 (2008)). Also useful and known in the art are *Agrobacterium rhizogenes* plasmids. For example, SNAPGENE™ (GSL Biotech LLC, Chicago, Ill.; snapgene.com/resources/plasmid_files/your_time_is_valuable/) provides an extensive list of vectors, individual vector sequences, and vector maps, as well as commercial sources for many of the vectors.

Lentiviral vectors are examples of vectors useful for introduction into mammalian cells of one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex (e.g., one or more nucleic acid sequences encoding an engineered CRISPR Class 2 cross-type-NATNA, and optionally one or more nucleic acid sequences encoding a Cpf1 and/or a Cas9 protein). Lentivirus is a member of the Retroviridae family and is a single-stranded RNA virus, which can infect both dividing and non-dividing cells as well as provide stable expression through integration into the genome. To increase the safety of lentivirus, components necessary to produce a viral vector are split across multiple plasmids. Transfer vectors are typically replication incompetent and may additionally contain a deletion in the 3'LTR, which renders the virus self-inactivating after integration. Packaging and envelope plasmids are typically used in combination with a transfer vector. For example, a packaging plasmid can encode combinations of the Gag, Pol, Rev, and Tat genes. A transfer plasmid can comprise viral LTRs and the psi packaging signal. The envelope plasmid comprises an envelope protein (usually vesicular stomatitis virus glycoprotein, VSV-GP, because of its wide infectivity range).

Lentiviral vectors based on human immunodeficiency virus type-1 (HIV-1) have additional accessory proteins that facilitate integration in the absence of cell division. HIV-1 vectors have been designed to address a number of safety concerns. These include separate expression of the viral genes in trans to prevent recombination events leading to the generation of replication-competent viruses. Furthermore, the development of self-inactivating vectors reduces the potential for transactivation of neighboring genes and allows the incorporation of regulatory elements to target gene expression to particular cell types (see, e.g., Cooray, S., et al., Methods in Enzymology 507:29-57 (2012)).

Transformed host cells (or recombinant cells) are cells or the progeny of cells that have been transformed or transfected, using recombinant DNA techniques, with one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex (e.g., one or more nucleic acid sequences encoding an engineered CRISPR Class 2 cross-type-NATNA, and optionally one or more nucleic acid sequences encoding a Cpf1 and/or a Cas9 protein). Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, direct microinjection, and nanoparticle-mediated delivery.

As an alternative to expressing one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex, a cross-type-NATNA and/or the first and second protein can be directly introduced into a cell, for example. Or one or more components can be expressed by a cell and the other component(s) directly introduced. Methods to introduce the components into a cell include electroporation, lipofection, and ballistic gene transfer (e.g., using a gene gun or a biolistic particle delivery system).

A variety of exemplary host cells are disclosed herein that can be used to produce recombinant cells by introduction of one or more nucleic acid sequences encoding an engineered cross-type-NATNA, and optionally one or more nucleic acid sequences encoding a first protein with which the cross-type-NATNA is capable of forming a complex, and/or a second protein with which the cross-type-NATNA is capable of forming a complex (e.g., one or more nucleic acid sequences encoding an engineered CRISPR Class 2 cross-type-NATNA, and optionally one or more nucleic acid sequences encoding a Cpf1 and/or a Cas9 protein. Such host cells include, but are not limited to a plant cell, a yeast cell, a bacterial cell, an insect cell, an algal cell, or a mammalian cell.

Methods of introducing polynucleotides (e.g., an expression vector) into host cells to produce recombinant cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, direct microinjection, and nanoparticle-mediated delivery. For ease of discussion, "transfection" is used below to refer to any method of introducing polynucleotides into a host cell.

Preferred methods for introducing polynucleotides plant cells include microprojectile bombardment and *Agrobacterium*-mediated transformation. Alternatively, other non *Agrobacterium* species (e.g., *Rhizobium*) and other prokaryotic cells that are able to infect plant cells and introduce heterologous polynucleotides into the genome of the infected plant cell can be used. Other methods include electroporation, liposome-mediated transfection, transformation using pollen or viruses, and chemicals that increase free DNA uptake, or free DNA delivery using microprojectile bombardment. See, e.g., Narusaka, Y., et al., Chapter 9, in Transgenic Plants—Advances and Limitations, edited by Yelda, O., ISBN 978-953-51-0181-9 (2012).

In some embodiments, a host cell is transiently or non-transiently transfected. In some embodiments, a cell is transfected as it naturally occurs in a subject. In some embodiments, a cell that is transfected is taken from a subject, e.g., a primary cell or progenitor cell. In some embodiments, the primary cell or progenitor cell is cultured and/or is returned after ex vivo transfection to the same subject (autologous treatment) or to a different subject.

The cross-type-NATNA/first&second protein complexes described herein can be used to generate non-human transgenic organisms by site-specifically introducing a selected polynucleotide sequence at a DNA target locus in the genome to generate a modification of the genomic DNA. The transgenic organism can be an animal or a plant.

A transgenic animal is typically generated by introducing the system into a zygote cell. A basic technique, described with reference to making transgenic mice (Cho, A., et al., "Generation of Transgenic Mice," Current Protocols in Cell Biology, CHAPTER.Unit-19.11 (2009)), involves five basic steps: first, preparation of a system, as described herein, including a suitable donor polynucleotide; second, harvesting of donor zygotes; third, microinjection of the system into the mouse zygote; fourth, implantation of microinjected zygotes into pseudo-pregnant recipient mice; and fifth, performing genotyping and analysis of the modification of the genomic DNA established in founder mice. The founder mice will pass the genetic modification to any progeny. The founder mice are typically heterozygous for the transgene. Mating between these mice will produce mice that are homozygous for the transgene 25% of the time.

Methods for generating transgenic plants are also well known. A transgenic plant generated, e.g., using *Agrobacterium* transformation methods, typically contains one transgene inserted into one chromosome. It is possible to produce a transgenic plant that is homozygous with respect to a transgene by sexually mating (i.e., selfing) an independent segregant transgenic plant containing a single transgene to itself, for example an F0 plant, to produce F1 seed. Plants formed by germinating F1 seeds can be tested for homozygosity. Typical zygosity assays include, but are not limited to, single nucleotide polymorphism assays and thermal amplification assays that distinguish between homozygotes and heterozygotes.

As an alternative to using a system described herein for the direct transformation of a plant, transgenic plants can be formed by crossing a first plant that has been transformed with a system with a second plant that has never been exposed to the system. For example, a first plant line containing a transgene can be crossed with a second plant line to introgress the transgene into the second plant line, thus forming a second transgenic plant line.

A fourth aspect of the present invention relates to methods of using nucleic acid/protein compositions comprising an engineered cross-type-NATNA, a first protein with which the cross-type-NATNA is capable of forming a complex, and a second protein with which the cross-type-NATNA is capable of forming a complex. Embodiments of nucleic acid/protein compositions are described herein, for example, in the preceding second aspect of the invention.

In one embodiment, the present invention includes a method of binding a nucleic acid sequence (e.g., DNA), comprising contacting a first nucleic acid target sequence in the nucleic acid (e.g., DNA) and a second nucleic acid target sequence in the nucleic acid sequence (e.g., DNA) with a nucleic acid/protein composition comprising an engineered cross-type-NATNA in a complex with a first protein with which the cross-type-NATNA forms a complex, and a second protein with which the cross-type-NATNA forms a complex (e.g., an engineered CRISPR Class 2 cross-type-NATNA, a Cpf1 protein with which the CRISPR Class 2 cross-type-NATNA forms a complex, and a Cas9 protein with which the CRISPR Class 2 cross-type-NATNA forms a complex), thereby facilitating binding of the nucleic acid/protein composition to the first nucleic acid target sequence in the nucleic acid sequence and the second nucleic acid target sequence in the nucleic acid. The engineered cross-type-NATNA comprises a first-NATNA spacer element (e.g., a Cpf1-NATNA spacer element) that is complementary to the first nucleic acid target sequence (e.g., DNA) and a second-NATNA spacer element (e.g., a Cas9-NATNA spacer element) that is complementary to the second nucleic acid target sequence (e.g., DNA). In some embodiments the nucleic acid target sequence is DNA or genomic DNA. Such methods of binding a nucleic acid target sequence are carried out in vitro, in cell (e.g., in cultured cells), ex vivo (e.g., stem cells removed from a subject), and in vivo.

A variety of methods are known in the art to evaluate and/or quantitate protein-nucleic acid interactions including, but not limited to, the following: immunoprecipitation (ChIP) assays, DNA electrophoretic mobility shift assays (EMSA), DNA pull-down assays, and microplate capture and detection assays. Commercial kits, materials, and reagents are available to practice many of these methods from, for example, Thermo Scientific (Wilmington, Del.), Signosis (Santa Clara, Calif.), Bio-Rad (Hercules, Calif.), and Promega (Madison, Wis.)). A common approach to detect protein-nucleic acid interactions is EMSA (see, e.g., Hellman L. M., et al., Nature Protocols 2(8):1849-1861 (2007)).

In another embodiment, the present invention includes a method of cutting a nucleic acid sequence (e.g., DNA), comprising contacting a first nucleic acid target sequence in the nucleic acid (e.g., DNA) and a second nucleic acid target sequence in the nucleic acid sequence (e.g., DNA) with a nucleic acid/protein composition comprising an engineered cross-type-NATNA in a complex with a first protein with which the cross-type-NATNA forms a complex, and a second protein with which the cross-type-NATNA forms a complex (e.g., an engineered CRISPR Class 2 cross-type-NATNA, a Cpf1 protein with which the CRISPR Class 2 cross-type-NATNA forms a complex, and a Cas9 protein with which the CRISPR Class 2 cross-type-NATNA forms a complex), thereby facilitating binding of the nucleic acid/protein composition to the first nucleic acid target sequence in the nucleic acid sequence and the second nucleic acid target sequence in the nucleic acid. The engineered cross-type-NATNA comprises a first-NATNA spacer element (e.g., a Cpf1-NATNA spacer element) that is complementary to the first nucleic acid target sequence (e.g., DNA) and a second-NATNA spacer element (e.g., a Cas9-NATNA spacer element) that is complementary to the second nucleic acid target sequence (e.g., DNA). The first protein (e.g., Cpf1) of the bound nucleic acid/protein composition cuts the first nucleic acid target sequence, and the second protein (e.g., Cas9) of the bound nucleic acid/protein composition cuts the second nucleic acid target sequence. In some embodiments the nucleic acid target sequence is DNA or genomic DNA. Such methods of binding a nucleic acid target sequence are carried out in vitro, in cell (e.g., in cultured cells), ex vivo (e.g., stem cells removed from a subject), and in vivo.

Example 3 describes performance of Cas protein-mediated cleavage assays. Example 2 describes how to produce double-stranded DNA target regions for use in the cleavage assays.

Example 4 presents a deep sequencing analysis for detection of target modifications in eukaryotic cells using cross-type-NATNAs of the present invention. Example 7 presents an alternative analysis, the T7E1 assay, for detection of target modifications in eukaryotic cells using cross-type-NATNAs of the present invention.

Example 10 illustrates the use of cross-type-NATNAs of the present invention to select and modify DNA target sequences present in genomic DNA and to measure the level of cleavage activity at those sites.

Figure 11A:
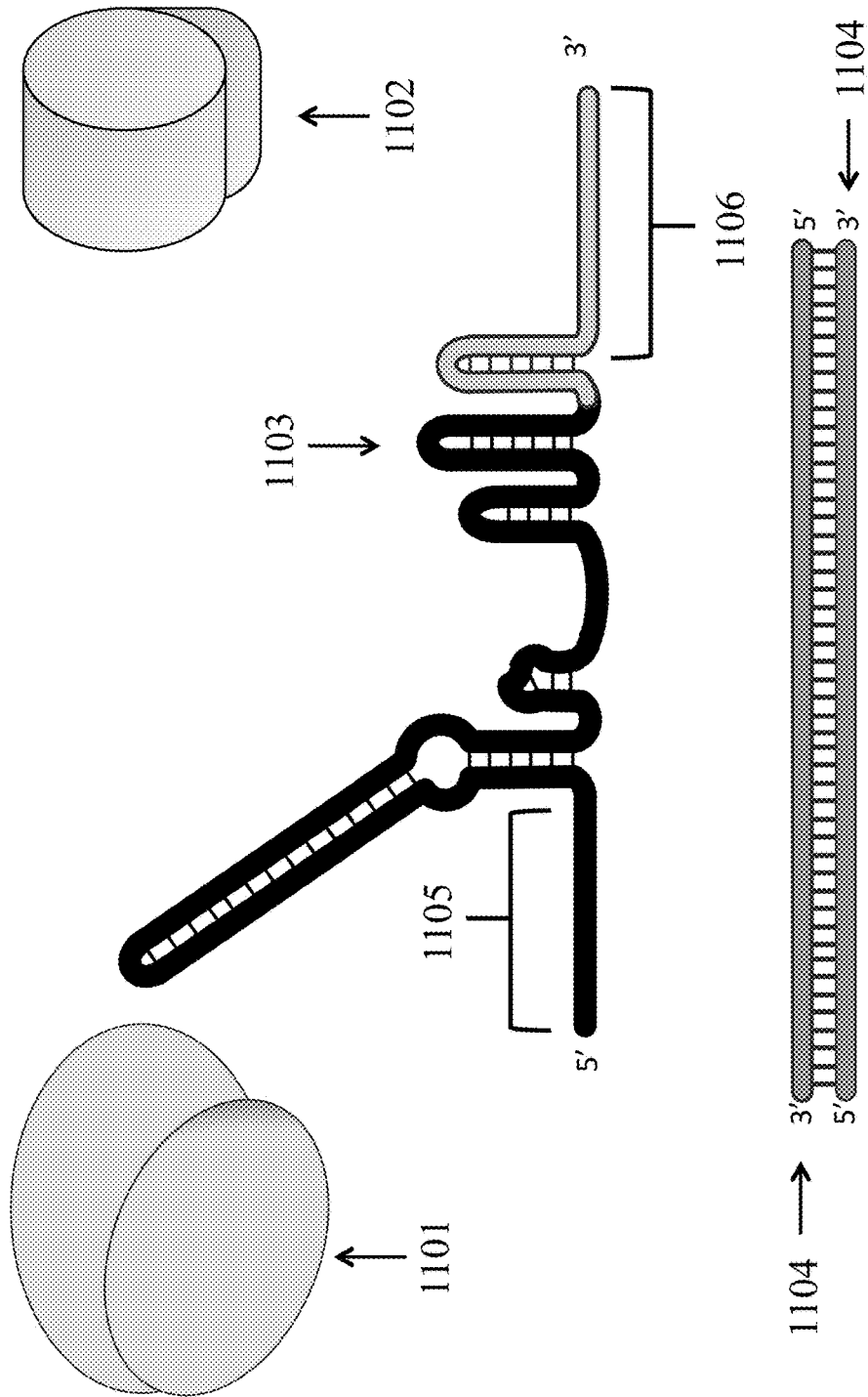
FIG. 11A, FIG. 11B, FIG. 11C, and FIG. 11D illustrate excision of a sequence from a nucleic acid target sequence using an engineered Cas9-Cpf1 nucleic-acid targeting nucleic acid and Cas9 and Cpf1 proteins both having active endonucleases.
Figure 11B:
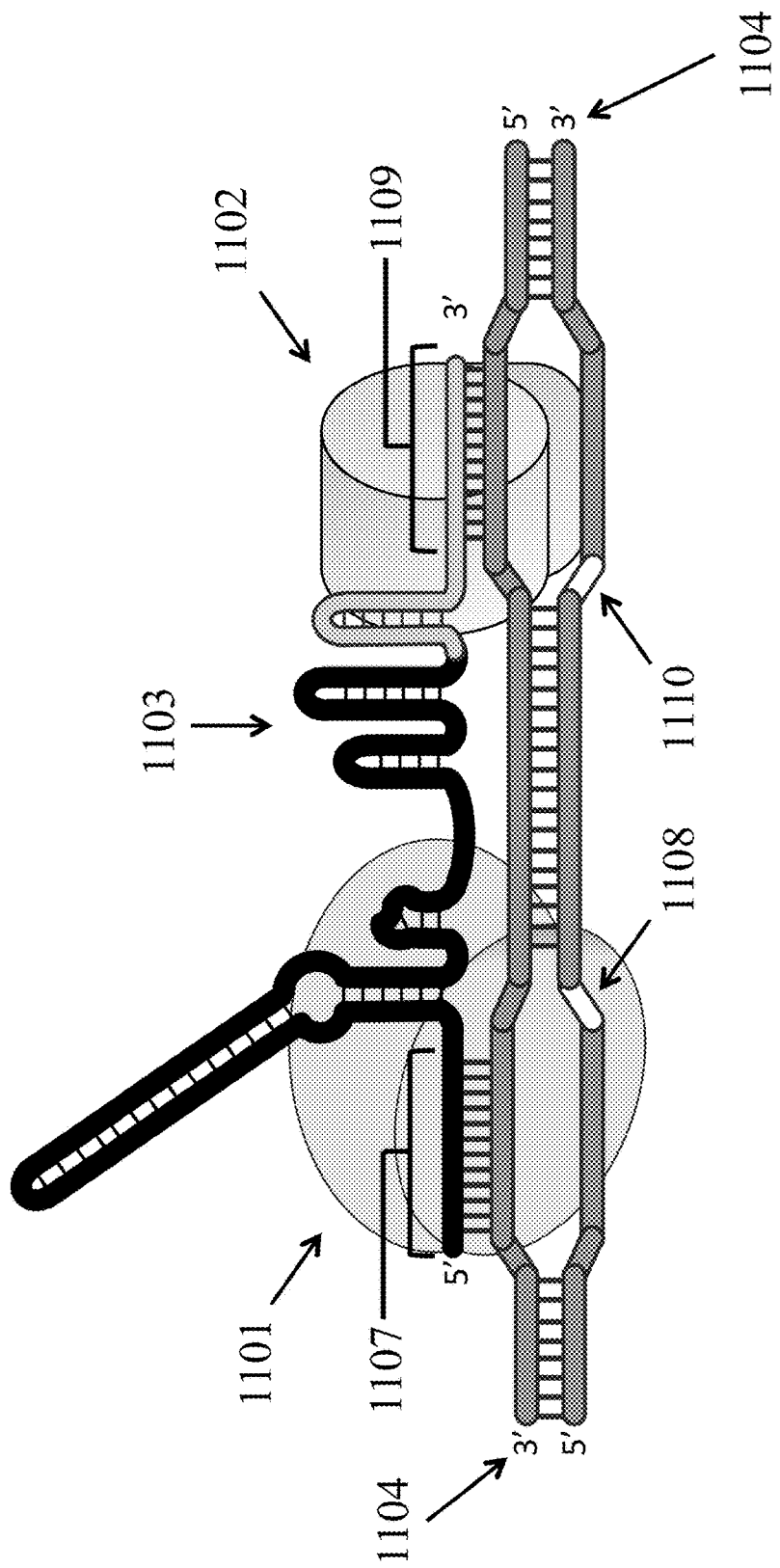
Figure 11C:
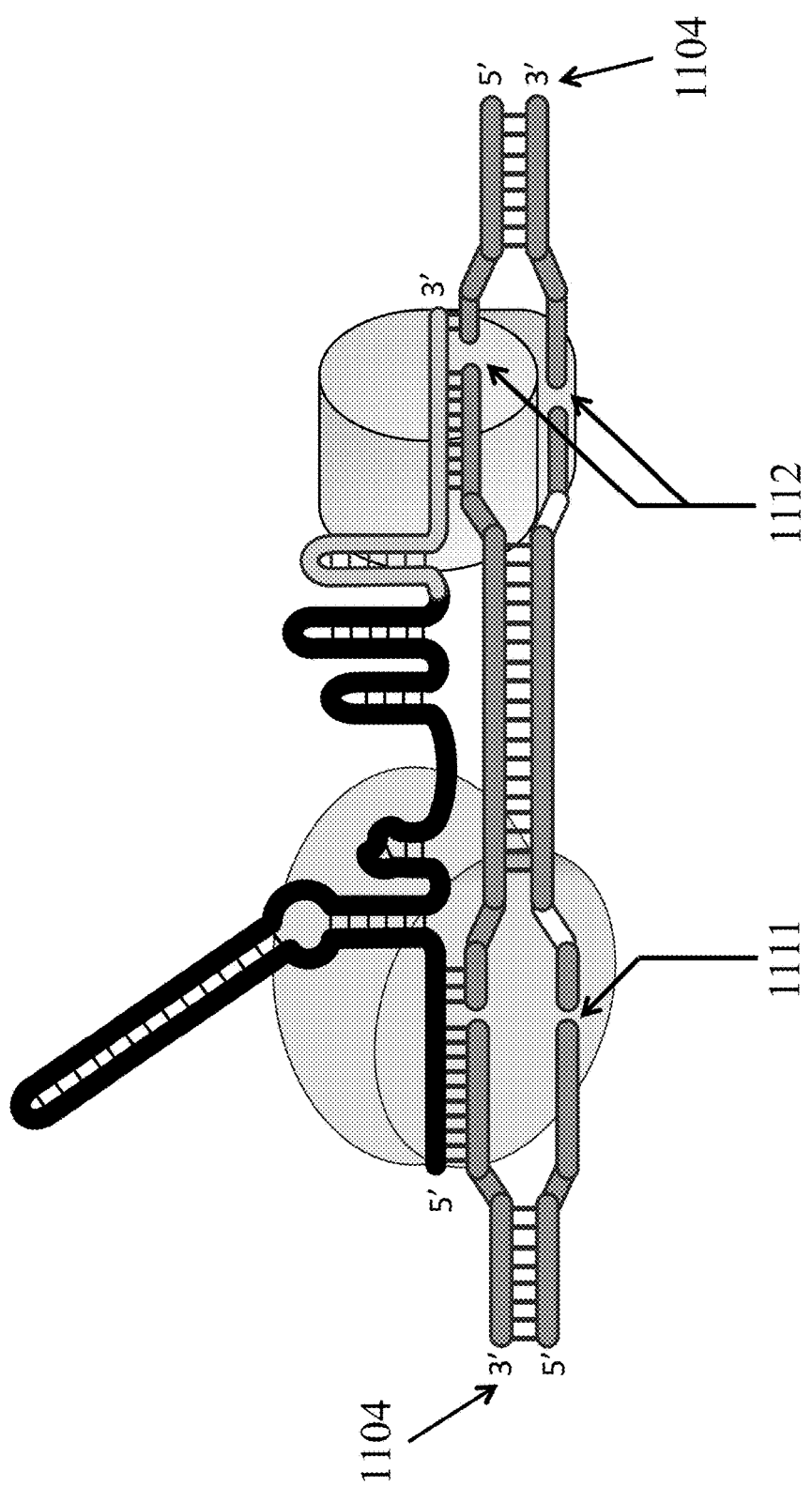
Figure 11D:
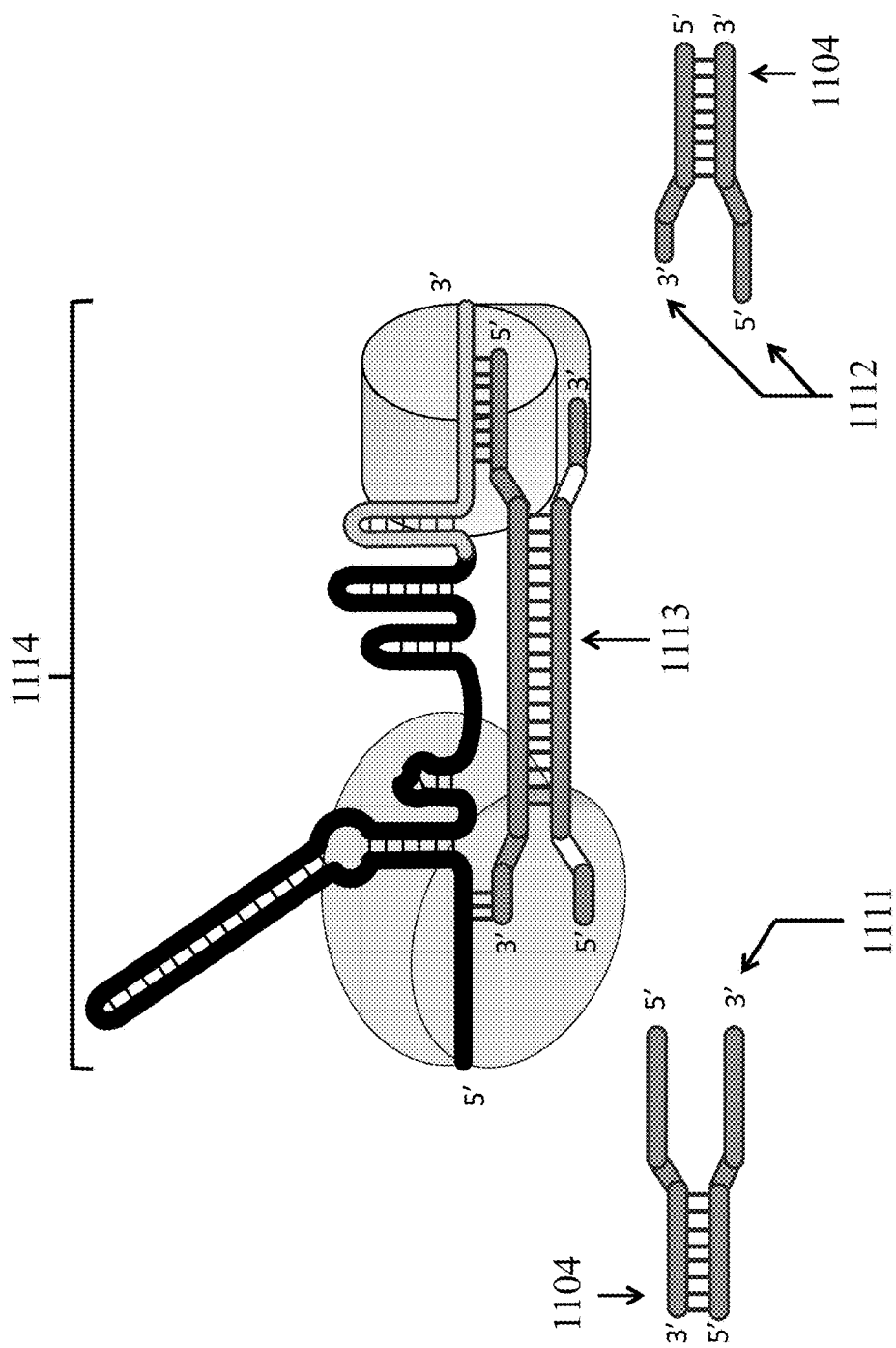

A method of cutting a nucleic acid target sequence is exemplified in FIG. 11A, FIG. 11B, FIG. 11C, and FIG. 11D. These figures present an example of excision of a sequence from a nucleic acid target using an engineered Cas9-Cpf1-NATNA and Cas9 and Cpf1 proteins both having active endonucleases. FIG. 11A shows a Cas9 protein (FIG. 11A, 1101) and a Cpf1 protein (FIG. 11A, 1102), an engineered Cas9-Cpf1-NATNA as shown in FIG. 4 (FIG. 11A, 1103), and a double-stranded nucleic acid (FIG. 11A, 1104) comprising a first DNA target binding sequence complementary to the Cas9-sgRNA spacer element (FIG. 11A, 1105) and a second DNA target binding sequence complementary to the Cpf1-crRNA spacer element (FIG. 11A, 1106). FIG. 11B illustrates the Cas9 (FIG. 11B, 1101) and Cpf1 (FIG. 11B, 1102) proteins in complex with the engineered Cas9-Cpf1-NATNA (FIG. 11B, 1103) and the hydrogen bonding of a first DNA target binding sequence to the Cas9-sgRNA spacer element (FIG. 11B, 1107) and a second DNA target binding sequence to the Cpf1-crRNA spacer element (FIG. 11B, 1109). In the figure, the double-stranded nucleic acid is indicated as FIG. 11B, 1104, the Cas9 PAM sequence in the double-stranded nucleic acid is indicated as FIG. 11B, 1108 and the Cpf1 PAM sequence is indicated as FIG. 11B, 1110. FIG. 11C illustrates double-strand blunt-end cuts made by Cas9 at the first DNA target binding sequence (FIG. 11C, 1111) and the double-strand staggered cuts made by Cpf1 at the second DNA target binding sequence (FIG. 11C, 1112). The double-stranded nucleic acid is indicated as FIG. 11C, 1104. FIG. 11D illustrates an excised nucleic acid sequence (FIG. 11D, 1113) that is still associated with the engineered Cas9-Cpf1-NATNA complex (FIG. 11D, 1114). One end of the nucleic acid target comprises a staggered double-strand break resulting from Cpf1 cleavage (FIG. 11D, 1112) and the other an essentially blunt end double-strand break resulting from Cas9 cleavage (FIG. 11D, 1111). The double-stranded nucleic acid is indicated as FIG. 11D, 1104. In other embodiments, the Cas9 and Cpf1 proteins are deficient in endonuclease activity and the binding of the engineered Cas9-Cpf1-NATNA complex to a nucleic acid target can be used, for example, to block transcription and subsequent expression of a gene adjacent to the nucleic acid target.

In yet another embodiment, the present invention includes a method of modifying DNA in a cell, comprising contacting a first DNA target sequence in the DNA and a second DNA target sequence in the DNA with a nucleic acid/protein composition comprising an engineered cross-type-NATNA in a complex with a first protein with which the cross-type-NATNA forms a complex, and a second protein with which the cross-type-NATNA forms a complex (e.g., an engineered CRISPR Class 2 cross-type-NATNA, a Cpf1 protein with which the CRISPR Class 2 cross-type-NATNA forms a complex, and a Cas9 protein with which the CRISPR Class 2 cross-type-NATNA forms a complex), thereby facilitating binding of the nucleic acid/protein composition to the first nucleic acid target sequence in the nucleic acid sequence and the second nucleic acid target sequence in the nucleic acid. The engineered cross-type-NATNA comprises a first-NATNA spacer element (e.g., a Cpf1-NATNA spacer element) that is complementary to the first DNA target sequence and a second-NATNA spacer element (e.g., a Cas9-NATNA spacer element) that is complementary to the second DNA target sequence (e.g., DNA). The first protein (e.g., Cpf1) of the bound nucleic acid/protein composition cuts the first DNA target sequence, and the second protein (e.g., Cas9) of the bound nucleic acid/protein composition cuts the second DNA target sequence. The cell repairs the first cut site and the second cut site. Cell DNA repair pathways include, HDR, NHEJ, MMEJ. In some embodiments the nucleic acid target sequence is DNA or genomic DNA. Such methods of binding a nucleic acid target sequence are carried out in vitro, in cell (e.g., in cultured cells), ex vivo (e.g., stem cells removed from a subject), and in vivo. The contracting step may further comprise a donor polynucleotide being present, wherein at least a portion of the donor polynucleotide is incorporated between the first cut site and the second cut site.

In another embodiment, the invention relates to a method to bring a donor polynucleotide into proximity of a double-strand break in a nucleic acid target, typically DNA, in a cell. The method comprises contacting a first DNA target sequence in the DNA and a second DNA target sequence in a donor polynucleotide with a nucleic acid/protein composition comprising an engineered cross-type-NATNA in a complex with a first protein with which the cross-type-NATNA forms a complex, and a second protein with which the cross-type-NATNA forms a complex (e.g., an engineered CRISPR Class 2 cross-type-NATNA, a Cpf1 protein with which the CRISPR Class 2 cross-type-NATNA forms a complex, and a Cas9 protein with which the CRISPR Class 2 cross-type-NATNA forms a complex), thereby facilitating binding of the nucleic acid/protein composition to the first DNA target sequence in the DNA and the second DNA target sequence in the donor polynucleotide. The first DNA target sequence is complementary to a first NATNA spacer (e.g., a Cpf1-NATNA spacer element or a Cas9-NATNA spacer element), wherein the associated first protein is a catalytically active nuclease protein (e.g., a Cpf1 protein or a Cas9 protein, respectively). The second DNA target sequence is complementary to a second NATNA spacer (e.g., a Cpf1-NATNA spacer element or a Cas9-NATNA spacer element), wherein the associated second protein is a catalytically inactive nuclease protein (e.g., a dCpf1 protein or a dCas9 protein, respectively). For example, when the catalytically active nuclease protein is a Cpf1 protein, the catalytically inactive nuclease protein is a dCas9 protein, and vice versa. The catalytically active nuclease protein of the bound nucleic acid/protein composition cuts the first DNA target sequence to form a cut site. The donor polynucleotide is in proximity to the cut site (e.g., the double-strand break) because the catalytically active nuclease protein and the catalytically inactive nuclease protein are complexed with the cross-type-NATNA, that is, they are part of the same nucleic acid/protein composition. In some embodiments, at least a portion of the donor polynucleotide is introduced into the cut site in the DNA (e.g., by an HDR repair process) resulting in modifying the DNA.

Figure 12A:
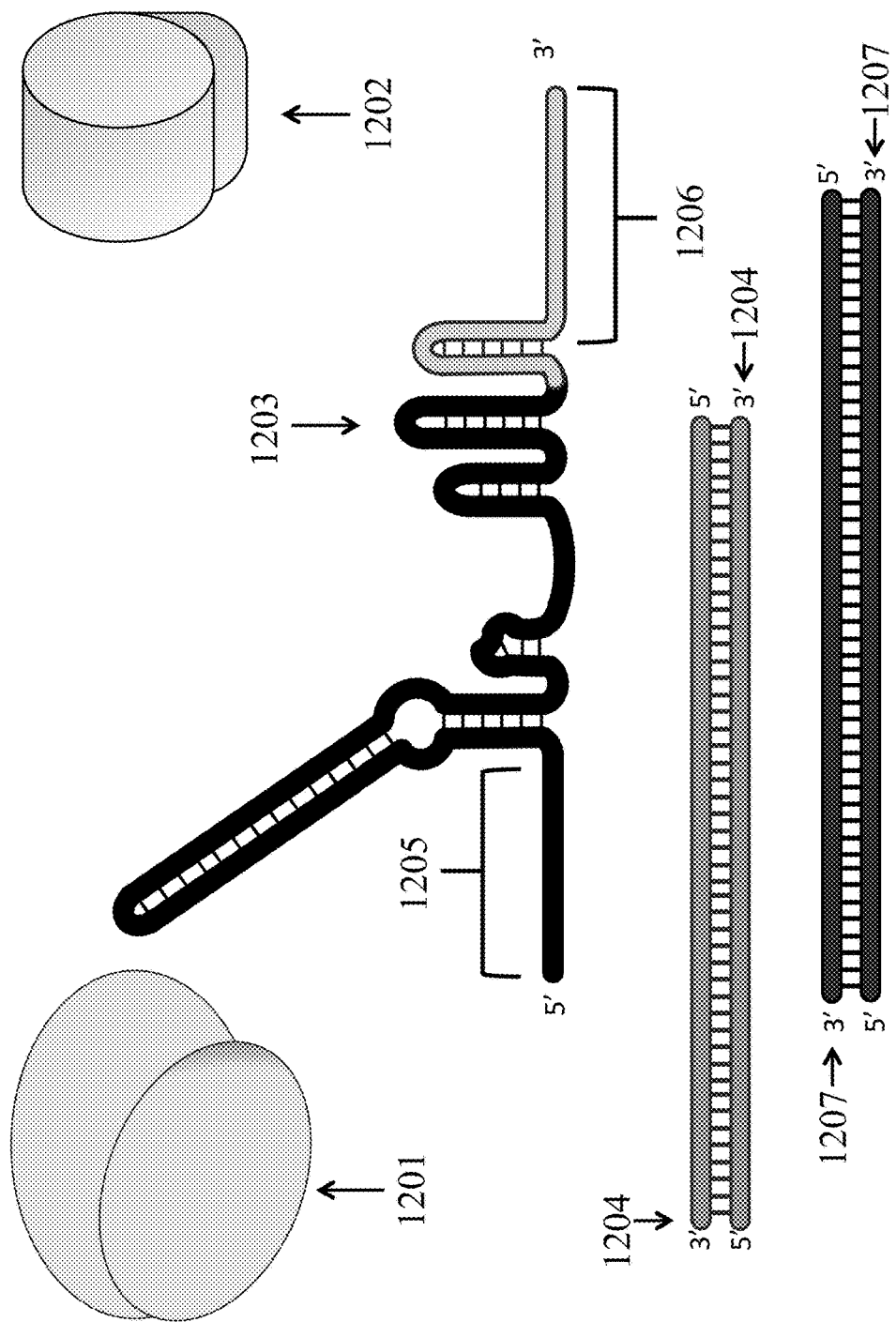
FIG. 12A, FIG. 12B, and FIG. 12C illustrate using an engineered Cas9-Cpf1 nucleic-acid targeting nucleic acid and Cas9 and Cpf1 proteins, wherein endonuclease domains of Cas9 are active and the endonuclease domain of Cpf1 is inactive, to bring a donor polynucleotide into proximity of a DSB in a nucleic acid target sequence.
Figure 12B:
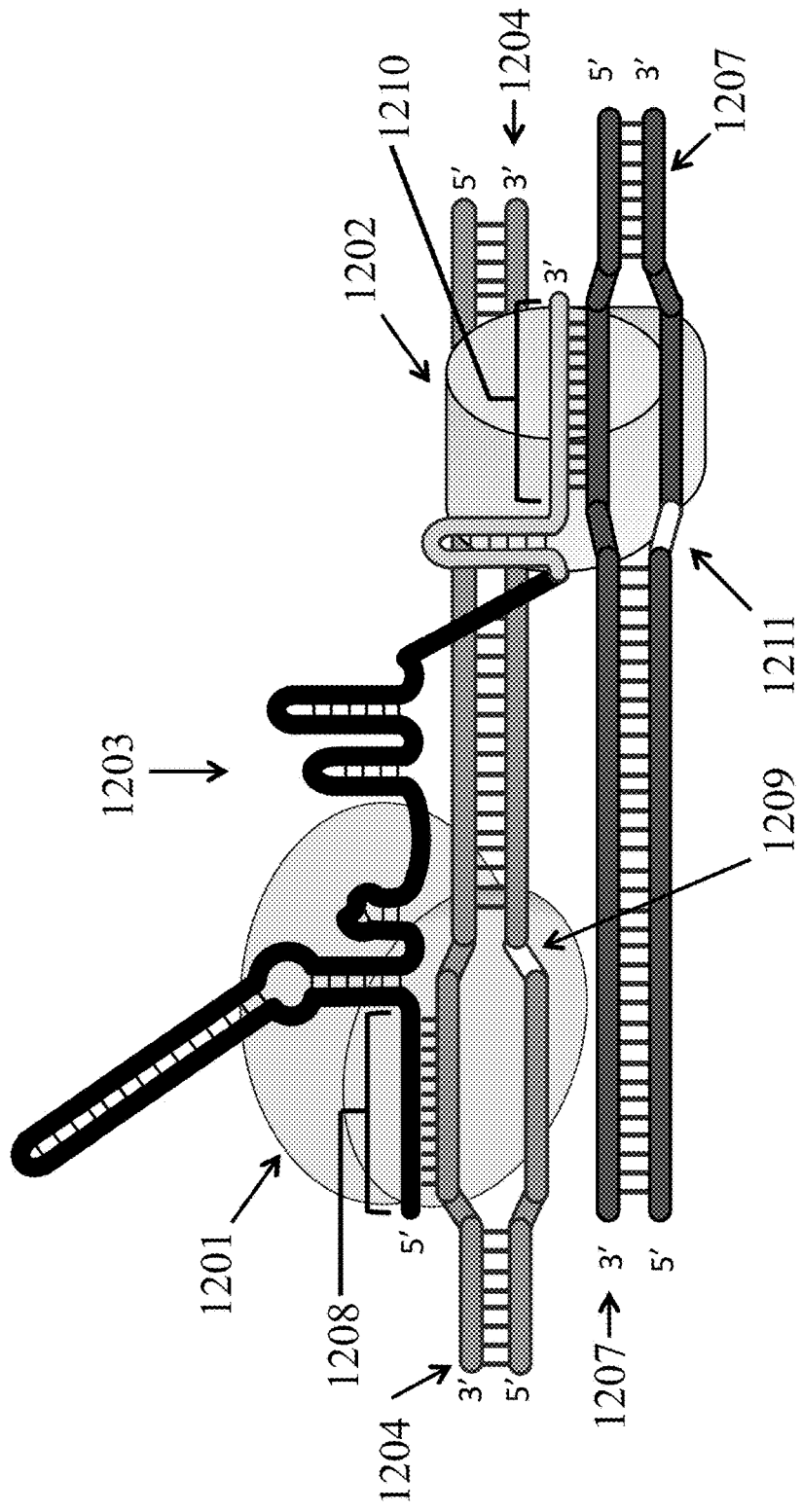
Figure 12C:
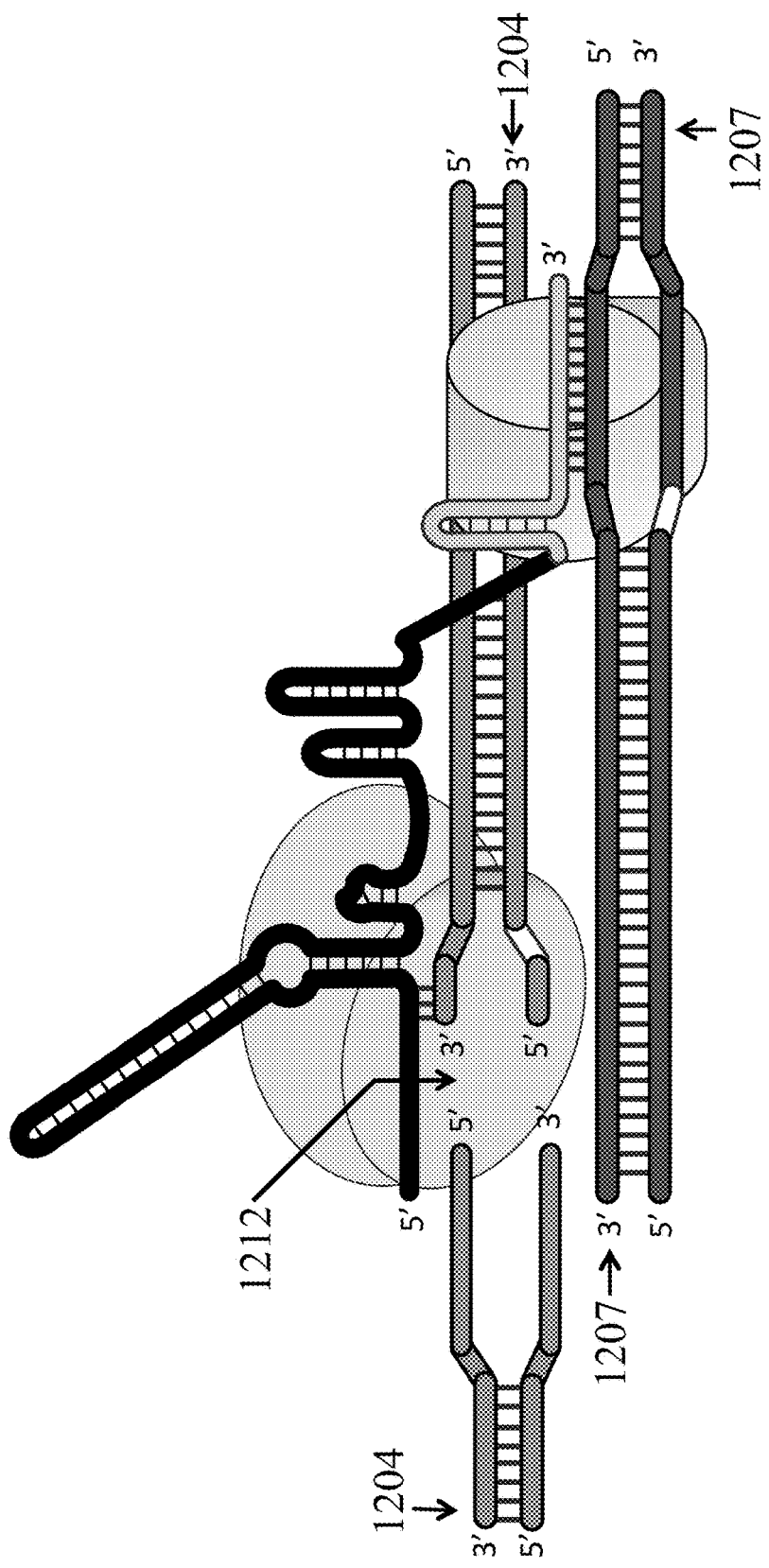

FIG. 12A, FIG. 12B, and FIG. 12C illustrate using an engineered Cas9-Cpf1-NATNA and Cas9 and Cpf1 proteins, wherein endonuclease domains of Cas9 are active and the endonuclease domain of Cpf1 is inactive, to bring a donor polynucleotide into proximity of a double-strand break in a nucleic acid target. FIG. 12A shows a Cas9 protein (FIG. 12A, 1201) and a Cpf1 protein (FIG. 12A, 1202), an engineered Cas9-Cpf1-NATNA as shown in FIG. 4 (FIG. 12A, 1203), and a double-stranded nucleic acid (FIG. 12A, 1204) comprising a first DNA target binding sequence complementary to the Cas9-sgRNA spacer element (FIG. 12A, 1205) and a donor polynucleotide (FIG. 12A, 1207) comprising a second DNA target binding sequence complementary to the Cpf1-crRNA spacer element (FIG. 12A, 1206). FIG. 12B illustrates the Cas9 (FIG. 12B, 1201) and Cpf1 (FIG. 12B, 1202) proteins in complex with the engineered Cas9-Cpf1-NATNA (FIG. 12B, 1203) and the hydrogen bonding of the first DNA target binding sequence to the Cas9-sgRNA spacer element (FIG. 12B, 1208) and the second DNA target binding sequence in the donor polynucleotide to the Cpf1-crRNA spacer element (FIG. 12B, 1210). In the figure, the Cas9 PAM sequence in the double-stranded nucleic acid is indicated as FIG. 12B, 1209 and the Cpf1 PAM sequence in the donor polynucleotide is indicated as FIG. 12B, 1211. The double-stranded nucleic acid is indicated as FIG. 12B, 1204, and the donor polynucleotide is indicated as FIG. 12B, 1207. FIG. 12C illustrates double-strand blunt-end cuts made by Cas9 at the first DNA target binding sequence (FIG. 12C, 1212) and shows the donor polynucleotide (FIG. 12C, 1207) in proximity to the double-strand blunt-end cuts. Having the donor polynucleotide (FIG. 12C, 1207) in close proximity to the double-strand cuts (FIG. 12C, 1212) increases the likelihood of integration of the donor polynucleotide sequences, or portions thereof, into the double-stranded nucleic acid comprising the nucleic acid target (FIG. 12C, 1204). In some embodiments, the endonuclease domain of Cpf1 is active and capable of binding to and cleaving the donor molecule, but Cpf1 does not disassociate from the donor after cleavage.

Figure 13A:
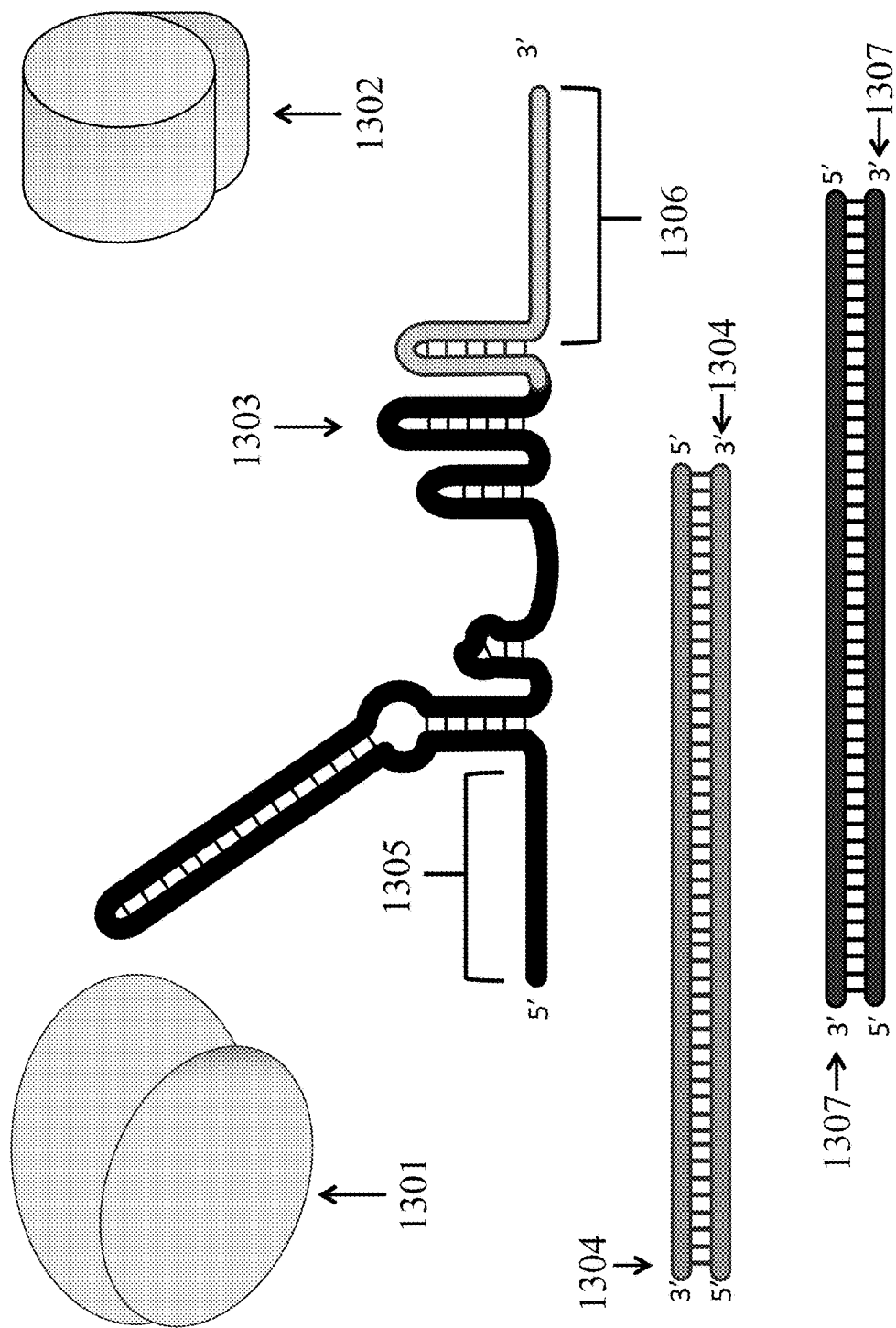
FIG. 13A, FIG. 13B, and FIG. 13C illustrate using an engineered Cas9-Cpf1 nucleic-acid targeting nucleic acid and Cas9 and Cpf1 proteins, wherein endonuclease domains of Cas9 are inactive and the endonuclease domain of Cpf1 is active, to bring a donor polynucleotide into proximity of a double-strand break in a nucleic acid target sequence.
Figure 13B:
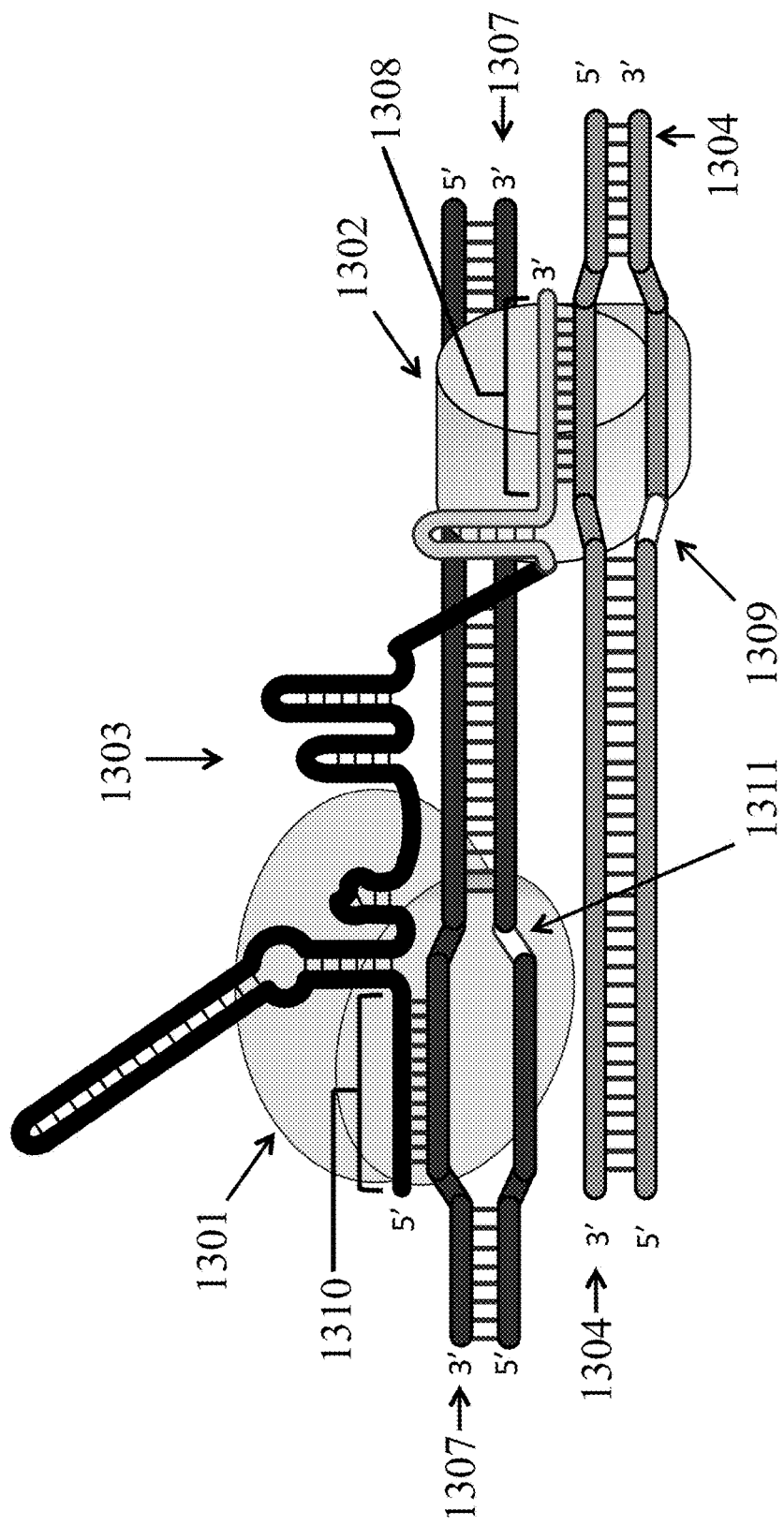
Figure 13C:
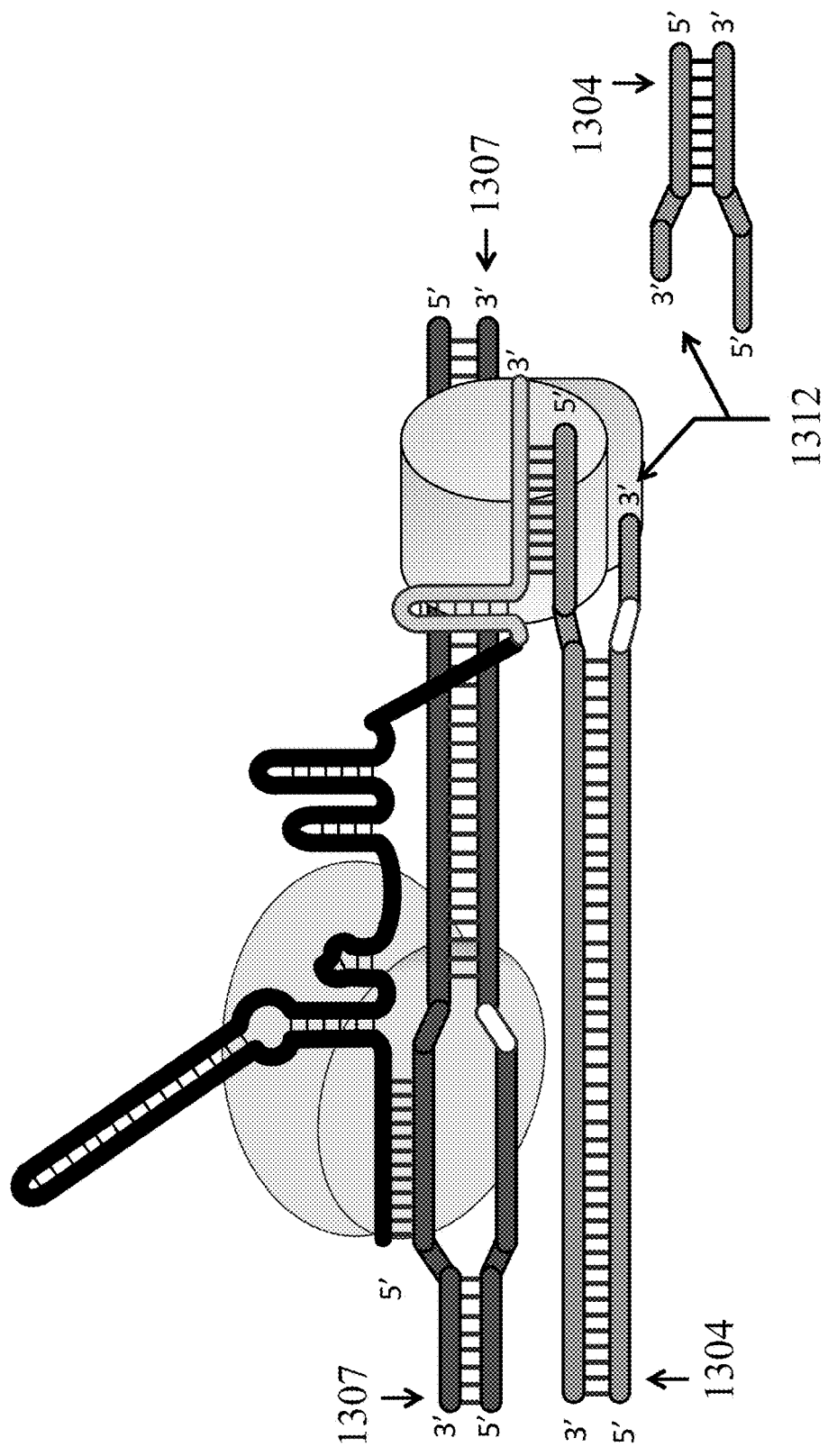

FIG. 13A, FIG. 13B, and FIG. 13C illustrate using an engineered Cas9-Cpf1-NATNA and Cas9 and Cpf1 proteins, wherein endonuclease domains of Cas9 are inactive and the endonuclease domain of Cpf1 is active, to bring a donor polynucleotide into proximity of a double-strand break in a nucleic acid target. FIG. 13A shows a Cas9 protein (FIG. 13A, 1301) and a Cpf1 protein (FIG. 13A, 1302), an engineered Cas9-Cpf1-NATNA as shown in FIG. 4 (FIG. 13A, 1303), and a double-stranded nucleic acid (FIG. 13A, 1304) comprising a first DNA target binding sequence complementary to the Cpf1-crRNA spacer element (FIG. 13A, 1306) and a donor polynucleotide (FIG. 13A, 1307) comprising a second DNA target binding sequence complementary to the Cas9-sgRNA spacer element (FIG. 13A, 1305). FIG. 13B illustrates the Cas9 (FIG. 13B, 1301) and Cpf1 (FIG. 13B, 1302) proteins in complex with the engineered Cas9-Cpf1-NATNA (FIG. 13B, 1303) and the hydrogen bonding of the first DNA target binding sequence to the Cpf1-crRNA spacer element (FIG. 13B, 1308) and the second DNA target binding sequence in the donor polynucleotide to the Cas9-sgRNA spacer element (FIG. 13B, 1310). In FIG. 13B, the Cpf1 PAM sequence in the double-stranded nucleic acid is indicated as 1309 and the Cas9 PAM sequence in the donor polynucleotide is indicated as 1311. The double-stranded nucleic acid comprising the first DNA target binding sequence is indicated as FIG. 13B, 1304. FIG. 13C illustrates double-strand staggered cuts made by Cpf1 at the first DNA target binding sequence (FIG. 13C, 1312) and shows the donor polynucleotide (FIG. 13C, 1307) in proximity to the double-strand staggered cuts. Having the donor polynucleotide (FIG. 13C, 1307) in close proximity to the double-strand cuts (FIG. 13C, 1312) increases the likelihood of integration of the donor polynucleotide sequences, or portions thereof, into the double-stranded nucleic acid comprising the first DNA target binding sequence (FIG. 13C, 1304). In some embodiments, the endonuclease domains of Cas9 are active and capable of binding to and cleaving the donor molecule, but Cas9 does not disassociate from the donor after cleavage.

In a further embodiment, the invention relates to a method of bringing a first nucleic acid target site, typically DNA, into the proximity of a second nucleic acid target site, typically DNA, in a cell. The method comprises contacting a first nucleic target sequence and a second nucleic target sequence with a nucleic acid/protein composition comprising an engineered cross-type-NATNA in a complex with a first protein with which the cross-type-NATNA forms a complex, and a second protein with which the cross-type-NATNA forms a complex (e.g., an engineered CRISPR Class 2 cross-type-NATNA, a Cpf1 protein with which the CRISPR Class 2 cross-type-NATNA forms a complex, and a Cas9 protein with which the CRISPR Class 2 cross-type-NATNA forms a complex), thereby facilitating binding of the nucleic acid/protein composition to the first nucleic acid target sequence and the second nucleic acid target sequence. The first DNA target sequence is complementary to a first NATNA spacer (e.g., a Cpf1-NATNA spacer element or a Cas9-NATNA spacer element), wherein the associated first protein is a catalytically inactive nuclease protein (e.g., a dCpf1 protein or a dCas9 protein, respectively). The second DNA target sequence is complementary to a second NATNA spacer (e.g., a Cpf1-NATNA spacer element or a Cas9-NATNA spacer element), wherein the associated second protein is a catalytically inactive nuclease protein (e.g., a dCpf1 protein or a dCas9 protein, respectively). For example, if the first protein is a dCpf1 protein, the second protein is a dCas9 protein, and vice versa. The first nucleic acid target site is brought into proximity of a second nucleic acid target site because the first and second catalytically inactive nuclease proteins are complexed with the cross-type-NATNA, that is, they are part of the same nucleic acid/protein composition. In some embodiments, the first nucleic acid target sequence and the second nucleic acid target sequence are on separate polynucleotides (e.g., different chromosomes) or a single polynucleotide comprises the first nucleic acid target sequence and the second nucleic acid target sequence (e.g., different sections of the same chromosome).

In yet another embodiment, the present invention also includes methods of modulating in vitro or in vivo transcription, for example, transcription of a gene comprising regulatory element sequences. The method comprises contacting a first nucleic target sequence and a second nucleic target sequence with a nucleic acid/protein composition comprising an engineered cross-type-NATNA in a complex with a first protein with which the cross-type-NATNA forms a complex, and a second protein with which the cross-type-NATNA forms a complex (e.g., an engineered CRISPR Class 2 cross-type-NATNA, a Cpf1 protein with which the CRISPR Class 2 cross-type-NATNA forms a complex, and a Cas9 protein with which the CRISPR Class 2 cross-type-NATNA forms a complex), thereby facilitating binding of the nucleic acid/protein composition to the first nucleic acid target sequence and the second nucleic acid target sequence. At least one of the first DNA target sequence and the second DNA target sequence comprise the regulatory element sequences. The first DNA target sequence is complementary to a first NATNA spacer (e.g., a Cpf1-NATNA spacer element or a Cas9-NATNA spacer element), wherein the associated first protein is a catalytically inactive nuclease protein (e.g., a dCpf1 protein or a dCas9 protein, respectively). The second DNA target sequence is complementary to a second NATNA spacer (e.g., a Cpf1-NATNA spacer element or a Cas9-NATNA spacer element), wherein the associated second protein is a catalytically inactive nuclease protein (e.g., a dCpf1 protein or a dCas9 protein, respectively). For example, if the first protein is a dCpf1 protein, the second protein is a dCas9 protein, and vice versa. In addition, the first and/or second protein can be fusion proteins, for example, dCas9 fused to a repressor or activator domain, and/or dCpf1 fused to a repressor or activator domain. The binding of the nucleic acid/protein composition to the first DNA target sequence and the second DNA target sequence modulates transcription of the gene. In some embodiments, the first DNA target sequence and the second DNA target sequence comprise the regulatory element sequences, and the first DNA target sequence comprises a promoter and the second DNA target sequence comprises a transcription start site.

Any of the components of the nucleic acid/protein compositions comprising an engineered cross-type-NATNA of the present invention or nucleic acid sequences encoding such components, as described above, can be incorporated into a kit, optionally including one or more reagents. In some embodiments, a kit includes a package with one or more containers holding the kit elements, as one or more separate compositions or, optionally, as admixture wherein the compatibility of the components will allow. In some embodiments, kits also comprise a buffer, a buffering agent, a salt, a sterile aqueous solution, and/or preservatives. Illustrative kits comprise an engineered CRISPR Class 2 cross-type-NATNA, and optionally a Cpf1 and/or a Cas9 protein, and one or more nucleic acid sequences encoding an engineered CRISPR Class 2 cross-type-NATNA, and optionally one or more nucleic acid sequences encoding a Cpf1 and/or a Cas9 protein.

Furthermore, kits can further comprise instructions for using components of the nucleic acid/protein compositions comprising an engineered cross-type-NATNA of the present invention or nucleic acid sequences encoding such components. Instructions included in kits of the invention can be affixed to packaging material or can be included as a package insert. Although the instructions are typically written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. Instructions can also include the address of an internet site that provides the instructions.

Another aspect of the invention relates to methods of making or manufacturing an engineered cross-type-NATNA or a nucleic acid/protein composition comprising an engineered cross-type-NATNA of the present invention. In one embodiment, the methods of making or manufacturing comprises chemically synthesizing an engineered cross-type-NATNA. In some embodiments, an engineered cross-type-NATNA comprises RNA bases and can be generated from DNA templates using in vitro transcription.

A nucleic acid/protein composition comprising an engineered cross-type-NATNA (e.g., an engineered CRISPR Class 2 cross-type-NATNA) can further comprise a detectable label, including a moiety that can provide a detectable signal. Examples of detectable labels include, but are not limited to, an enzyme, a radioisotope, a member of a specific binding pair, a fluorophore (FAM), a fluorescent protein (green fluorescent protein, red fluorescent protein, mCherry, tdTomato), an DNA or RNA aptamer together with a suitable fluorophore (enhanced GFP (EGFP), "Spinach"), a quantum dot, an antibody, and the like. A large number and variety of suitable detectable labels are well-known to one of ordinary skill in the art.

A nucleic acid/protein composition comprising an engineered cross-type-NATNA (e.g., an engineered CRISPR Class 2 cross-type-NATNA) or cells modified by use of a nucleic acid/protein composition comprising an engineered cross-type-NATNA, as described herein, can be used as a pharmaceutical composition formulated, for example, with a pharmaceutically acceptable excipient. Illustrative excipients include carriers, stabilizers, diluents, dispersing agents, suspending agents, thickening agents, and the like. The pharmaceutical composition can facilitate administration of a nucleic acid/protein composition comprising an engineered cross-type-NATNA to an organism. Pharmaceutical compositions can be administered in therapeutically effective amounts by various forms and routes including, for example, intravenous, subcutaneous, intramuscular, oral, aerosol, parenteral, ophthalmic, and pulmonary administration.

Numerous advantages are obtained using an engineered cross-type-NATNA of the present invention, comprising a first-NATNA and a second-NATNA, wherein a first protein is capable of forming a complex with the first-NATNA of the cross-type-NATNA, and a second protein is capable of forming a complex with the second-NATNA of the cross-type-NATNA (e.g., an engineered CRISPR Class 2 cross-type-NATNA, comprising a Cpf1-NATNA and a Cas9-NATNA, wherein a Cpf1 protein is capable of forming a complex with the Cpf1-NATNA of the CRISPR Class 2 cross-type-NATNA, and a Cas9 protein is capable of forming a complex with the Cas9-NATNA of the CRISPR Class 2 cross-type-NATNA) including, but not limited to:
  a reduction in off-targeting binding using a nucleic acid/protein composition comprising an engineered cross-type-NATNA (e.g., a Cas9-Cpf1-NATNAs), relative to a first-NATNA/first protein complex alone (e.g., a Cpf1-NATNA/Cpf1 protein complex) or a second-NATNA/second protein complex alone (e.g., a Cas9-NATNA/Cas9 protein complex);
  tethering of a donor polynucleotide through use of a nucleic acid/protein composition comprising an engineered cross-type-NATNA (e.g., a Cas9-Cpf1-NATNA) to bring the donor polynucleotide into proximity of a cut in a double-stranded nucleic acid;
  bringing two separate polynucleotides (e.g., two different chromosomes) or two regions of a single polynucleotide (e.g., two regions of a single chromosome) into proximity of each other using a nucleic acid/protein composition comprising an engineered cross-type-NATNA (e.g., a Cas9-Cpf1-NATNA); and
  transcriptional modulation of a target gene by binding of a nucleic acid/protein composition comprising an engineered cross-type-NATNA (e.g., a Cas9-Cpf1-NATNA) to regulatory sequences operably linked to the target gene.

Yet another advantage of a nucleic acid/protein composition comprising an engineered cross-type-NATNA (e.g., a Cas9-Cpf1-NATNA) is eliminating the need of a PAM sequence for cleavage of a nucleic acid target. For example, a first nucleic acid target sequence complementary to a first spacer element (see, e.g., FIG. 13A, 1305) is selected. The first nucleic acid target sequence comprises a PAM sequence for the first protein (e.g., a Cpf1 PAM). A second nucleic acid target sequence complementary to a second spacer element (see, e.g., FIG. 13A, 1306) is selected, wherein the second nucleic acid target sequence lacks a PAM sequence for the second protein (e.g., a Cas9 PAM) and is in close proximity to the first nucleic acid targeting sequence. The first protein (e.g., a Cpf1 protein) in nucleic acid/protein composition comprising an engineered cross-type-NATNA (e.g., a Cas9-Cpf1-NATNA) is endonuclease inactive (e.g., a dCpf1 protein) and the second protein has an active endonuclease (e.g., a Cas9 protein). The local unwinding caused by the inactive endonuclease protein binding to the first nucleic acid target can allow cleavage at the second nucleic acid target site by the active endonuclease protein even in the absence of a PAM for the active endonuclease protein. (Similarly an endonuclease inactive Cas9 and an endonuclease active Cpf1 can be used.)

Various embodiments contemplated herein include, but are not be limited to, one or more of the following. The embodiments are numbered for ease of reference.

Embodiment 1

An engineered three-element nucleic-acid targeting nucleic acid (NATNA), comprising: a Cpf1-associated NATNA comprising a spacer element, a 5' end, and a 3' end; a Cas9-associated first NATNA comprising a spacer element, a 5' end, and a 3' end; and a Cas9-associated second NATNA comprising a tracr element, a 5' end, and a 3' end; wherein the Cas9-associated first NATNA and the Cas9-associated second NATNA are associated through hydrogen base-pair bonding; and wherein Cpf1-associated NATNA is connected with the 5' end or the 3' end of the Cas9-associated first NATNA comprising a spacer element, or the 5' end or the 3' end of the Cas9-associated second NATNA comprising a tracr element.

Embodiment 2

The engineered three-element NATNA of embodiment 1, wherein a complex formed between the Cpf1-associated NATNA and a Cpf1 protein is capable of binding a first double-stranded nucleic acid target sequence; and wherein a complex formed between the Cas9-associated first NATNA, the Cas9-associated second NATNA, and a Cas9 protein is capable of binding a second double-stranded nucleic acid target sequence.

Embodiment 3

The engineered three-element NATNA of embodiment 1 or 2, wherein the Cpf1-associated NATNA is connected with the 5' end or 3' end of the Cas9-associated first NATNA, or the 5' end or 3' end of the Cas9-associated second NATNA, and the connection is through hydrogen bonding.

Embodiment 4

The engineered three-element NATNA of embodiment 3, wherein the Cpf1-associated NATNA further comprises a covalently connected linker element at the 5' end and/or the 3' end of the Cpf1-associated NATNA.

Embodiment 5

The engineered three-element NATNA of embodiment 3 or 4, wherein the Cas9-associated first NATNA and/or the Cas9-associated second NATNA further comprises a covalently connected linker element at the 5' end and/or the 3' end of the Cas9-associated first NATNA and/or the Cas9-associated second NATNA.

Embodiment 6

The engineered three-element NATNA of embodiment 1 or 2, wherein the Cpf1-associated NATNA is connected with the 5' end or the 3' end of the Cas9-associated first NATNA, or the 5' end or the 3' end of the Cas9-associated second NATNA, and the connection is through a covalent bond.

Embodiment 7

The engineered three-element NATNA of embodiment 6, wherein the Cpf1-associated NATNA further comprises a covalently connected linker element at the 5' end and/or the 3' end of the Cpf1-associated NATNA.

Embodiment 8

The engineered three-element NATNA of embodiment 6 or 7, wherein the Cas9-associated first NATNA and/or the Cas9-associated second NATNA further comprises a covalently connected linker element at the 5' end and/or the 3' end of the Cas9-associated first NATNA and/or the Cas9-associated second NATNA.

Embodiment 9

The engineered three-element NATNA of embodiment 1 or 2, wherein the 3' end of the Cas9-associated first NATNA is covalently connected through a loop element with the 5' end of the Cas9-associated second NATNA forming a single-Cas9-associated NATNA having a 5' end and a 3' end; and wherein the Cpf1-associated NATNA is connected with the 5' end or 3' end of the single-Cas9-associated NATNA, and the connection is through hydrogen bonding.

Embodiment 10

The engineered three-element NATNA of embodiment 9, wherein the Cpf1-associated NATNA further comprises a covalently connected linker element at the 5' end and/or the 3' end of the Cpf1-associated NATNA.

Embodiment 11

The engineered three-element NATNA of embodiment 9 or 10, wherein the single-Cas9-associated NATNA further comprises a covalently connected linker element at the 5' end and/or the 3' end of the single-Cas9-associated NATNA.

Embodiment 12

The engineered three-element NATNA of embodiment 1 or 2, wherein the 3' end of the Cas9-associated first NATNA is covalently connected through a loop element with the 5' end of the Cas9-associated second NATNA forming a single-Cas9-associated NATNA; and wherein the Cpf1-associated NATNA is connected with the 5' end or 3' end of the single-Cas9-associated nucleic-acid targeting nucleic, and the connection is through a covalent bond.

Embodiment 13

The engineered three-element NATNA of embodiment 12, wherein the Cpf1-associated NATNA further comprises a covalently connected linker element at the 5' end and/or of the 3' end the Cpf1-associated NATNA.

Embodiment 14

The engineered three-element NATNA of embodiment 12 or 13, wherein the single-Cas9-associated NATNA further comprises a covalently connected linker element at the 5' end and/or the 3' end of the single-Cas9-associated NATNA.

Embodiment 15

The engineered three-element NATNA of any preceding embodiment, wherein at least one of the following elements comprises a RNA: a Cpf1-associated NATNA; a Cas9-associated first NATNA; or a Cas9-associated second NATNA.

Embodiment 16

The engineered three-element NATNA of any preceding embodiment, wherein at least one of the following elements comprises a DNA: a Cpf1-associated NATNA; a Cas9-associated first NATNA; or a Cas9-associated second NATNA.

Embodiment 17

A nucleic acid/protein composition comprising:
the engineered three-element NATNA of any preceding embodiment, a Cas9 protein, and a Cpf1 protein.

Embodiment 18

The nucleic acid/protein composition of embodiment 17, wherein the engineered three-element NATNA forms a complex with the Cas9 protein and the Cpf1 protein.

Embodiment 19

The nucleic acid/protein composition of embodiment 18, wherein the Cpf1 protein is inactive for endonuclease activity.

Embodiment 20

The nucleic acid/protein composition of embodiment 19, further comprising a donor polynucleotide wherein the donor polynucleotide comprises a nucleotide sequence complementary to the Cpf1-associated NATNA spacer element.

Embodiment 21

The nucleic acid/protein composition of embodiment 20, wherein the Cpf1-associated NATNA spacer element is connected with the donor polynucleotide by hydrogen bonding between the donor polynucleotide nucleotide sequence complementary to the spacer element and the spacer element.

Embodiment 22

The nucleic acid/protein composition of embodiment 18, wherein the Cas9 protein is inactive for endonuclease activities.

Embodiment 23

The nucleic acid/protein composition of embodiment 22, further comprising a donor polynucleotide wherein the donor polynucleotide comprises a nucleotide sequence complementary to the Cas9-associated first NATNA spacer element.

Embodiment 24

The nucleic acid/protein composition of embodiment 23, wherein the Cas9-associated first NATNA spacer element is connected with the donor polynucleotide by hydrogen bonding between the donor polynucleotide nucleotide sequence complementary to the spacer element and the spacer element.

Embodiment 25

The nucleic acid/protein composition of embodiment 18, wherein the Cas9 protein is inactive for endonuclease activities and the Cpf1 protein is inactive for endonuclease activity.

Embodiment 26

One or more vectors comprising: nucleotide sequences encoding the engineered three-element NATNA of any of embodiments 1 to 16.

Embodiment 27

A recombinant cell comprising: the one or more vectors of embodiment 26.

Embodiment 28

A recombinant cell comprising: the engineered three-element NATNA of any of embodiments 1 to 16.

Embodiment 29

A recombinant cell comprising: the nucleic acid/protein composition of any one of embodiments 17 to 25.

Embodiment 30

The recombinant cell of any of embodiments 27 to 29, wherein the cell is a plant cell, a yeast cell, a bacterial cell, an insect cell, an algal cell, or a mammalian cell.

Embodiment 31

A method of modifying DNA comprising:
contacting a first DNA target sequence in the DNA and a second DNA target sequence in the DNA with the nucleic acid/protein composition of embodiment 18,
wherein the first DNA target sequence is complementary to the Cas9-associated first NATNA spacer element, the second DNA target sequence is complementary to the Cpf1-associated NATNA spacer element, the nucleic acid/protein composition binds to the first DNA target sequence and the second DNA target sequence, and the Cas9 protein and the Cpf1 protein cut the first DNA target sequence and the second DNA target sequence, respectively, resulting in a modification of the DNA.

Embodiment 32

A method of modifying DNA comprising:
contacting a first DNA target sequence in the DNA and a second DNA target sequence in a donor polynucleotide with the nucleic acid/protein composition of embodiment 21,
wherein the first DNA target sequence is complementary to the Cas9-associated first NATNA spacer element, the second DNA target sequence is complementary to the Cpf1-associated NATNA spacer element, the nucleic acid/protein composition binds to the first DNA target sequence, the Cas9 protein cuts the first DNA target sequence, and at least a portion of the donor polynucleotide is introduced into the DNA resulting in a modification of the DNA.

Embodiment 33

A method of modifying DNA comprising:
  contacting a first DNA target sequence in a donor polynucleotide and a second DNA target sequence in the DNA with the nucleic acid/protein composition of embodiment 24,
  wherein the first DNA target sequence is complementary to the Cas9-associated first NATNA spacer element, the second DNA target sequence is complementary to the Cpf1-associated NATNA spacer element, the nucleic acid/protein composition binds to the second DNA target sequence, the Cpf1 protein cuts the second DNA target sequence, and at least a portion of the donor polynucleotide is introduced into the DNA resulting in a modification of the DNA.

Embodiment 34

A method of bringing a first DNA target site into the proximity of a second DNA target site comprising:
  contacting a first DNA target sequence and a second DNA target sequence with the nucleic acid/protein composition of embodiment 25,
  wherein the first DNA target sequence is complementary to the Cas9-associated first NATNA spacer element, the second DNA target sequence is complementary to the Cpf1-associated NATNA spacer element, the nucleic acid/protein composition binds to the first DNA target sequence and the second DNA target sequence bringing the first DNA target site into the proximity of the second DNA target sequence.

Embodiment 35

The method of embodiment 34, wherein the first DNA target sequence and the second DNA target sequence are on separate polynucleotides.

Embodiment 36

A method of modulating transcription of a gene comprising regulatory element sequences, comprising:
  contacting a first DNA target sequence and a second DNA target sequence with the nucleic acid/protein composition of embodiment 25,
  wherein the first DNA target sequence is complementary to the Cas9-associated first NATNA spacer element, the second DNA target sequence is complementary to the Cpf1-associated NATNA spacer element, at least one of the first DNA target sequence or the second DNA target sequence comprise the regulatory element sequences, the nucleic acid/protein composition binds to the first DNA target sequence and the second DNA target sequence, and the binding of the nucleic acid/protein composition modulates transcription of the gene.

Although preferred embodiments of the present invention have been shown and described herein, it will be obvious to those skilled in the art that such embodiments are provided by way of example only. From the above description and the following Examples, one skilled in the art can ascertain essential characteristics of this invention and, without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are illustrated in the following Examples. Efforts have been made to ensure accuracy with respect to numbers used (e.g., amounts, concentrations, percent changes, and the like) but some experimental errors and deviations should be accounted for. Unless indicated otherwise, temperature is in degrees Centigrade and pressure is at or near atmospheric. It should be understood that these Examples are given by way of illustration only and are not intended to limit the scope of what the inventors regard as various aspects of the present invention.

Materials and Methods

Sequences of oligonucleotide sequences) were provided to commercial manufacturers for synthesis.

Engineered cross-type-nucleic-acid targeting nucleic acids ("cross-type-NATNAs"; e.g., engineered Cas9-Cpf1 nucleic-acid targeting nucleic acids ("Cas9-Cpf1-NATNAs")) were assembled by PCR using 3' overlapping primers containing DNA sequences corresponding to a cross-type-NATNA.

Example 1

Production of Components of Cross-Type-Nucleic-Acid Targeting Nucleic Acids

This Example describes production of cross-type-NATNAs, for example, a Cas9-Cpf1-NATNA similar to the Cas9-Cpf1-NATNA illustrated in FIG. 4. The Cas9-Cpf1-NATNA was designed with a spacer that targeted the coding sequences for vascular endothelial growth factor A (VEGFA) incorporated upstream (e.g., in a 5' direction) to the Cas9-sgRNA backbone component and a spacer that targeted the coding sequences for an indoleamine 2,3-dioxygenase 2 (IDO2) incorporated downstream (e.g., in a 3' direction) to the Cpf1 guide RNA backbone component. The Cas9-Cpf1-NATNA was designed such that the 3' end of the Cas9 guide RNA sequence was linked (through a covalent bond) to the 5' end of the Cpf1 guide RNA sequence to create a single polynucleotide with a continuous polynucleotide backbone (e.g., FIG. 4).

RNA components were produced by in vitro transcription (e.g., T7 Quick High Yield RNA Synthesis Kit, New England Biolabs, Ipswich, Mass.) from a double-stranded DNA template incorporating a T7 promoter at the 5' end of the DNA sequences.

The double-stranded DNA template for the specific Cas9-Cpf1-NATNA ("Cas9-Cpf1-NATNA$_1$") component used in the following Examples was assembled by PCR using 3' overlapping primers containing the corresponding DNA sequences to the Cas9-Cpf1-NATNA$_1$ component. The oligonucleotides used in the assembly are presented in Table 1.

TABLE 1

Overlapping Primers for Generation of
Cas9-Cpf1-NATNA$_1$-Encoding Template

| SEQ ID NO. | Sequence* |
|---|---|
| SEQ ID NO. 1 | AGTGTAATACGACTCACTATAG |
| SEQ ID NO. 2 | TAATACGACTCACTATAGGGGTGGGGGAGTTTGCT CCGTTTTAGAGCTAGAAATAGCAAGTTGAGATAAGG CTAGTCCGTTATCAACTTG |

TABLE 1-continued

Overlapping Primers for Generation of
Cas9-Cpf1-NATNA$_1$-Encoding Template

| SEQ ID NO. | Sequence* |
|---|---|
| SEQ ID NO. 3 | CCAGGCACTGCTTCTTTCTCTACCATCTACAACAGT<u>AGAAATTAAGCACCGACTCGGTGCCACTTTTTCAAG</u>TTGATAACGGACTAGCCTT |
| SEQ ID NO. 4 | CCAGGCACTGCTTCTTTCTCTACC |

*Spacers are underlined

The DNA primers were present at a concentration of 2 nM each. Two outer DNA primers corresponding to the T7 promoter (SEQ ID NO. 1) and the 3' end of the RNA sequence (SEQ ID NO. 4) were used at 640 nM to drive the amplification reaction. PCR reactions were performed using Q5 Hot Start High-Fidelity 2X Master Mix (New England Biolabs, Ipswich, Mass.) following the manufacturer's instructions. PCR assembly reactions were carried out using the following thermal cycling conditions: 98° C. for 2 minutes, 35 cycles of 15 seconds at 98° C., 15 seconds at 60° C., 15 seconds at 72° C., and a final extension at 72° C. for 2 minutes. DNA quality was evaluated by agarose gel electrophoresis (1.5%, SYBR® Safe; Life Technologies, Grand Island, N.Y.).

Between 0.25-0.5 μg of the DNA template for the Cas9-Cpf1-NATNA$_1$ component was transcribed using T7 High Yield RNA Synthesis Kit (New England Biolabs, Ipswich, Mass.) for approximately 16 hours at 37° C. Transcription reactions were treated with DNase I (New England Biolabs, Ipswich, Mass.) and purified using GeneJet RNA Cleanup and Concentration Kit (Life Technologies, Grand Island, N.Y.). RNA yield was quantified using a Nanodrop™ 2000 System (Thermo Scientific, Wilmington, Del.). The quality of the transcribed RNA was checked by agarose gel electrophoresis (2%, SYBR® Safe; Life Technologies, Grand Island, N.Y.). The Cas9-Cpf1-NATNA$_1$ sequence is shown in Table 2.

TABLE 2

Cas9-Cpf1-NATNA$_1$ Sequence

| SEQ ID NO. | Sequence* |
|---|---|
| SEQ ID NO. 5 | GGGUGGGGGAGUUUGCUCCGUUUUAGAGCUAGAAAUAGCAAGUUGAGAUAAGGCUAGUCCGUUAUCAACUUGAAAAA<u>GUGGCACCGAGUCGGUGCUUAAUUUCUACUGUUGUAGAU</u>GGUAGAGAAAGAAGCAGUGCCUGG |

*Spacers are underlined

This method for production of Cas9-Cpf1-NATNA$_1$ can be applied to the production of other cross-type-NATNAs described herein.

Example 2

Production of Double-Stranded DNA Target Sequences for Use in Cleavage Assays

Double-stranded DNA target sequences for use in in vitro Cas cleavage assays were produced using PCR amplification of selected nucleic acid target sequences from human genomic DNA.

Double-stranded DNA target sequences (e.g., VEGFA and IDO2) for biochemical assays were amplified by PCR from phenol-chloroform prepared human cell line K562 (American Type Culture Collection (ATCC), Manassas, Va.) genomic DNA (gDNA). PCR reactions were carried out with Q5 Hot Start High-Fidelity 2X Master Mix (New England Biolabs, Ipswich, Mass.) following the manufacturer's instructions. 20 ng/μL gDNA in a final volume of 25 μl were used to amplify the selected nucleic acid target sequence under the following conditions: 98° C. for 2 minutes, 35 cycles of 20 seconds at 98° C., 20 seconds at 60° C., 20 seconds at 72° C., and a final extension at 72° C. for 2 minutes. PCR products were purified using Spin Smart™ PCR purification tubes (Denville Scientific, South Plainfield, N.J.) and quantified using a Nanodrop™ 2000 UV-Vis spectrophotometer (Thermo Scientific, Wilmington, Del.).

The forward and reverse primers used for amplification of selected targeted sequences from gDNA are presented in Table 3.

TABLE 3

Double-Stranded DNA Target
Sequence Primer Sequences

| SEQ ID NO. | Sequence |
|---|---|
| SEQ ID NO. 6 | CACTCTTTCCCTACACGACGCTCTTCCGATCTCCAGATGGCACATTGTCAGA |
| SEQ ID NO. 7 | GGAGTTCAGACGTGTGCTCTTCCGATCTCCTAGTGACTGCCGTCTGC |
| SEQ ID NO. 8 | CACTCTTTCCCTACACGACGCTCTTCCGATCTAAGGAACCTGGAGACCATCA |
| SEQ ID NO. 9 | GGAGTTCAGACGTGTGCTCTTCCGATCTGAAAGGCACTGAGTGGGAAG |

The VEGFA DNA target sequences were amplified using SEQ ID NO. 6 and SEQ ID NO. 7, yielding a 261 bp double-stranded DNA target sequence. IDO2 DNA target sequences were amplified using SEQ ID NO. 8 and SEQ ID NO. 9, yielding a 232 bp double-stranded DNA target sequence.

Other suitable double-stranded DNA target sequences can be obtained using essentially the same method. For non-human nucleic acid target sequences, genomic DNA from the selected organism (e.g., plant, bacteria, yeast, algae) can be used instead of DNA derived from human cells. Furthermore, polynucleotide sources other than genomic DNA can be used (e.g., vectors and gel isolated DNA fragments).

Example 3

Cas Cleavage Assays

This Example illustrates the use of Cas protein/cross-type-NATNAs in cleavage assays.

In this Example, a Cas9-Cpf1-NATNA$_1$/Cas9 protein complex and a Cas9-Cpf1-NATNA$_1$/Cpf1 protein complex were used in in vitro Cas9 or Cpf1 cleavage assays, respectively, to evaluate and compare the percent cleavage of selected Cas9-Cpf1-NATNA$_1$/Cas9 protein complexes and Cas9-Cpf1-NATNA$_1$/Cpf1 protein complexes relative to selected double-stranded DNA target sequences.

The cleavage of double-stranded DNA target sequences was determined using the Cas9-Cpf1-NATNA$_1$ components of Example 1, with one or more cognate Cas proteins to form a complex, against a double-stranded DNA target sequence (VEGFA and IDO2; Example 2).

*S. pyogenes* Cas9 and *F. novicida* Cpf1 were recombinantly expressed in *E. coli* and purified for use in an in vitro biochemical cleavage assay.

The Cas9-Cpf1-NATNA$_1$ components were diluted to a suitable working concentration and incubated for 2 minutes at 95° C., removed from a thermocycler and allowed to equilibrate to room temperature.

Cas9-Cpf1-NATNA$_1$ was added to either a Cas9 reaction mix or a Cpf1 reaction mix. The Cas9 reaction mix comprised Cas9 protein diluted to a final concentration of 20 nM in reaction buffer (20 mM HEPES, 100 mM KCl, 5 mM MgCl$_2$, 1 mM DTT, and 5% glycerol at pH 7.4). The Cpf1 reaction mix comprised Cpf1 protein diluted to a final concentration of 50 nM in reaction buffer (20 mM HEPES, 100 mM KCl, 5 mM MgCl$_2$, 1 mM DTT, and 5% glycerol at pH 7.4). In the reaction mix, the final concentration of Cas9-Cpf1-NATNA$_1$ was as follows: 200 nM in the Cas9 reaction mix and 500 nM in the Cpf1 reaction mix. Each reaction mix was incubated at 37° C. for 10 minutes. The cleavage reaction was initiated by the addition of the DNA target sequence to a final concentration of 10 nM. Samples were mixed and centrifuged briefly before being incubated for 15 minutes at 37° C. Cleavage reactions were terminated by the addition of Proteinase K (Denville Scientific, South Plainfield, N.J.) at a final concentration of 0.2 μg/μL and 0.44 mg/μL RNase A Solution (SigmaAldrich, St. Louis, Mo.). Samples were then incubated for 25 minutes at 37° C. and 25 minutes at 55° C. 12 μL of the total reaction were evaluated for cleavage activity by agarose gel electrophoresis (2%, SYBR® Gold; Life Technologies, Grand Island, N.Y.). For the Cas9 cleavage of a VEGFA double-stranded DNA target sequence, the appearance of DNA bands at approximately 158 bp and approximately 103 bp indicated that cleavage of the DNA target sequence had occurred. For the Cpf1 cleavage of an IDO2 double-stranded DNA target sequence, the appearance of DNA bands at approximately 120 bp and approximately 112 bp indicated that cleavage of the DNA target sequence had occurred. Cleavage percentages were calculated using area under the curve (AUC) values as calculated by FIJI (ImageJ; an open source Java image processing program) for each cleavage fragment and the DNA target sequence, and dividing the sum of the cleavage fragments by the sum of both the cleavage fragments and the DNA target sequences.

Table 4 presents the results of the Cas9 and Cpf1 cleavage assays using nucleic acid target sequences VEGFA and IDO2 double-stranded DNA target sequences.

TABLE 4

Biochemical Cleavage of DNA Target Sequence with a Cas9-Cpf1-NATNA

| | Cas9 VEGFA DNA target sequence cleavage | Cpf1 IDO2 DNA target sequence cleavage |
|---|---|---|
| Cas9-Cpf1-NATNA$_1$ | 93% | 68% |

The data presented in Table 4 demonstrate that the Cas9-Cpf1-NATNA$_1$ of the present invention facilitated Cas protein mediated site-specific cleavage of double-stranded DNA target sequences. The data also showed that a single-Cas9-Cpf1-NATNA can be used with either a Cas9-nuclease or a Cpf1-nuclease to facilitate the targeted cleavage of a double-stranded DNA target sequence.

Following the guidance of the present specification and Examples, the biochemical cleavage assay described in this Example can be practiced by one of ordinary skill in the art with other cross-type-NATNAs and their cognate Cas proteins (e.g., Type II CRISPR Cas9 proteins or Type V CRISPR Cpf1 proteins).

Example 4

Deep Sequencing Analysis for Detection of Target Sequence Modifications in Eukaryotic Cells This Example illustrates the use of deep sequencing analysis to evaluate and compare the percent cleavage in cells of cross-type-NATNA/Cas protein complexes relative to selected double-stranded DNA target sequences.

A. Design of a Cas9-Cpf1-NATNA

The human epidermal receptor growth factor 2 (ERBB2) locus was scanned for 20 nucleotide Cas9 protospacer sequences occurring upstream of a 5'-NGG PAM sequence and a 24 nucleotide Cpf1 protospacer sequence occurring downstream of a 3'-TTTN PAM sequence. Examples of protospacer sequences selected by this method are shown in Table 5.

TABLE 5

ERBB2 Cas9 and Cpf1 Protospacer Sequences

| Name | SEQ ID NO. | Sequence* | Hg38 chromosomal coordinates |
|---|---|---|---|
| Cas9 ERBB2 protospacer | SEQ ID NO. 10 | GTGCCCTCGGTCACAC TGTG<u>TGG</u> | chr17:39727008-39727030 |
| Cpf1 ERBB2 protospacer | SEQ ID NO. 11 | <u>TTTC</u>TCTGATGTTCCC TCAACTGTCACC | chr17:39727072-39727099 |

*Nuclease-specific PAMs are underlined

The Cas9 spacer sequence (i.e., the protospacer sequence without the PAM) was incorporated upstream 5' to a Cas9 sgRNA backbone component and the Cpf1 spacer sequence (i.e., the protospacer sequence without the PAM) was incorporated downstream 3' to a Cpf1 guide RNA backbone component to form the cross-type-NATNA ERBB2-Cas9-Cpf1-NATNA. The RNA sequence for this ERBB2-Cas9-Cpf1-NATNA is shown in Table 6.

TABLE 6

ERBB2-Cas9-Cpf1-NATNA Sequence

| SEQ ID NO. | Sequence* |
|---|---|
| SEQ ID NO. 12 | GUGCCCUCGGUCACACUGUGGUUUUAGAGCUAGAAAUAGCA AGUUGAGAUAAGGCUAGUCCGUUAUCAACUUGAAAAAGUGG CACCGAGUCGGUGCUUAAUUUCUACUGUUGUAGAU<u>UCUGAU</u> <u>GUUCCCUCAACUGUCACC</u> |

*Nuclease-specific spacers are underlined

Following the guidance of the present specification and Examples, additional cross-type-NATNAs can be designed by one of ordinary skill in the art.

B. Formation of ERBB2-Cas9-Cpf1-NATNA/Cas9&Cpf1 Protein Nucleoprotein Complexes

Primers to assemble the ERBB2-Cas9-Cpf1-NATNA can be ordered from a commercial manufacturer, and the ERBB2-Cas9-Cpf1-NATNA can be assembled essentially as described in Example 1. The RNA sequence for an exemplary ERBB2-Cas9-Cpf1-NATNA is shown in Table 6. *S.*

*pyogenes* Cas9 and *Acidaminococcus* sp. Cpf1 are both C-terminally tagged with two nuclear localization sequences (NLS) and are recombinantly expressed in *E. coli*. Ribonucleoprotein (RNP) complexes are formed at a concentration of 40 pmol Cas9 protein:40 pmol Cpf1 protein:120 pmols ERBB2-Cas9-Cpf1-NATNA. Prior to assembly with the Cas9 and Cpf1 proteins, the ERBB2-Cas9-Cpf1-NATNA is diluted to the desired concentration (120 pmol) in a final volume of 2 µL, incubated for 2 minutes at 95° C., removed from a thermocycler, and allowed to equilibrate to room temperature. Cas9 and Cpf1 proteins are diluted to an appropriate concentration in binding buffer (20 mM HEPES, 100 mM KCl, 5 mM MgCl$_2$, 1 mM DTT, and 5% glycerol at pH 7.4) to a final volume of 3 µL and are mixed with the 2 µL of ERBB2-Cas9-Cpf1-NATNA followed by incubation at 37° C. for 30 minutes.

C. Cell Transfections Using ERBB2-Cas9-Cpf1-NATNA/Cas9&Cpf1 RNP

RNP complexes are transfected into HEK293 cells (ATCC, Manassas Va.), using the Nucleofector® 96-well Shuttle System (Lonza, Allendale, N.J.) and the following protocol. RNP complexes are dispensed in a 5 µL final volume into individual wells of a 96-well plate. The cell culture medium is removed from the HEK293 cell culture plate and the cells are detached with TrypLE™ (Thermo Fisher Scientific, Waltham, Mass.). Suspended HEK293 cells are pelleted by centrifugation for 3 minutes at 200×g, TrypLE reagents is aspirated, and cells are washed with calcium and magnesium-free phosphate buffered saline (PBS). Cells are pelleted by centrifugation for 3 minutes at 200×g, the PBS is aspirated, and the cell pellet is re-suspended in 10 mL of calcium and magnesium-free PBS.

The cells can be counted using the Countess® II Automated Cell Counter (Life Technologies; Grand Island, N.Y.). 2.2×10$^7$ cells are transferred to a 1.5 ml microfuge tube and pelleted. The PBS is aspirated and the cells are re-suspended in Nucleofector™ SF (Lonza, Allendale, N.J.) solution to a density of 1×10$^7$ cells/mL. 20 µL of the cell suspension are then added to each individual well containing 5 µL of RNP complexes, and the entire volume from each well is transferred to a well of a 96-well Nucleocuvette™ Plate (Lonza, Allendale, N.J.). The plate is loaded onto the Nucleofector™ 96-well Shuttle™ (Lonza, Allendale, N.J.) and cells are nucleofected using the 96-CM-130 Nucleofector™ program (Lonza, Allendale, N.J.). Post-nucleofection, 70 µL Dulbecco's Modified Eagle Medium (DMEM; Thermo Fisher Scientific, Wilmington, Del.), supplemented with 10% Fetal Bovine Serum (FBS; Thermo Fisher Scientific, Wilmington, Del.), penicillin and streptomycin (Life Technologies, Grand Island, N.Y.), are added to each well and then 50 µL of the cell suspension are transferred to a 96-well cell culture plate containing 150 µL pre-warmed DMEM complete culture medium. The plate is then transferred to a tissue culture incubator and maintained at 37° C. in 5% CO$_2$ for 48 hours.

D. Double-Stranded DNA Target Sequence Generation for Deep Sequencing gDNA is isolated from the HEK293 cells 48 hours after transfection using the RNP complexes and 50 µL QuickExtract DNA Extraction solution (Epicentre, Madison, Wis.) per well, followed by incubation at 37° C. for 10 minutes, 65° C. for 6 minutes and 95° C. for 3 minutes to stop the reaction. The isolated gDNA is then diluted with 504, sterile water and samples are stored at −80° C.

Using the isolated gDNA, a first PCR is performed using Q5 Hot Start High-Fidelity 2X Master Mix (New England Biolabs, Ipswich, Mass.) at 1× concentration, primers at 0.5 µM each (SEQ ID NO. 13 and SEQ ID NO. 14), 3.75 µL of gDNA in a final volume of 104, and amplified 98° C. for 1 minute, 35 cycles of 10 s at 98° C., 20 seconds at 60° C., 30 seconds at 72° C., and a final extension at 72° C. for 2 minutes. Primers are designed to amplify the region of the genome targeted by the ERBB2-Cas9-Cpf1-NATNA. The PCR reaction is diluted 1:100 in water.

Barcoding PCR is performed using a reaction mix comprising Q5 Hot Start High-Fidelity 2X Master Mix (New England Biolabs, Ipswich, Mass.) at 1× concentration; primers at 0.5 µM each (SEQ ID NO. 15 and SEQ ID NO. 16); 1 µL of 1:100 diluted first PCR; in a final volume of 10 µL; and the reaction mix is amplified 98° C. for 1 minute, followed 12 cycles of 10 s at 98° C., 20 seconds at 60° C., and 30 seconds at 72° C., with a final extension reaction performed at 72° C. for 2 minutes.

E. SPRIselect Clean-Up

The PCR reaction is transferred into a single microfuge tube for SPRIselect (Beckman Coulter, Pasadena, Calif.) bead-based cleanup of amplicons for sequencing.

To the amplicon, 0.9× volumes of SPRIselect beads are added, mixed, and incubated at room temperature (RT) for 10 minutes. The microfuge tube is placed on magnetic tube stand (Beckman Coulter, Pasadena, Calif.) until the solution clears. Supernatant is removed and discarded, and the residual beads are washed with 1 volume of 85% ethanol, and incubated at RT for 30 seconds. After incubation, ethanol is aspirated and beads are air dried at RT for 10 minutes. The microfuge tube is then removed from the magnetic stand and 0.25× volumes of Qiagen EB buffer (Qiagen, Venlo, Netherlands) is added to the beads, mixed vigorously, and incubated for 2 minutes at room temperature. The microfuge tube is returned to the magnet, incubated until the solution had cleared, and supernatant containing the purified amplicons is dispensed into a clean microfuge tube. The purified amplicon is quantified using a Nanodrop™ 2000 System (Thermo Scientific, Wilmington Del.) and library quality is analyzed using the Fragment Analyzer™ System (Advanced Analytical Technologies, Ames, Iowa) and the DNF-910 Double-stranded DNA Reagent Kit (Advanced Analytical Technologies, Ames, Iowa).

F. Deep Sequencing Set-Up

The amplicon is normalized to a 4 nM concentration as calculated from Nanodrop values and size of the amplicons. The library is analyzed on MiSeq Sequencer (Illumina, San Diego, Calif.) with MiSeq Reagent Kit v2 (Illumina, San Diego, Calif.) for 300 cycles with two 151-cycle paired-end runs plus two eight-cycle index reads.

G. Deep Sequencing Data Analysis

The identity of products in the sequencing data is determined based on the index barcode sequences adapted onto the amplicons in the barcoding round of PCR. A computational script is used to process the MiSeq data that executes, for example, the following tasks:

Reads are aligned to the human genome (build GRCh38/38) using Bowtie (bowtie-bio.sourceforge.net/index.shtml) software.

Aligned reads are compared to the expected wild-type ERBB2 locus sequence, and reads not aligning to any part of the ERBB2 locus are discarded.

Reads matching wild-type ERBB2 sequence are tallied.

Reads with indels (insertion or deletion of bases) are categorized by indel type and tallied.

Total indel reads are divided by the sum of wild-type reads and indel reads to give percent-mutated reads.

Through the identification of indel sequences at the regions targeted by the ERBB2-Cas9-Cpf1-NATNA/

Cas9&Cpf1 protein RNP complexes, sequence-specific targeting in a human cell line can be determined. The relative distance between the two nucleic acid target sequence sites in the ERBB2 locus can result in excision of the sequence between the Cas9 and Cpf1 nucleic acid target sequences.

Following the guidance of the present specification and Examples, the in cell editing of a genomic sequence can be practiced by one of ordinary skill in the art with other Cas proteins and their cognate cross-type-NATNAs.

Example 5

Identification and Screening of crRNAs

This Example describes a method to identify Class 2 crRNAs in different bacterial species.

This Example describes a method by which crRNAs of species having a Class 2 CRISPR system are identified. The method presented here is adapted from Chylinski, K., et al., RNA Biology 10(5):726-37 (2013). Not all of the following steps are required for screening nor must the order of the steps be as presented.

A. Identify a Species Containing a Class 2 CRISPR Locus

Using the Basic Local Alignment Search Tool (BLAST, blast.ncbi.nlm.nih.gov/Blast.cgi), a search of the genomes of various species is conducted to identify Class 2 CRISPR Cas nucleases, (e.g., Cas9 protein, Cpf1 protein, Cas9-like proteins, Cpf1-like proteins, etc.). Class 2 CRISPR systems exhibit a high diversity in sequence across species, however Class 2 CRISPR nuclease orthologs have conserved domains, for example, an HNH endonuclease domain and/or a RuvC/RNase H domain. Primary BLAST results are filtered for identified domains, incomplete or truncated sequences are discarded, and species having Class 2 CRISPR nuclease orthologs are identified.

If a Class 2 CRISPR nuclease ortholog is identified in a species, sequences adjacent to the Cas protein ortholog-coding sequence (e.g., Cas9 protein or Cpf1 protein) are probed for other Cas proteins and a Cas-associated repeat-spacer array is used to identify all sequences belonging to the CRISPR-Cas locus. This may be done by alignment to other known Class 2 CRISPR loci.

Once the sequence of the Class 2 CRISPR locus for the nuclease ortholog is identified for the species, in silico predictive screening is used to extract the crRNA sequence. The crRNA sequence is contained within CRISPR repeat array and can be identified by its hallmark repeating sequences interspaced by foreign spacer sequences.

B. Preparation of RNA-Seq Library

The putative CRISPR array containing the individual crRNA identified in silico is further validated using RNA sequencing (RNA-seq).

Cells from species identified as comprising putative crRNA are procured from a commercial repository (e.g., ATCC, Manassas, Va.; German Collection of Microorganisms and Cell Cultures GmbH (DSMZ), Braunschweig, Germany).

Cells are grown to mid-log phase and total RNA prepped using Trizol reagent (SigmaAldrich, St. Louis, Mo.) and treated with DNaseI (Fermentas, Vilnius, Lithuania).

10 ug of the total RNA is treated with Ribo-Zero rRNA Removal Kit (Illumina, San Diego, Calif.) and the remaining RNA purified using RNA Clean and Concentrators (Zymo Research, Irvine, Calif.).

A library is then prepared using a TruSeq Small RNA Library Preparation Kit (Illumina, San Diego, Calif.) following the manufacturer's instructions. This results in cDNAs having adapter sequences.

The resulting cDNA library is sequenced using MiSeq Sequencer (Illumina, San Diego, Calif.).

C. Processing of Sequencing Data

Sequencing reads of the cDNA library are processed, for example, using the following method.

Adapter sequences are removed using cutadapt 1.1 (pypi.python.org/pypi/cutadapt/1.1) and about 15 nt are trimmed from the 3'end of the read to improve read quality.

Reads are aligned to the genome of the respective species (i.e., from which the putative crRNA was identified) with a mismatch allowance of 2 nucleotides.

Read coverage is calculated using BedTools (bedtools.readthedocs.org/en/latest/).

Integrative Genomics Viewer (IGV; www.broad-institute.org/igv/) is used to map the starting (5') and ending (3') position of reads. Total reads retrieved for the putative crRNA are calculated from the SAM file of alignments.

The RNA-seq data is used to validate that a putative crRNA element is actively transcribed in vivo. Confirmed hits from comparison of the in silico and RNA-seq screens are validated for functional ability to support Class 2 CRISPR nuclease cleavage of a double-stranded DNA target nucleic acid sequences using the methods outline herein (e.g., Examples 1, 2, and 3). It is known in the art that the Type V system only requires a crRNA to facilitate Cpf1 nuclease cleavage of a double-stranded DNA target sequence, whereas the Type II system requires a crRNA and a cognate tracrRNA to facilitate Cas9 nuclease cleavage of a double-stranded DNA target sequence. The cognate tracrRNA can be identified following the method described in Example 6.

Following the guidance of the present specification and Examples, the identification of novel crRNA sequences related to Cas proteins can be practiced by one of ordinary skill in the art.

Example 6

Identification and Screening of tracrRNA

This Example illustrates a method by which tracrRNAs of species having, for example, a Class 2 Type II CRISPR-Cas9 system can be identified. This is adapted from Chylinski, K., et al., RNA Biology 10(5):726-737 (2013). Not all of the following steps are required for screening nor must the order of the steps be as presented.

A. Identify a Species Containing a CRISPR-Cas9 Type-II System

Using the Basic Local Alignment Search Tool (BLAST, blast.ncbi.nlm.nih.gov/Blast.cgi), a search of the genomes of various species is conducted to identify a Cas9 protein. Class 2 Type II CRISPR-Cas9 systems exhibit a high diversity in sequence across species, however Cas9 orthologs exhibit conserved domain architectures of a central HNH endonuclease domain and a split RuvC/RNase domain. Primary BLAST results are filtered for identified domains; incomplete or truncated sequences are discarded and Cas9 orthologs are identified.

If a Cas9 ortholog is identified in a species, sequences adjacent to the Cas9 ortholog-coding sequence are probed for other Cas proteins and a Cas-associated repeat-spacer array to identify all sequences belonging to the CRISPR-Cas9 locus. This may be done by alignment to other known Class 2 Type II CRISPR-Cas9 loci, with the knowledge that closely related species exhibit similar CRISPR-Cas9 locus architecture (e.g., Cas protein composition, size, orientation, location of array, location of tracrRNA, and so on). The tracrRNA element is typically contained within the Class 2 Type II CRISPR-Cas9 locus and is readily identified by its sequence complementarity to the repeat elements in the repeat-spacer array. The tracr sequences complementary to the repeat elements are called the tracr anti-repeat sequences.

Once the sequence of the CRISPR-Cas9 locus corresponding to the Cas9 ortholog is identified for a species, in silico predictive screening is used to extract the tracr anti-repeat sequence to identify the Cas-associated tracrRNA. Putative anti-repeats are screened, for example, as follows.

If the repeat sequence is from a known species, it is identified in and retrieved from the CRISPRdb database (crispr.u-psud.fr/crispr/). If the repeat sequence is not known to be related to a species, repeat sequences are predicted employing CRISPRfinder software (crispr.u-psud.fr/Server/) using the Class 2 Type II CRISPR-Cas9 locus for the species as described above.

The identified repeat sequence for the species is used to probe the CRISPR-Cas9 locus for the anti-repeat sequence (e.g., using the BLASTp algorithm or the like). The search is typically restricted to intergenic regions of the CRISPR-Cas9 locus.

An identified tracr anti-repeat region is validated for complementarity to the identified repeat sequence.

A putative anti-repeat region is probed in the regions 5' and 3' of the putative anti-repeat region for the presence of a Rho-independent transcriptional terminator (TransTerm HP, transterm.cbcb.umd.edu/).

By combining the identified sequence comprising the anti-repeat element and the Rho-independent transcriptional terminator the sequence is determined to be the putative tracrRNA of the given species.

B. Preparation of RNA-Seq Library

The in silico identified, putative tracrRNA is further validated using RNA sequencing (RNA-seq).

Cells from species comprising the putative tracrRNA are procured from a commercial repository (e.g., ATCC, Manassas Va.; DSMZ, Braunschweig, Germany).

Cells are grown to mid-log phase and total RNA prepared using Trizol reagent (SigmaAldrich, St. Louis, Mo.) and treated with DNaseI (Fermentas, Vilnius, Lithuania).

10 ug of the total RNA is treated using a Ribo-Zero rRNA Removal Kit (Illumina, San Diego, Calif.) and the remaining RNA purified using RNA Clean and Concentrators (Zymo Research, Irvine, Calif.).

A library is then prepared using a TruSeq Small RNA Library Preparation Kit (Illumina, San Diego, Calif.) following the manufacturer's instructions. This results in cDNAs having adapter sequences.

The resulting cDNA library is sequenced using a MiSeq Sequencer (Illumina, San Diego, Calif.).

C. Processing of Sequencing Data

Sequencing reads of the cDNA library are processed, for example, using the following method.

Adapter sequences are removed using cutadapt 1.1 (pypi.python.org/pypi/cutadapt/1.1) and about 15 nt are trimmed from the 3'end of the read to improve read quality.

Reads are aligned to the genome of the respective species (i.e., from which the putative tracrRNA was identified) with a mismatch allowance of 2 nucleotides.

Read coverage is calculated using BedTools (bedtools.readthedocs.org/en/latest/).

Integrative Genomics Viewer (IGV, www.broadinstitute.org/igv/) is used to map the starting (5') and ending (3') position of reads. Total reads retrieved for the putative tracrRNA are calculated from the SAM file of alignments.

The RNA-seq data is used to validate that a putative tracrRNA element is actively transcribed in vivo. Confirmed hits from the comparison of the in silico and RNA-seq screens are validated for functional ability of the identified tracrRNA sequence and its cognate crRNA to support Cas9-mediated cleavage of a double-stranded DNA target sequence using methods outline herein (e.g., Examples 1, 2, and 3).

Following the guidance of the present specification and Examples, the identification of novel tracrRNA sequences related to Cas9 proteins can be accomplished by one of ordinary skill in the art.

Example 7

T7E1 Assay for Detection of Target Sequence Modifications in Eukaryotic Cells

This Example illustrates the use of T7E1 assays to evaluate and compare the percent cleavage in cell of Cas9-Cpf1-NATNA/Cas9&Cpf1 complexes relative to selected double-stranded DNA target sequences.

A. Cell Transfections Using Cas Polynucleotide Components

The Cas9-Cpf1-NATNAs are transfected into HEK293 cells constitutively expressing *S. pyogenes* Cas9 and *Acidaminococcus* sp. Cpf1 (HEK293-Cas9-Cpf1), using the Nucleofector® 96-well Shuttle System (Lonza, Allendale, N.J.) and the following protocol. Cas9-Cpf1-NATNAs are prepared in an annealing buffer (1.25 mM HEPES, 0.625 mM $MgCl_2$, 9.375 mM KCl at pH 7.5), incubated for 2 minutes at 95° C., removed from a thermocycler, allowed to equilibrate to room temperature, and dispensed in a 5 µL final volume in a 96-well plate. Culture medium is aspirated from HEK293-Cas9-Cpf1 cells, the cells are washed once with calcium and magnesium-free PBS, and are then trypsinized by the addition of TrypLE (Life Technologies, Grand Island, N.Y.) followed by incubation at 37° C. for 3-5 minutes. Trypsinized cells are gently pipetted up and down to form a single-cell suspension and added to DMEM complete culture medium composed of DMEM culture medium (Life Technologies, Grand Island, N.Y.) containing 10% Fetal Bovine Serum (FBS; Thermo Fisher Scientific, Wilmington, Del.) and supplemented with penicillin and streptomycin (Life Technologies, Grand Island, N.Y.).

The cells are then pelleted by centrifugation for 3 minutes at 200×g, the culture medium aspirated, and cells re-suspended in PBS. The cells are counted using the Countess® II Automated Cell Counter (Life Technologies, Grand Island, N.Y.). $2.2 \times 10^7$ cells are transferred to a 1.5 ml microfuge tube and pelleted. The PBS is aspirated and the cells are re-suspended in Nucleofector™ SF (Lonza, Allendale, N.J.) solution to a density of $1 \times 10^7$ cells/mL. 20 µL of the cell suspension are then added to individual wells containing 5 uL of the Cas9-Cpf1-NATNA and the entire volume is transferred to the wells of a 96-well Nucleocuvette™ Plate (Lonza, Allendale, N.J.). The plate is loaded onto the Nucleofector™ 96-well Shuttle™ (Lonza, Allendale, N.J.) and cells are nucleofected using the 96-CM-130 Nucleofector™ program (Lonza, Allendale, N.J.). Post-nucleofection, 70 µL DMEM complete culture medium are added to each well, and 50 µL of the cell suspension are transferred to a collagen coated 96-well cell culture plate containing 150 µL pre-warmed DMEM complete culture medium. The plate is then transferred to a tissue culture incubator and maintained at 37° C. in 5% $CO_2$ for 48 hours.

B. Double-Stranded DNA Target Sequence Generation for T7E1 Assay gDNA is isolated from HEK293-Cas9-Cpf1 cells 48 hours after transfection of the Cas9-Cpf1-NATNA using 50 µL QuickExtract DNA Extraction solution (Epicentre, Madison, Wis.) per well followed by incubation at 37° C. for 10 minutes, 65° C. for 6 minutes and 95° C. for 3 minutes to stop the reaction. gDNA is then diluted with 150 µL water and samples are stored at −80° C.

DNA for T7E1 is generated by PCR amplification of double-stranded DNA target sequences (e.g., VEGFA and IDO2) from isolated gDNA. PCR reactions are set up using 80 µL gDNA as template with KAPA HiFi Hot Start polymerase and contain 0.5 U of polymerase, 1× reaction buffer, 0.4 mM dNTPs and 300 nM forward and reverse primers directed to the double-stranded DNA target sequence (e.g., Example 2, Table 3; SEQ ID NO. 5 and SEQ ID NO. 6; and SEQ ID NO. 7 and SEQ ID NO. 8) in a total volume of 25 µL. The DNA target sequence is amplified using the following conditions: 95° C. for 5 minutes, 4 cycles of 20 seconds at 98° C., 20 seconds at 70° C., minus 2° C./cycle, 30 seconds at 72° C., followed by 30 cycles of 15 seconds at 98° C., 20 seconds at 62° C., 20 seconds at 72° C., and a final extension at 72° C. for 1 minute.

C. T7E1 Assay

PCR-amplified double-stranded DNA target sequences for T7E1 assays are denatured at 95° C. for 10 minutes and then allowed to re-anneal by cooling to 25° C. at −0.5° C./s in a thermal cycler. The re-annealed DNA is incubated with 0.50 µL T7 Endonuclease I in 1× NEBuffer 2 buffer (New England Biolabs, Ipswich, Mass.) in a total volume of 15 µL for 25 minutes at 37° C. T7E1 reactions are analyzed using the Fragment Analyzer™ System (Advanced Analytical Technologies, Ames, Iowa) and the DNF-910 Double-stranded DNA Reagent Kit (Advanced Analytical Technologies, Ames, Iowa). The Fragment Analyzer™ System provides the concentration of each cleavage fragment and of the double-stranded DNA target sequence that remains after cleavage.

Cleavage percentages of the double-stranded DNA target sequences are calculated from the concentration of each cleavage fragment and the double stranded DNA target sequence that remains after cleavage has taken place, using the following formula:

$$\% \text{ cleavage} = \left(1 - \sqrt{\left(1 - \frac{(frag1 + frag2)}{(frag1 + frag2 + \text{parent})}\right)}\right) \quad \text{EQUATION 1}$$

In Equation 1, frag1 and frag2 concentrations correspond to the concentration of Cas9 cleavage fragments of the double-stranded DNA target sequence and parent corresponds to the double-stranded DNA target sequence that remains after cleavage has taken place.

The T7E1 assay for detection of target sequence modifications in eukaryotic cells provides data to demonstrate that the Cas9-Cpf1-NATNA/Cas9&Cpf1 protein complexes described herein facilitate Cas9 and Cpf1-mediated site-specific in vivo cleavage of multiple double-stranded DNA target sequences. sgRNA, crRNA and/or tracrRNA/crRNA polynucleotides having the same DNA target binding sequence as the Cas9-Cpf1-NATNA can also be included in the assay to compare the Cas9- and Cpf1-mediated site-specific cleavage percentages between the constructs.

Following the guidance of the present specification and Examples, the T7E1 assay described in this Example can be practiced by one of ordinary skill in the art with other Type II CRISPR Cas9 proteins or Type V CRISPR Cpf1 proteins and their cognate Cas9-Cpf1-NATNA.

Example 8

Probing for Sites Tolerant of Modification in Class 2 Type V Guide crRNA Backbones This Example describes the generation and testing of various modifications of Class 2 Type V guide crRNAs and their suitability for use in constructing cross-type-NATNAs.

In this Example, crRNA backbone sequences were modified, and the modified crRNA were tested with a cognate Cpf1 nuclease to facilitate identification of regions or positions in the Cpf1-crRNA backbone wherein a Cas9-sgRNA can be linked through hydrogen base-pair bonds or a covalent bond (e.g., phosphodiester bond).

Various regions in the *F. novicida* Cpf1-crRNA were selected for modification. Primers for the generation of modified Cpf1-crRNA were ordered from a commercial manufacturer. Double-stranded DNA templates for crRNA transcription were generated as previously describe (e.g., Example 1). Sequences used for crRNA template assembly are shown in Table 7.

TABLE 7

| crRNA Template Assembly Primers | | |
|---|---|---|
| Target sequence spacer | crRNA sequence modification | Primers used for PCR assembly |
| VEGFA | wild type crRNA | SEQ ID Nos. 1, 17, 27 |
| IDO2 | wild type crRNA | SEQ ID Nos. 1, 18, 4 |
| VEGFA | single-stranded 5' tail | SEQ ID Nos. 1, 19, 27 |
| IDO2 | single-stranded 5' tail | SEQ ID Nos. 1, 20, 4 |
| VEGFA | increased pseudo-knot length | SEQ ID Nos. 1, 21, 27 |
| IDO2 | increased pseudo-knot length | SEQ ID Nos. 1, 22, 4 |
| VEGFA | 3' hairpin addition | SEQ ID Nos. 1, 23, 27 |
| IDO2 | 3' hairpin addition | SEQ ID Nos. 1, 24, 4 |
| VEGFA | 5' hairpin addition | SEQ ID Nos. 1, 25, 27 |
| IDO2 | 5' hairpin addition | SEQ ID Nos. 1, 26, 4 |

Figure 14B:
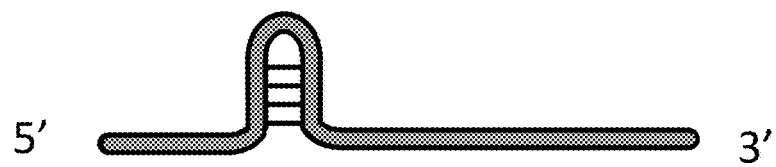
Figure 14C:
Figure 14D:
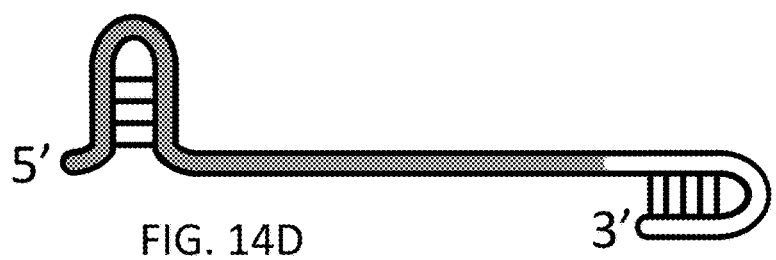
Figure 14E:
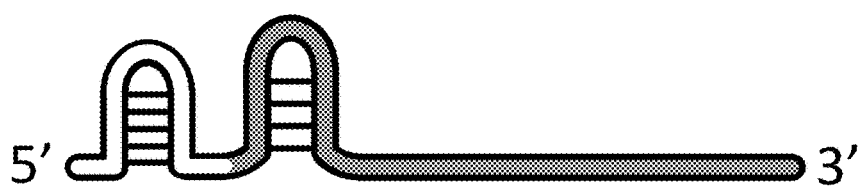

FIG. 14A illustrates the wild-type Cpf1-crRNA. FIG. 14B illustrates the wild-type Cpf1 pre-crRNA. Examples of modifications made to Cpf1-crRNA are diagrammed in FIG. 14C, FIG. 14D, and FIG. 14E, wherein the modifications are indicated by the non-shaded portions of the diagrammed modified Cpf1-crRNA. The corresponding sequences for the Cpf1-crRNAs are presented in Table 8, including the spacer, type of modification, (modified) crRNA sequence, and SEQ ID. NO. for the (modified) crRNA sequence, as well as the figure corresponding to general structure for each (modified) crRNA.

TABLE 8

| Modified Cpf1-crRNA Sequences | | | | |
|---|---|---|---|---|
| Target sequence spacer | crRNA sequence modification | Modified crRNA sequence | SEQ ID NO. | FIG. |
| VEGFA | wild type crRNA | GAAUUUCUACUGUUGUAGA UGAAAGGGGUGGGGGAG UUUGCU | SEQ ID NO. 28 | 14A |

TABLE 8-continued

Modified Cpf1-crRNA Sequences

| Target sequence spacer | crRNA sequence modification | Modified crRNA sequence | SEQ ID NO. | FIG. |
|---|---|---|---|---|
| IDO2 | wild type crRNA | GAAUUCUACUGUUGUAGA UGGUAGAGAAAGAAGCAGU GCCUGG | SEQ ID NO. 29 | 14A |
| VEGFA | single-stranded 5' tail | GGUCUAAGAACUUUAAAUA AUUUCUACUGUUGUAGAUG AAAGGGGUGGGGGGAGUU UGCU | SEQ ID NO. 30 | 14B |
| IDO2 | single-stranded 5' tail | GGUCUAAGAACUUUAAAUA AUUUCUACUGUUGUAGAUG GUAGAGAAAGAAGCAGUGC CUGG | SEQ ID NO. 31 | 14B |
| VEGFA | increased pseudo-knot length | GAAUUCUACUGUUCACUG CCGUAUAGGCAGUGAACUU GUAGAUGAAAGGGGUGGG GGGAGUUUGCU | SEQ ID NO. 32 | 14C |
| IDO2 | increased pseudo-knot length | GAAUUCUACUGUUCACUG CCGUAUAGGCAGUGAACUU GUAGAUGGUAGAGAAAGAA GCAGUGCCUGG | SEQ ID NO. 33 | 14C |
| VEGFA | 3' hairpin addition | GAAUUCUACUGUUGUAGA UGAAAGGGGUGGGGGGAG UUUGCUGCCAGGUUCACUG CCGUAUAGGCAG | SEQ ID NO. 34 | 14D |
| IDO2 | 3' hairpin addition | GAAUUCUACUGUUGUAGA UGGUAGAGAAAGAAGCAGU GCCUGGGCCAGGUUCACUGC CGUAUAGGCAG | SEQ ID NO. 35 | 14D |
| VEGFA | 5' hairpin addition | GGUUCACUGCCGUAUAGGC AGGCAAGAAUUUCUACUGU UGUAGAUGAAAGGGGUGG GGGGAGUUUGCU | SEQ ID NO. 36 | 14E |
| IDO2 | 5' hairpin addition | GGUUCACUGCCGUAUAGGC AGGCAAGAAUUUCUACUGU UGUAGAUGGUAGAGAAAGA AGCAGUGCCUGG | SEQ ID NO. 37 | 14E |

*S. pyogenes* Cas9 protein and *F. novicida* Cpf1 protein were recombinantly expressed in *E. coli* and purified for use in in vitro biochemical cleavage assays. VEGFA and IDO2 double-stranded DNA target sequences were generated as described in Example 2. Biochemical cleavage of PCR-generated target sequences were carried out essentially as described in Example 3, with the modification that only the *F. novicida* Cpf1 was used.

Figure 15:
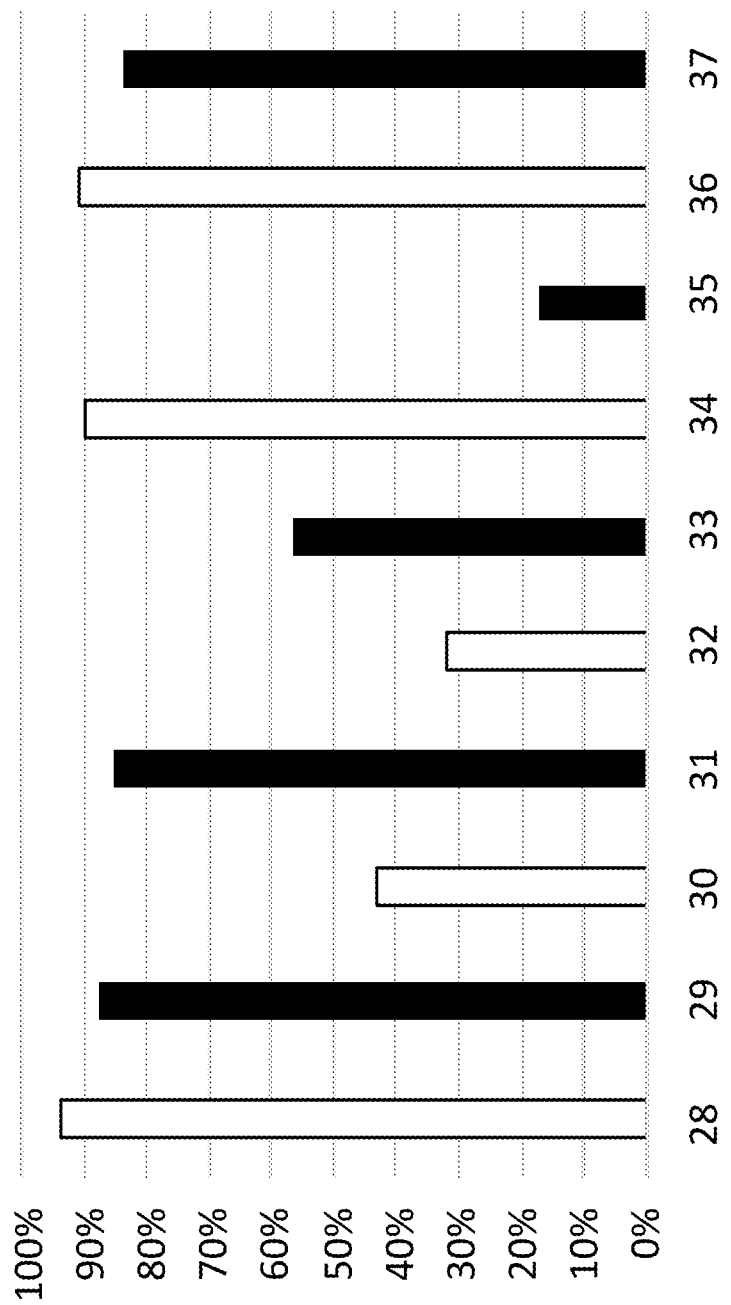
FIG. 15 presents the results of *F. novicida* Cpf1 biochemical cleavage assays using various modified Cpf1 crRNAs.

FIG. 15 presents the results of the *F. novicida* Cpf1 biochemical cleavage assay using the modified Cpf1-crRNAs (Table 8). The y-axis shows percent cleavage of a double-stranded DNA target sequence, and the x-axis shows the SEQ ID NO. corresponding to the (modified) Cpf1-crRNA used in the assay. As can be seen from the data, inclusion of additional RNA bases and secondary structures (e.g., hairpin elements) was tolerated in the Cpf1-crRNA.

The methods described in this Example can be used to identify locations in a Cpf1-crRNA sequence that permit engineering of the Cpf1-crRNA by linkage to a Cas9 crRNA, tracrRNA, or sgRNA to generate a Cas9-Cpf1-NATNA. Cpf1 crRNA from different species may exhibit different degrees of tolerance for various sequence modification. Additionally, different Cas9 crRNA, tracrRNA, or sgRNA may be more amenable for inclusion into a Cas9-Cpf1-NATNA.

Cpf1 crRNAs that are capable of mediating cleavage of a DNA target sequence with their cognate Cpf1 proteins can be validated for activity in cells using the method described in Example 4.

This Example can be practiced by one of ordinary skill in the art with other Class 2 Type V CRISPR proteins and their cognate Type V CRISPR guide crRNA. Following the guidance of the present specification and Examples, the modification of a Cpf1-crRNA (e.g., introduction of various sequence and secondary structural modifications, and/or deletion of various sequences) can be used to probe for locations for insertion or linkages to facilitate making a Cas9-Cpf1-NATNA.

Example 9

Probing for Sites Tolerant of Modification in Class 2 Type II Cas9 Guide RNA Backbones This Example describes the generation and testing of various modifications of Class 2 Type II guide RNA(s) and their suitability for use in constructing cross-type-NATNAs.

In this Example, modifications are introduced into the RNA backbone of Class 2 Type II CRISPR guide RNAs to identify locations for engineering or attachment of various nucleic acid sequences. The method described below is adapted from Briner, A., et al., Molecular Cell 56(2):333-339 (2014). Not all of the following steps are required for screening nor must the order of the steps be as presented.

A sgRNA from a Class 2 Type II CRISPR system is selected for engineering. The guide RNA sequence is modified in silico to introduce base substitution(s) in region(s) selected from one or more of the following: the lower stem, bulge, upper stem, tetraloop, nexus, linking sequences, and 3' hairpins. Base substitution can be used to introduce mismatches in the hydrogen base-pair interactions of any of the guide RNA regions, or base-pair mutation may preserve hydrogen base-pair interaction through substitution of two bases introducing alternative Watson-Crick base pairs. Substitution of bases can also be used to introduce novel hydrogen base-pair interaction within the guide RNA backbone (e.g., within the bulge sequence).

Regions of the guide RNA can be independently engineered to introduce secondary structure elements into the guide RNA backbone. Such modifications include hairpins, pseudo-knots, ribozymes, or other modification known to one skilled in the art. Furthermore, the guide RNA backbone can be modified to delete portions of the guide RNA backbone, either through deletion at the 5' end, 3' end or internal to the guide RNA.

In silico designed Class 2 Type II CRISPR guide RNA sequences are provided to a commercial manufacturer for synthesis.

Modified Class 2 Type II CRISPR guide RNAs are evaluated for their ability to support cleavage of a double-stranded DNA target sequence mediated by their cognate Cas9 proteins. Double-stranded DNA target sequences and biochemical cleavage assay are carried out in a manner similar to those described in Example 2 and Example 3. Guide RNAs that are capable of mediating cleavage of a DNA target sequence with their cognate Cas9 proteins can be validated for activity in cells using the method described in Example 4.

Following the guidance of the present specification and Examples, the modification of a Cas9 guide RNA(s) (e.g., introduction of various sequence and secondary structural modifications, and/or deletion of various sequences) can be used to probe for locations for insertion or linkages to facilitate making a Cas9-Cpf1-NATNA. This Example can be practiced by one of ordinary skill in the art with other Type II CRISPR Cas9 proteins and other Type II CRISPR guide RNA.

Example 10

Screening of Cross-Type-NATNAs Comprising DNA Target Binding Sequences

This Example illustrates the use of cross-type-NATNAs of the present invention to modify DNA target sequences present in human genomic DNA and to measure the level of cleavage activity at those sites.

Target sites (DNA target sequences) are first selected from genomic DNA. Cas9-Cpf1-NATNAs are designed to target the selected sequences. Assays (e.g., as described in Example 3) are performed to determine the level of DNA target sequence cleavage.

Not all of the following steps are required for every screening nor must the order of the steps be as presented, and the screening can be coupled to other experiments, or form part of a larger experiment.

A. Selecting DNA Target Regions (DNA Target Sequences) from Genomic DNA

All PAM sequences (e.g., NGG, TTTN) are identified within the selected genomic region.

One or more 20 nucleotide sequences (Cas9 DNA target sequence) that are 5' adjacent to a NGG PAM sequence are identified and selected.

One or more 24 nucleotide sequences (Cpf1 DNA target sequence) that are 3' adjacent to a TTTN PAM sequence are identified and selected.

Criteria for selection of nucleic acid target sequences can include, but are not limited to, the following: homology to other regions in the genome; percent G-C content; melting temperature; presences of homopolymer within the spacer; distance between the two sequences; and other criteria known to one skilled in the art.

The Cas9 DNA target binding sequence is appended to the 5' end of an appropriate Cas9-Cpf1-NATNA, and the Cpf1 DNA target binding sequence is appended to the 3' end of the same Cas9-Cpf1-NATNA (e.g., a Cas9-Cpf1-NATNA as illustrated in FIG. 4). A Cas9-Cpf1-NATNA construct is typically synthesized by a commercial manufacturer, and is based on sequences provided to the manufacturer. Alternatively, the Cas9-Cpf1-NATNA construct is produced as described in Example 1 by in vitro transcription.

A Cas9-Cpf1-NATNA, as described herein, is used with cognate Class 2 Type II and Class 2 Type V CRISPR Cas proteins (e.g., the Cas9-associated nucleic acids of a Cas9-Cpf1-NATNA bind their cognate Cas9 protein, and the Cpf1-associated nucleic acids of a Cas9-Cpf1-NATNA bind their cognate Cpf1 protein).

B. Determination of Cleavage Percentages and Specificity

In vitro cleavage percentages and specificity (e.g., the amount of off-target binding) related to a Cas9-Cpf1-NATNA are determined, for example, using the cleavage assays described in Example 3, and are compared as follows:

(1) If only a single pair of DNA target sequences are identified or selected for a Cas9-Cpf1-NATNA, the cleavage percentage and specificity for each of the DNA target sequences are determined. If so desired, cleavage percentage and/or specificity are altered in further experiments using methods including, but not limited to, modifying the Cas9-Cpf1-NATNA, or introducing effector proteins/effector protein-binding sequences to modify the Cas9-Cpf1-NATNA or one or both of the Cas proteins, or ligand/ligand binding moieties to modify the Cas9-Cpf1-NATNA or one or both of the Cas proteins.

(2) If multiple pairs of DNA target sequences are identified or selected for a Cas9-Cpf1-NATNA, the percentage cleavage data and site-specificity data obtained from the cleavage assays are compared between different DNAs comprising the target binding sequence to identify the DNA target sequences having the desired cleavage percentage and specificity. Cleavage percentage data and specificity data provide criteria on which to base choices for a variety of applications. For example, in some situations the activity of the Cas9-Cpf1-NATNAs may be the most important factor. In other situations, the specificity of the cleavage site may be relatively more important than the cleavage percentage. If so desired, cleavage percentage and/or specificity are altered in further experiments using methods of the present invention including, but not limited to, modifying the Cas9-Cpf1-NATNA, or introducing effector proteins/effector protein-binding sequences to modify the Cas9-Cpf1-NATNA or one or both of the Cas proteins, or ligand/ligand binding moieties to modify the Cas9-Cpf1-NATNA or one or both of the Cas proteins.

Alternatively, or in addition to the in vitro analysis, in cell cleavage percentages and specificities associated with Cas9-Cpf1-NATNAs obtained using, for example, the method described in Example 4, are compared as follows:

(1) If only a single pair of DNA target sequences are identified or selected for a Cas9-Cpf1-NATNA, the cleavage percentage and specificity for each of the DNA target sequences are determined. If so desired, cleavage percentage and/or specificity are altered in further experiments using including, but not limited to, modifying the Cas9-Cpf1-NATNA, or introducing effector proteins/effector protein-binding sequences to modify the Cas9-Cpf1-NATNA or one or both of the Cas proteins, or ligand/ligand binding moieties to modify the Cas9-Cpf1-NATNA or one or both of the Cas proteins.

(2) If multiple pairs of DNA target sequences are identified or selected for a Cas9-Cpf1-NATNA, the percentage cleavage data and site-specificity data obtained from the cleavage assays are compared between different DNAs comprising the target binding sequences to identify the DNA target sequences having the desired cleavage percentage and specificity. Cleavage percentage data and specificity data provide criteria on which to base choices for a variety of applications. For example, in some situations the activity of the Cas9-Cpf1-NATNAs may be the most important factor. In other situations, the specificity of the cleavage site may be relatively more important than the cleavage percentage. If so desired, cleavage percentage and/or specificity are altered in further experiments using methods of the present invention including, but not limited to, modifying the Cas9-Cpf1-NATNA, or introducing effector proteins/effector protein-binding sequences to modify the Cas9-Cpf1-NATNA or one or both of the Cas proteins, or ligand/ligand binding moieties to modify the Cas9-Cpf1-NATNA or one or both of the Cas proteins.

Following the guidance of the present specification and Examples, the screening described in this Example can be practiced by one of ordinary skill in the art with other cross-type-NATNAs for use with cognate Class 2 Type II CRISPR Cas9 proteins and Class 2 Type V CRISPR Cpf1 proteins.

As is apparent to one of skill in the art, various modifications and variations of the above embodiments can be made without departing from the spirit and scope of this invention. Such modifications and variations are within the scope of this invention.

The invention claimed is:

1. A method of modulating transcription of a gene comprising regulatory element sequences, comprising:
   contacting a first nucleic acid target sequence and a second nucleic acid target sequence with a nucleic acid/protein composition comprising,
      an engineered CRISPR Class 2 cross-type-nucleic acid targeting nucleic acid ("CRISPR Class 2 cross-type-NATNA") comprising,
         a CRISPR Type V Cpf1-associated nucleic-acid targeting nucleic acid, having a 5' end and a 3' end, comprising a spacer element complementary to the first nucleic acid target sequence ("Cpf1-NATNA"),
         a first CRISPR Type II Cas9-associated nucleic-acid targeting nucleic acid, having a 5' end and a 3' end, comprising a spacer element complementary to the second nucleic acid target sequence ("first Cas9-NATNA"), and
         a second CRISPR Type II Cas9-associated nucleic-acid targeting nucleic acid, having a 5' end and a 3' end, comprising a tracr element ("second Cas9-NATNA"),
   wherein the first Cas9-NATNA or the second Cas9-NATNA is connected with the Cpf1-NATNA, wherein the nucleic acid/protein composition comprises the CRISPR Class 2 cross-type-NATNA complexed with a catalytically inactive Cas9 ("dCas9") protein and a catalytically inactive Cpf1 ("dCpf1") protein; wherein the first nucleic acid target sequence, the second nucleic acid target sequence, or both the first nucleic acid target sequence and the second nucleic acid target sequence, comprise the regulatory element sequences; wherein the contacting facilitates the binding of the nucleic acid/protein composition to the regulatory element sequences, and the binding of the nucleic acid/protein composition modulates transcription of the gene comprising the regulatory element sequences; and wherein the method of modulating transcription of the gene is carried out in vitro, in a cultured cell, or in a non-human subject.

2. The method of claim 1, wherein the first Cas9-NATNA or the second Cas9-NATNA is covalently connected with the Cpf1-NATNA; and wherein the Cpf1-NATNA is covalently connected with the 5' end or the 3' end of the first Cas9-NATNA or to the 5' end or the 3' end of the second Cas9-NATNA.

3. The method of claim 1, wherein the Cpf1-NATNA further comprises a linker element nucleotide sequence covalently connected with the 5' end or the 3' end of the Cpf1-NATNA; and wherein, if the linker element nucleotide sequence is covalently connected with the 3' end of the Cpf1-NATNA, the linker element nucleotide sequence is located 3' of the Cpf1-NATNA spacer element.

4. The method of claim 3, wherein the first Cas9-NATNA further comprises a linker element nucleotide sequence covalently connected with the 5' end or the 3' end of the first Cas9-NATNA and, if the linker element nucleotide sequence is covalently connected with the 5' end of the first Cas9-NATNA, the linker element nucleotide sequence is located 5' of the first Cas9-NATNA spacer element; or wherein the second Cas9-NATNA further comprises a linker element nucleotide sequence covalently connected with the 5' end or the 3' end of the second Cas9-NATNA.

5. The method of claim 4, wherein the first Cas9-NATNA linker element nucleotide sequence or the second Cas9-NATNA linker element nucleotide sequence is non-covalently connected with the Cpf1-NATNA through hydrogen base-pair bonding.

6. The method of claim 1, wherein the 3' end of the first Cas9-NATNA is covalently connected through a loop element with the 5' end of the second Cas9-NATNA, resulting in a single-Cas9-associated nucleic-acid targeting nucleic acid ("single-Cas9-NATNA"), having a 5' end and a 3' end; and wherein the single-Cas9-NATNA comprises the first Cas9-NATNA and the second Cas9-NATNA.

7. The method of claim 6, wherein the single-Cas9-NATNA further comprises a linker element nucleotide sequence covalently connected with the 5' end or the 3' end of the single-Cas9-NATNA and, if the linker element nucleotide sequence is covalently connected with the 5' end of the single-Cas9-NATNA, the linker element nucleotide sequence is located 5' of the single-Cas9-NATNA spacer element; wherein the Cpf1-NATNA further comprises a linker element nucleotide sequence covalently connected with the 5' end or the 3' end of the Cpf1-NATNA and, if the linker element nucleotide sequence is covalently connected with the 3' end of the Cpf1-NATNA, the linker element nucleotide sequence is located 3' of the Cpf1-NATNA spacer element; and wherein the single-Cas9-NATNA is non-covalently connected with the Cpf1-NATNA through hydrogen base-pair bonding of the single-Cas9-NATNA linker element nucleotide sequence with the Cpf1-NATNA linker element nucleotide sequence.

8. The method of claim 6, wherein the single-Cas9-NATNA is covalently connected with the Cpf1-NATNA; and wherein the Cpf1-NATNA is covalently connected with the 5' end or the 3' end of the single-Cas9-NATNA.

9. The method of claim 6, wherein the single-Cas9-NATNA comprises a linker element nucleotide sequence covalently connected with the 5' end or the 3' end of the single-Cas9-NATNA; and wherein, if the linker element nucleotide sequence is covalently connected with the 5' end of the single-Cas9-NATNA, the linker element nucleotide sequence is located 5' of the single-Cas9-NATNA spacer element.

10. The method of claim 6, wherein the Cpf1-NATNA comprises a linker element nucleotide sequence covalently connected with the 5' end or the 3' end of the Cpf1-NATNA; and wherein, if the linker element nucleotide sequence is covalently connected with the 3' end of the Cpf1-NATNA, the linker element nucleotide sequence is located 3' of the Cpf1-NATNA spacer element.

11. The method of claim 1, wherein at least one of the Cpf1-NATNA, the first Cas9-NATNA, or the second Cas9-NATNA comprises RNA.

12. The method of claim 11, wherein at least one of the Cpf1-NATNA, the first Cas9-NATNA, or the second Cas9-NATNA comprises DNA.

13. The method of claim 1, wherein at least one of the Cpf1-NATNA, the first Cas9-NATNA, or the second Cas9-NATNA comprises DNA.

14. The method of claim 1, wherein the cultured cell is a bacterial cell or an archaeal cell.

15. The method of claim 1, wherein the dCas9 protein, the dCpf1 protein, or each of the dCas9 protein and the dCpf1 protein is fused to a transcription repressor domain.

16. The method of claim 1, wherein the dCas9 protein, the dCpf1 protein, or each of the dCas9 protein and the dCpf1 protein is fused to a transcription activator domain.

17. The method of claim 1, wherein the modulating is transcriptional activation of the gene.

18. The method of claim 1, wherein the modulating is transcriptional repression of the gene.

* * * * *